US012729181B2

(12) United States Patent
Kwon et al.

(10) Patent No.: US 12,729,181 B2
(45) Date of Patent: Sep. 8, 2026

(54) COMPOUNDS, COMPOSITIONS, AND METHODS FOR MODULATING CALCIUM ION HOMEOSTASIS

(71) Applicant: The Regents of the University of California, Oakland, CA (US)

(72) Inventors: Ohyun Kwon, Los Angeles, CA (US); Aslam Shaikh, Los Angeles, CA (US); Nathan John Dupper, Los Angeles, CA (US); Changmin Xie, Los Angeles, CA (US); Adam Langenbacher, Los Angeles, CA (US); Jau-Nian Chen, Los Angeles, CA (US); Jiannan Zhao, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 956 days.

(21) Appl. No.: 17/799,521

(22) PCT Filed: Feb. 12, 2021

(86) PCT No.: PCT/US2021/017869

§ 371 (c)(1),
(2) Date: Aug. 12, 2022

(87) PCT Pub. No.: WO2021/163493

PCT Pub. Date: Aug. 19, 2021

(65) Prior Publication Data

US 2023/0150935 A1 May 18, 2023

Related U.S. Application Data

(60) Provisional application No. 62/975,541, filed on Feb. 12, 2020.

(51) Int. Cl.

| | |
|---|---|
| ***C07D 207/48*** | (2006.01) |
| ***A61P 9/06*** | (2006.01) |
| ***C07D 401/04*** | (2006.01) |
| ***C07D 405/04*** | (2006.01) |
| ***C07D 409/04*** | (2006.01) |
| ***C07D 413/04*** | (2006.01) |

(52) U.S. Cl.

CPC .............. *C07D 207/48* (2013.01); *A61P 9/06* (2018.01); *C07D 401/04* (2013.01); *C07D 405/04* (2013.01); *C07D 409/04* (2013.01); *C07D 413/04* (2013.01)

(58) Field of Classification Search

CPC .. C07D 207/48; C07D 401/04; C07D 405/04; C07D 409/04; C07D 413/04; A61P 9/06; A61P 9/00; A61K 31/40; A61K 31/4439

See application file for complete search history.

(56) References Cited

U.S. PATENT DOCUMENTS

2023/0150935 A1 5/2023 Kwon et al.

FOREIGN PATENT DOCUMENTS

| | | | | |
|---|---|---|---|---|
| WO | WO-2004/110996 A1 | | 12/2004 | |
| WO | WO-2005/115976 A1 | | 12/2005 | |
| WO | WO-2005/121085 A1 | | 12/2005 | |
| WO | WO-2016100379 A1 | * | 6/2016 | ............. A61K 31/40 |
| WO | WO-2021/163493 A1 | | 8/2021 | |

OTHER PUBLICATIONS

CAS Registry No. 911818-45-6 (which entered the STN database on Nov. 1, 2006). (Year: 2006).*

CAS Registry No. 212070-77-4 (which entered the STN database on Oct. 1, 1998). (Year: 1998).*

U.S. Appl. No. 17/573,442, Monitoring.

Cai et al., "Catalytic asymmetric total synthesis of (-)-actinophyllic acid," J Am Chem Soc, 138(10): 3298-3301 (2016).

Castellano et al., "Small-molecule inhibitors of protein geranylgeranyltransferase type I," J Am Chem Soc, 129(18): 5843-5845 (2007).

Fleury-Brégeot et al., "Screening of chiral phosphines as catalysts for the enantioselective [3+2] annulations of N-tosylimines with allenic esters," Tetrahedron, 63(48): 11920-11927 (2007).

International Search Report and Writen Opinion for International Application No. PCT/US2021/017869 dated Apr. 28, 2021.

Nguyen et al., "Synthesis of chiral thiourea-phosphine organocatalysts derived from I-proline," Tetrahedron Lett, 55(46): 6377-6380 (2014).

Smaligo et al., "Carvone-derived P-stereogenic phosphines: design, synthesis, and use in allene-imine [3+2] annulation," ACS Catal, 8(6): 5188-5192 (2018).

Zhang et al., "Design and Enantioselective Construction of Axially Chiral Naphthyl-Indole Skeletons," Angew Chemie, 129(1): 122-127 (2017).

Andrews et al., "Phosphine-catalyzed intramolecular γ-umpolung addition of α-aminoalkylallenic esters: facile synthesis of 3-carbethoxy-2-alkyl-3-pyrrolines." Chemical Communications 48(43) (2012): 5373-5375.

Balan et al., "Efficient microwave-assisted formation of functionalized 2, 5-dihydropyrroles using ruthenium-catalyzed ring-closing metathesis." Tetrahedron letters 45(15) (2004): 3089-3092.

Declerck et al. "Sequential aza-Baylis-Hillman/Ring Closing Metathesis/Aromatization as a Novel Route for the Synthesis of Substituted Pyrroles." The Journal of Organic Chemistry 69(24) (2004): 8372-8381.

Declerck et al., "2-Trimethylsilylethanesulfonyl (SES) versus Tosyl (Ts) protecting group in the preparation of nitrogen-containing five-membered rings. A novel route for the synthesis of substituted pyrrolines and pyrrolidines." The Journal of Organic Chemistry 72.4 (2007): 1518-1521.

(Continued)

*Primary Examiner* — Kamal A Saeed
*Assistant Examiner* — Meghan C Heasley
(74) *Attorney, Agent, or Firm* — Foley Hoag LLP; David P. Halstead; Alexander J. Chatterley

(57) ABSTRACT

The present disclosure relates to compounds that are capable of modulating calcium ion homeostasis and treating disorders related thereto. The disclosure further relates to methods of making the aforementioned compounds.

17 Claims, No Drawings

(56) References Cited

OTHER PUBLICATIONS

Drop et al., "Continuous flow ring-closing metathesis, an environmentally-friendly route to 2, 5-dihydro-1 H-pyrrole-3-carboxylates." Green Chemistry 19(7) (2017): 1647-1652.
Extended European Search Report for EP Application No. 21754577.1 dated Feb. 12, 2024.
Fang et al., "Cooperative, highly enantioselective phosphinothiourea catalysis of imine-allene [3+2] cycloadditions." Journal of the American Chemical Society 130(17) (2008): 5660-5661.
Grychowska et al., "Application of the ring-closing metathesis to the formation of 2-aryl-1H-pyrrole-3-carboxylates as building blocks for biologically active compounds." Tetrahedron 72(47) (2016): 7462-7469.
Henry et al., "Hydroxyproline-derived pseudoenantiomeric [2.2. 1] bicyclic phosphines: asymmetric synthesis of (+)-and (-)-pyrrolines." Journal of the American Chemical Society 136.34 (2014): 11890-11893.
Ishikawa et al., "Asymmetric Synthesis of 2-Alkyl-Substituted 2, 5-Dihydropyrroles from Optically Active Aza-Baylis-Hillman Adducts. Formal Synthesis of (-)-Trachelanthamidine." The Journal of Organic Chemistry 75.11 (2010): 3578-3586.
Jean et al., "Phosphine-catalyzed enantioselective [3+2] annulations of 2, 3-butadienoates with imines." Tetrahedron Letters 47(13) (2006): 2141-2145.
Kitagaki et al., "Planar chiral [2.2] paracyclophane-based phosphine-phenols: use in enantioselective [3+2] annulations of allenoates and N-tosylimines." Organic & Biomolecular Chemistry 16(10) (2018): 1770-1778.
Lopes et al., "Microwave-assisted Reactions of Allenic Esters: [3+2] Annulations and Allenoate-Claisen Rearrangement." Arkivoc (2010): 70-81.
Panossian et al., "Use of Allenylphosphonates as New Substrates for Phosphane-Catalyzed [3+2] and [4+2] Annulations." (2008): 3826-3833.
Scherer et al., "A promising new catalyst family for enantioselective cycloadditions involving allenes and imines: chiral phosphines with transition metal-CH2—P: linkages." Tetrahedron Letters 47(36) (2006): 6335-6337.
Shi et al., "Synthesis of Substituted Chromenes through the DABCO-Catalyzed Reaction of But-3-yn-2-one and Methyl Propiolate with Salicyl N-Tosylimines (DABCO=1, 4-diazabicyclo [2.2. 2] octane)." Chemistry—A European Journal 12(12) (2006): 3374-3378.
Sun et al., "Asymmetric Organocatalytic Allylic Substitution of Morita-Baylis-Hillman Carbonates with Allylamines for the Synthesis of 2, 5-Dihydropyrroles." The Journal of Organic Chemistry 76(19) (2011): 7826-7833.
Wang et al., "Diversity through a branched reaction pathway: Generation of multicyclic scaffolds and identification of antimigratory agents." Chemistry—A European Journal 17(2) (2011): 649-654.
Xu et al., "A novel [3+2] cycloaddition approach to nitrogen heterocycles via phosphine-catalyzed reactions of 2, 3-butadienoates or 2-butynoates and dimethyl acetylenedicarboxylate with imines: A convenient synthesis of pentabromopseudilin." The Journal of Organic Chemistry 63(15) (1998): 5031-5041.

* cited by examiner

COMPOUNDS, COMPOSITIONS, AND METHODS FOR MODULATING CALCIUM ION HOMEOSTASIS

RELATED APPLICATIONS

This application is the § 371 National Stage of PCT/US2021/017869, filed Feb. 12, 2021, which claims the benefit of U.S. Provisional Patent Application No. 62/975,541, filed on Feb. 12, 2020, the contents of each of which are hereby incorporated by reference in their entirety.

RELATED APPLICATIONS

This application claims the benefit of U.S. Provisional Patent Application No. 62/975,541, filed on Feb. 12, 2020, the contents of which are hereby incorporated by reference in their entirety.

STATEMENT OF GOVERNMENT SUPPORT

This invention was made with government support under GM071779 and HL126051, awarded by the National Institutes of Health. The government has certain rights in the invention.

BACKGROUND

During development, well-orchestrated cellular processes guide cells from diverse lineages to integrate into the primitive heart tube and establish rhythmic and coordinated contractions. While many genes and pathways important for cardiac morphogenesis have been identified, molecular mechanisms governing embryonic cardiac rhythmicity are poorly understood. The findings that $Ca^{2+}$ waves traveling across the heart soon after the formation of the primitive heart tube (Chi et al., 2008, PLoS Biol 6, e109) and that loss of function of key Ca2+ regulatory proteins, such as the L-type Ca2+ channel, Na/K-ATPase and sodium calcium exchanger 1 (NCX1), severely impairs normal cardiac function (Rottbauer et al., 2001, Dev Cell 7, 265-275; Shu et al., 2003, Development 130, 6165-6173; Ebert et al., 2005, Proc Natl Acad Sci U S A 102, 17705-17710; Langenbacher et al., 2005, Proc Natl Acad Sci U S A 102, 17699-17704), indicate an essential role for Ca2+ handling in the regulation of embryonic cardiac function. Indeed, Defects in cardiac Ca+handling and $Ca^+$ overload, for example during cardiac ischemia/reperfusion or in long QT syndrome, are well known causes of contractile dysfunction and many types of arrhythmias including early and delayed afterdepolarizations and Torsade des pointes (Bers, 2002, Nature 415, 198-205; Choi et al., 2002, J Physiol 543, 615-631; Yano et al., 2008, Circ J 72, A22-30; Greiser et al., 201 1, Cardiovasc Res 89, 722-733). Thus, there is an ongoing need for new modulators of $Ca^+$ homeostasis.

SUMMARY OF THE INVENTION

In one aspect, the present disclosure provides compound represented by Formula I:

I

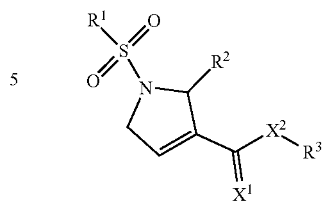

or a pharmaceutically acceptable salt thereof; wherein $X^1$ is O, S, or $NR^4$; or $X^1$, $X^2$, and $R^3$, with the carbon that separates $X^1$ and $X^2$, combine to form a heterocyclyl;

$X^2$ is O, S, or $NR^5$; or $X^2$ and $R^3$ combine to form a heterocyclyl;

$R^1$ is alkyl, cycloalkyl, aryl, heteroaryl, or heterocyclyl;

$R^2$ is aryl or heteroaryl;

$R^3$ is H or alkyl; and $R^4$ and $R^5$ are each independently H or alkyl.

In further aspects, the present disclosure provides compositions comprising a compound of formula I and at least one pharmaceutically acceptable excipient.

In yet further aspects, the present disclosure provides methods of modulating cardiac rhythmicity in a subject, comprising administering a compound of Formula I or a composition thereof to the subject.

In yet further aspects, the present disclosure provides methods of treating a cardiac disorder in a subject, comprising administering a compound of Formula I or a composition thereof to the subject.

In yet further aspects, the present disclosure provides methods of making compounds of Formula I.

DETAILED DESCRIPTION OF THE INVENTION

Tightly regulated $Ca^+$ homeostasis is a prerequisite for proper cardiac function. To dissect the regulatory network of cardiac $Ca^+$ handling, a chemical suppressor screen on zebrafish tremblor embryos, which suffer from $Ca^+$ extrusion defects was performed. Efsevin was identified based on its potent activity to restore coordinated contractions in tremblor. Furthermore, efsevin was shown to bind to $VDAC_2$, a potentiator of mitochondrial Ca uptake which accelerates the transfer of $Ca^+$ from intracellular stores into mitochondria. Moreover, in cardiomyocytes, efsevin restricts the temporal and spatial boundaries of Ca+sparks and thereby inhibits Ca+overload-induced erratic $Ca^+$ waves and irregular contractions. In addition, it has been demonstrate that the overexpression of VDAC2 recapitulates the suppressive effect of efsevin on tremblor embryos whereas VDAC2 deficiency attenuates efsevin's rescue effect and that VDAC2 functions synergistically with MCU to suppress cardiac fibrillation in tremblor. Together, these findings demonstrate that efsevin is able to modulate $VDAC_2$-dependent mitochondrial Ca+uptake in the regulation of cardiac rhythmicity. However, efsevin has poor metabolic stability in vivo and thus is an undesirable drug candidate. Disclosed herein are analogs of efsevin that possess greater metabolic stability and/or activity.

In one aspect, the present disclosure provides compounds represented by Formula I:

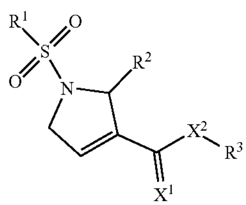

I or a pharmaceutically acceptable salt thereof; wherein $X^1$ is O, S, or $NR^4$; or $X^1$, $X^2$, and $R^3$ combine to form a heterocyclyl;

$X^2$ is O, S, or $NR^5$; or $X^2$ and $R^3$ combine to form a heterocyclyl;

$R^1$ is alkyl, cycloalkyl, aryl, heteroaryl, or heterocyclyl;

$R^2$ is aryl or heteroaryl;

$R^3$ is H or alkyl; and $R^4$ and $R^5$ are each independently H or alkyl.

In certain embodiments of formula I, the compound is not

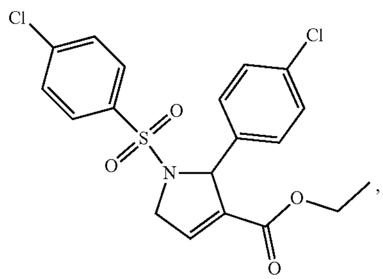,

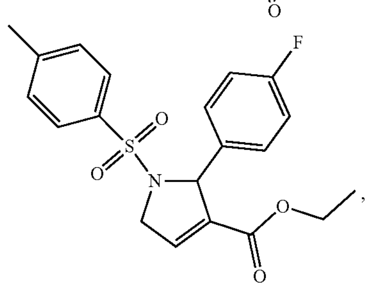,

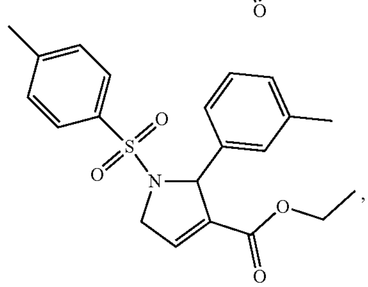,

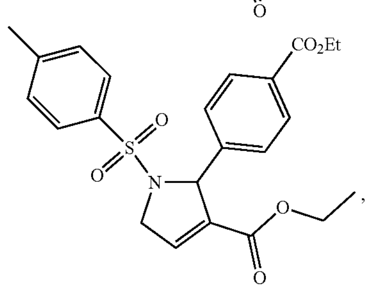,

-continued

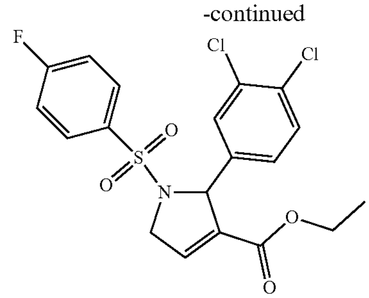,

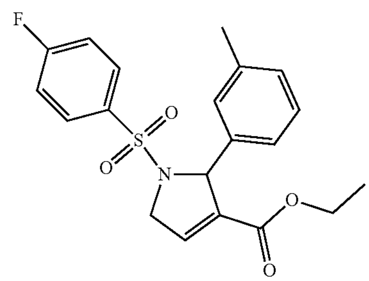,

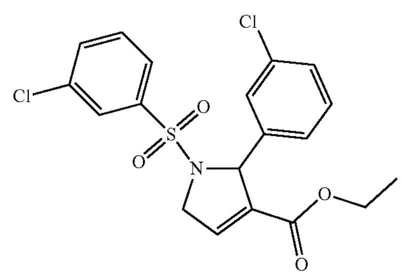,

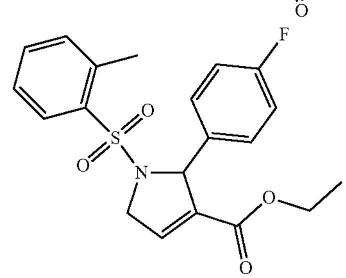,

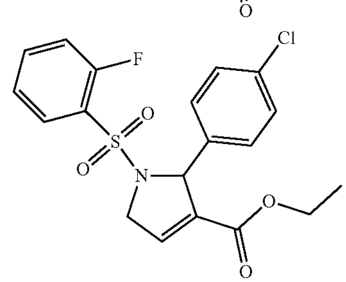,

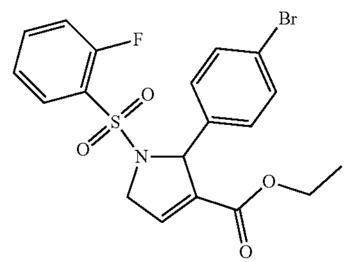,

-continued
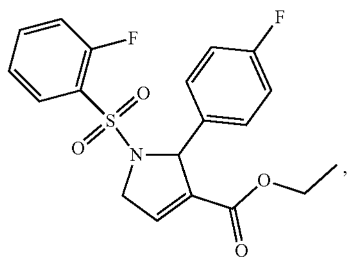
,
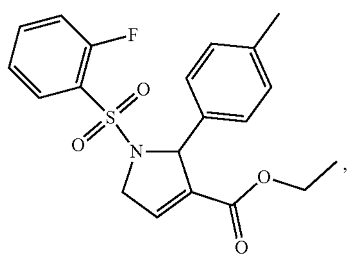
,
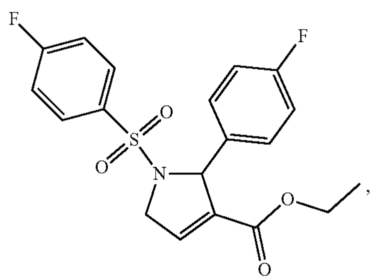
,
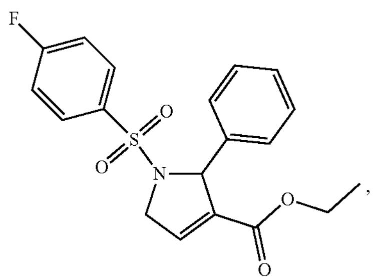
,
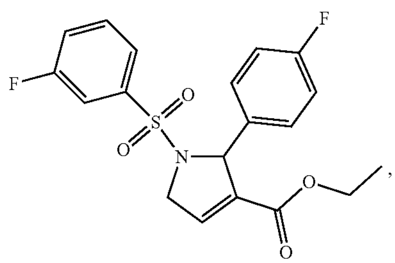
,
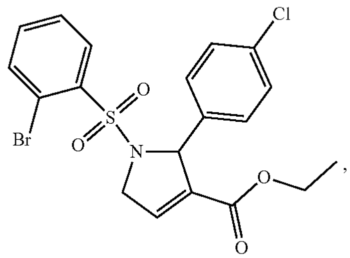
,
-continued
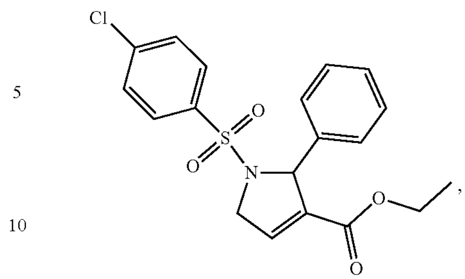
,
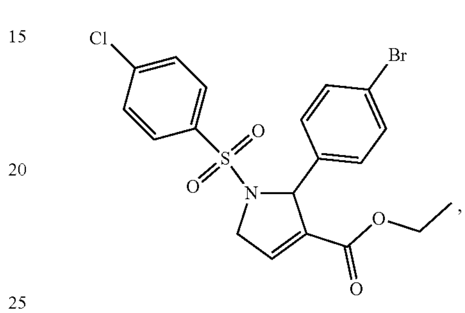
,
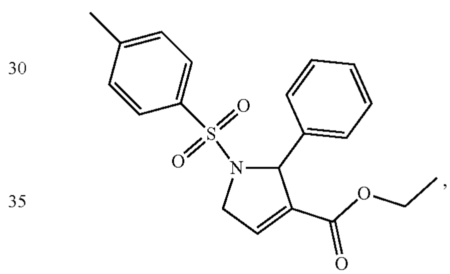
,
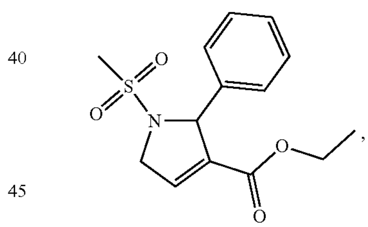
,
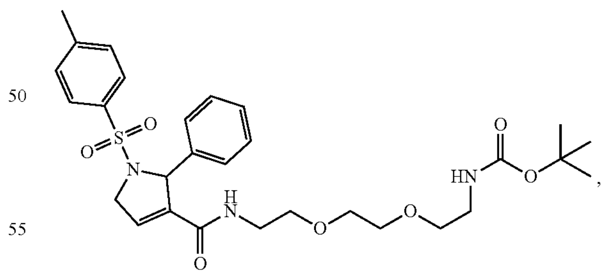
,
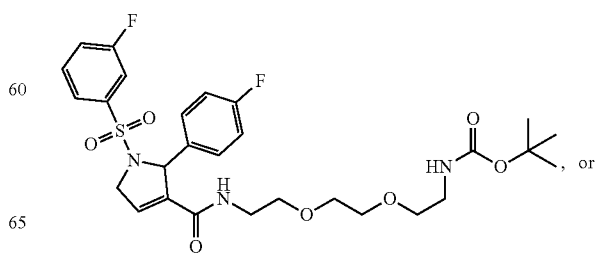
, or -continued

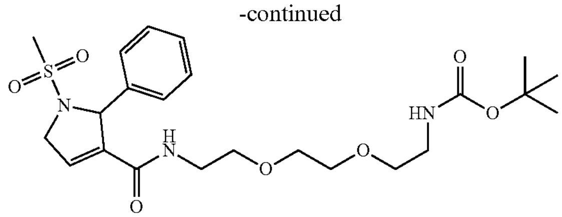

In certain embodiments of Formula I, if $R^1$ is 3-fluorophenyl, $R^2$ is 4-fluorophenyl, $X^1$ is O, and $R^3$ is ethyl, then $X^2$ is $NR^5$ or S. In certain embodiments, if $R^1$ is methyl, $X^1$ is O, $X^2$ is O, and $R^3$ is ethyl, then $R^2$ is substituted.

In certain embodiments of Formula I, the compound is represented by Formula IIa:

IIIa

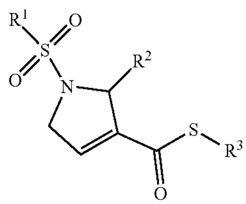

or a pharmaceutically acceptable salt thereof.

In certain other embodiments of Formula I, the compound is represented by Formula IIIb:

IIIb

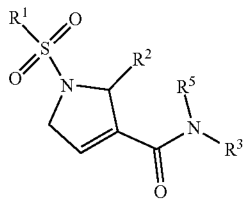

or a pharmaceutically acceptable salt thereof.

In certain other embodiments of Formula I, the compound is represented by Formula IIc:

IIIc

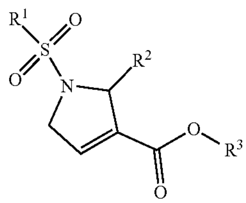

or a pharmaceutically acceptable salt thereof.

In certain embodiments of Formula I, IIIa, IIIb, or IIIc, $R^2$ is in the R-configuration. In other embodiments, $R^2$ is in the S-configuration.

In certain embodiments of Formula I, IIIa, IIIb, or IIIc, the compound has an enantiomeric excess (ee) greater than 95%, 96%, 97%, 98%, or 99%. In certain preferred embodiments, the compound is substantially free of one enantiomer.

In certain embodiments of Formula I, IIIa, IIIb, or IIIc, $R^2$ is heteroaryl (e.g., benzodioxolyl, pyridyl, or thiophenyl). In other embodiments, $R^2$ is phenyl or naphthyl.

In certain embodiments of Formula I, $X^1$, $X^2$, and $R^3$, with the carbon that separates $X^1$ and $X^2$, combine to form a heterocyclyl (e.g., oxazolinyl).

In certain embodiments of Formula I, IIIa, IIIb, or IIIc, $R^1$ is alkyl (e.g., methyl).

In certain embodiments of Formula I, IIIa, IIIb, or IIIc, the compound is represented by Formula Ia:

Ia

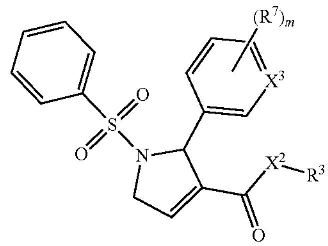

or a pharmaceutically acceptable salt thereof; wherein $X^2$ is O, S, or $NR^5$;

$X^3$ is CH, $CR^7$, or N;

$R^5$ is H or alkyl;

$R^6$ and $R^7$ are each, independently for each occurrence, selected from alkyl, halo, hydroxyl, carboxyl, acyl, ester, thioester, alkoxy, phosphoryl, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, aralkyl, carbamoyl, alkylcarbamoyl (e.g., N-methycarbamoyl or N,N-dimethylcarbamoyl).

n and m are each independently 0-5.

In other embodiments of Formula I, IIIa, IIIb, or IIIc, the compound is represented by Formula Ib:

Ib

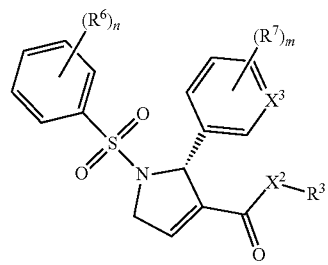

or a pharmaceutically acceptable salt thereof; wherein $X^2$ is O, S, or $NR^5$;

$X^3$ is CH, $CR^7$, or N;

$R^5$ is H or alkyl;

$R^6$ and $R^7$ are each, independently for each occurrence, selected from alkyl, halo, hydroxyl, carboxyl, acyl, ester, thioester, alkoxy, phosphoryl, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, aralkyl, carbamoyl, alkylcarbamoyl (e.g., N-methycarbamoyl or N,N-dimethylcarbamoyl).

n and m are each independently 0-5.

In certain embodiments of Formula I, Ia, Ib, IIIa, IIIb, or IIIc, n is 0. In other embodiments, n is 1.

In certain embodiments of Formula I, Ia, Ib, IIIa, IIIb, or IIIc, m is 0. In other embodiments, m is 1. In yet other embodiments, m is 2.

In certain embodiments of Formula I, Ia, Ib, IIIa, IIIb, or IIIc, the compound is represented by Formula Ic or Id:

Ic

Id

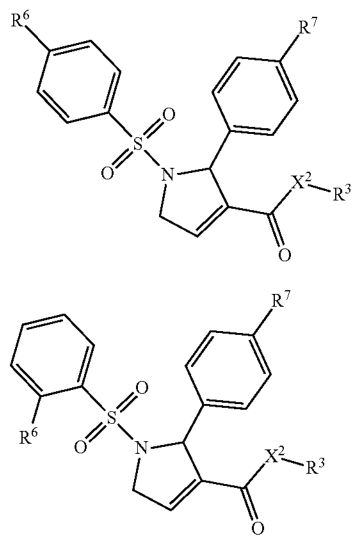

or a pharmaceutically acceptable salt thereof; wherein $X^2$ is O, S, or $NR^5$;

$X^3$ is CH, $CR^7$, or N;

$R^5$ is H or alkyl;

$R^6$ and $R^7$ are each, independently for each occurrence, selected from alkyl, halo, hydroxyl, carboxyl, acyl, ester, thioester, alkoxy, phosphoryl, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, aralkyl, carbamoyl, alkylcarbamoyl (e.g., N-methycarbamoyl or N,N-dimethylcarbamoyl).

n and m are each independently 0-5.

In certain embodiments of Formula I, Ia, Ib, Ic, Id, IIIa, IIIb, or IIIc, the compound is represented by Formula Ie or If:

Ie

If

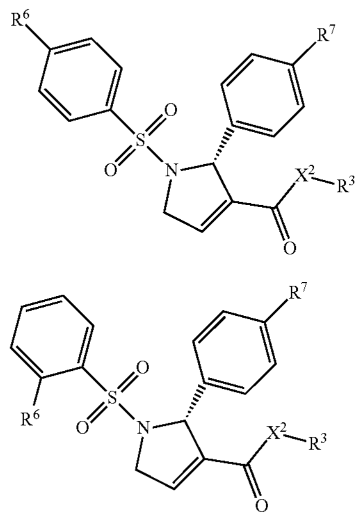

or a pharmaceutically acceptable salt thereof; wherein $X^2$ is O, S, or $NR^5$;

$X^3$ is CH, $CR^7$, or N;

$R^5$ is H or alkyl;

$R^6$ and $R^7$ are each, independently for each occurrence, selected from alkyl, halo, hydroxyl, carboxyl, acyl, ester, thioester, alkoxy, phosphoryl, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, aralkyl, carbamoyl, alkylcarbamoyl (e.g., N-methycarbamoyl or N,N-dimethylcarbamoyl).

n and m are each independently 0-5.

In certain embodiments of Formula I, Ia, Ib, Ic, Id, Ie, or If, $X^2$ is O. In certain other embodiments, $X^2$ is S. In certain other embodiments, $X^2$ is $NR^5$.

In certain preferred embodiments of Formula I, Ia, Ib, Ic, Id, IIIa, IIIb, or IIIc, $R^5$ is H. In other embodiments, $R^5$ is alkyl (e.g., methyl or ethyl).

In certain embodiments of Formula I, Ia, Ib, Ic, Id, IIIa, IIIb, or IIIc, $X^2$ and $R^3$ combine to form a heterocyclyl (e.g., morpholinyl).

In certain embodiments of Formula I, Ia, Ib, Ic, Id, IIIa, IIIb, or IIIc, $R^3$ is H. In other embodiments, $R^3$ is alkyl (e.g., methyl, ethyl, isopropyl, or tert-butyl) or alkyloxy (e.g., methoxy). In certain preferred embodiments, $R^3$ is alkyl (e.g., methyl, ethyl, isopropyl, or tert-butyl). In certain more preferred embodiments, $R^3$ is methyl or ethyl.

In certain embodiments of Formula I, Ia, Ib, Ic, Id, IIIa, IIIb, or IIIc, $R^3$ is alkyl substituted with at least one substituent selected from hydoxy, amido ($C(O)NH_2$ or C(O)NHalkyl), aralkyl (e.g., benzyl), or

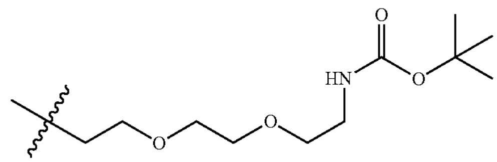

In certain preferred embodiments, $R^3$ is alkyl substituted with one substituent. In certain embodiments, $R^3$ is alkyl substituted with two substituents.

In certain embodiments of Formula I, Ia, Ib, Ic, Id, IIIb, or IIIc, the compound is represented by Formula IIa, IIb, IIc, or IId:

IIa

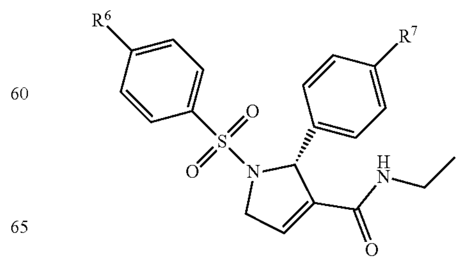

-continued

IIb

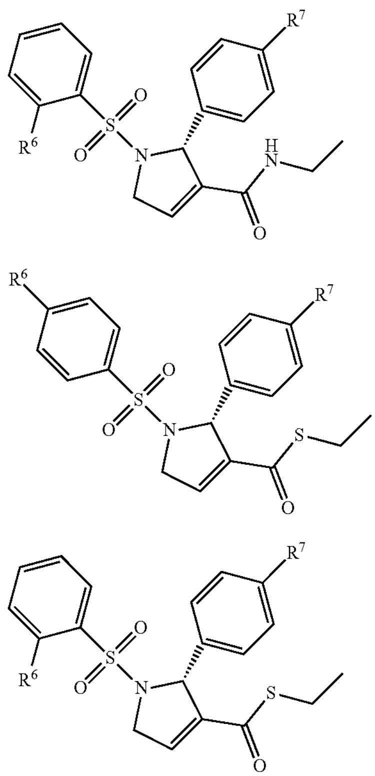

IIc

IId or a pharmaceutically acceptable salt thereof; wherein $R^6$ and $R^7$ are each, independently for each occurrence, selected from alkyl, halo, hydroxyl, carboxyl, acyl, ester, thioester, alkoxy, phosphoryl, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, aralkyl, carbamoyl, alkylcarbamoyl (e.g., N-methycarbamoyl or N,N-dimethylcarbamoyl).

In certain embodiments of Formula I, Ia, Ib, Ic, Id, IIIb, or IIIc, the compound is represented by Formula IIe, IIf, IIg, or IIh:

IIe

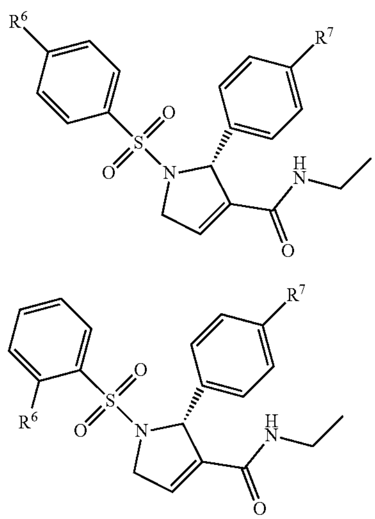

IIf

-continued

IIg

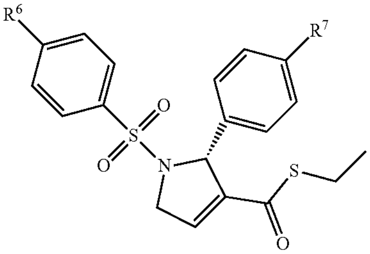

IIh

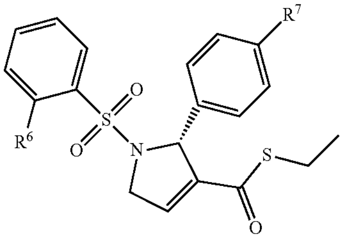

or a pharmaceutically acceptable salt thereof; wherein $R^6$ and $R^7$ are each, independently for each occurrence, selected from alkyl, halo, hydroxyl, carboxyl, acyl, ester, thioester, alkoxy, phosphoryl, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, aralkyl, carbamoyl, alkylcarbamoyl (e.g., N-methycarbamoyl or N,N-dimethylcarbamoyl).

In certain embodiments of Formula I, Ia, Ib, Ic, Id, IIa, IIb, IIc, IId, IIe, IIf, IIg, IIh, IIIa, IIIb, or IIIc, $R^6$ is halo (e.g., fluoro, chloro, or bromo), alkyl (e.g., methyl or fluoroalkyl), ester (e.g., methyl ester), or nitro. In certain preferred embodiments, $R^6$ is halo (e.g., fluoro, chloro, or bromo).

In certain embodiments of Formula I, Ia, Ib, Ic, Id, IIa, IIb, IIc, IId, IIe, IIf, IIg, IIh, IIIa, IIIb, or IIIc, $R^7$ is halo (e.g., fluoro, chloro, or bromo), alkyl (e.g., methyl or fluoroalkyl), ester (e.g., methyl ester), or nitro. In certain preferred embodiments, $R^7$ is halo (e.g., fluoro, chloro, or bromo).

In certain embodiments, the compound is selected from:

FS004

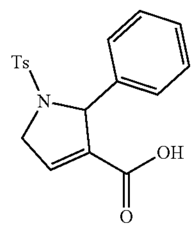

,

FS005

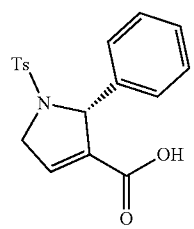

,

-continued
FS006
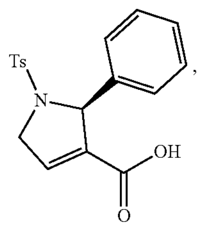
FS007
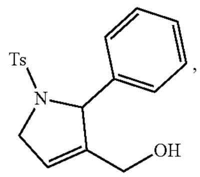
FS009
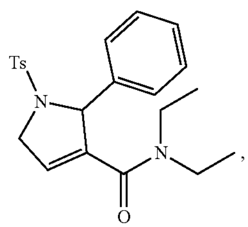
FS010
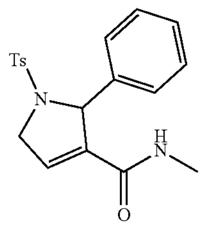
FS011
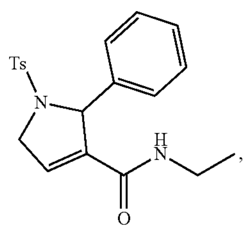
FS012
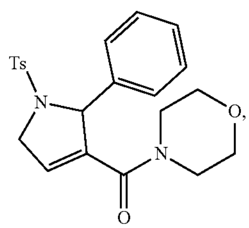
FS013
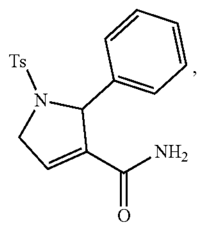
-continued
FS014
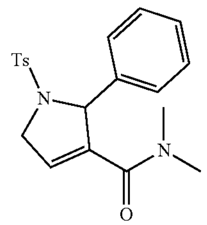
FS015
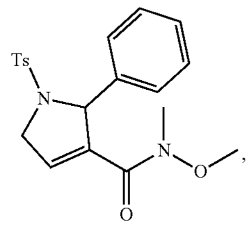
FS016
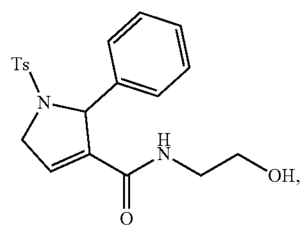
FS017
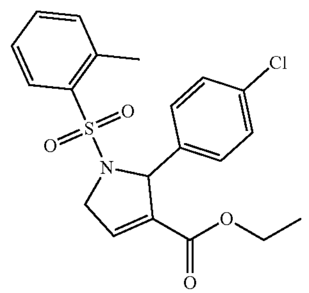
FS018
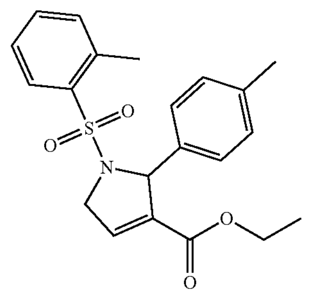
FS019
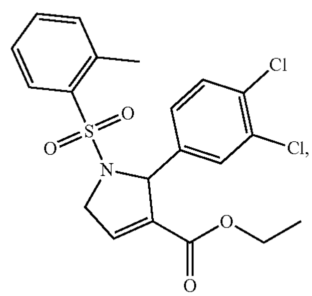

-continued
FS020
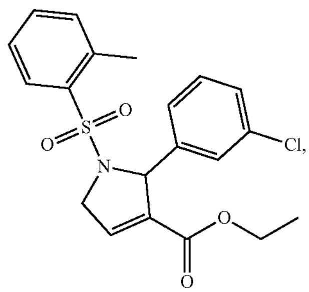
FS021
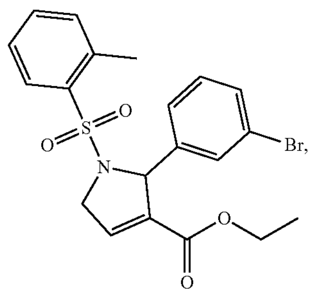
FS022
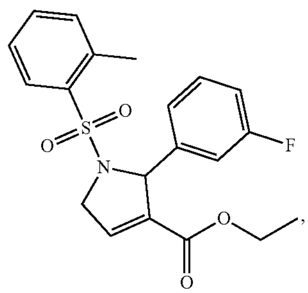
FS023
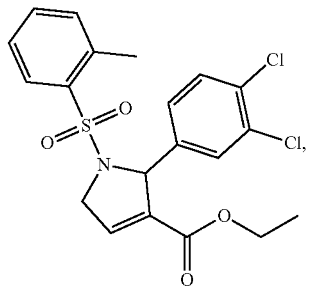
FS024
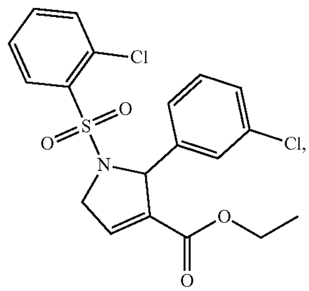
-continued
FS025
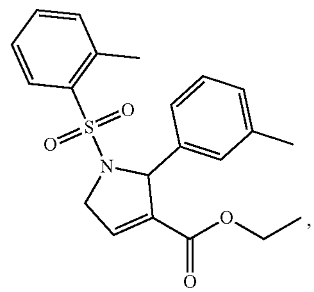
FS026
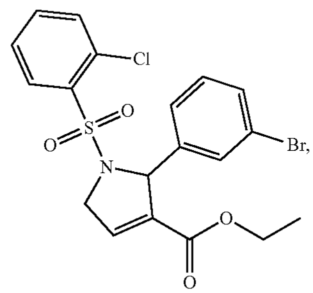
FS027
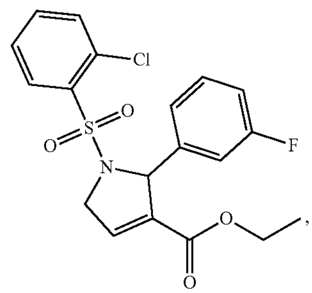
FS028
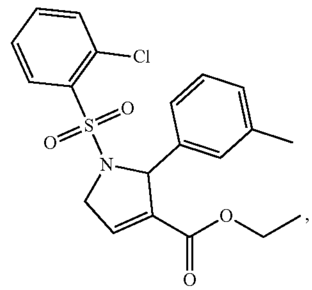
FS029
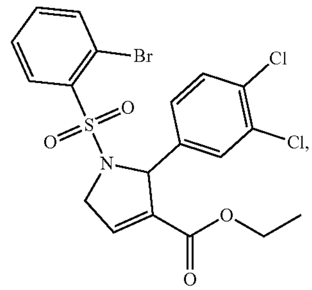

-continued
FS030
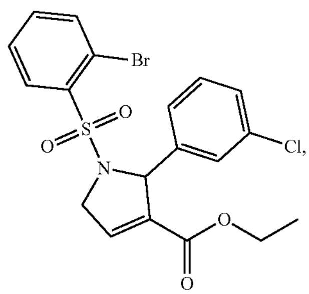
FS031
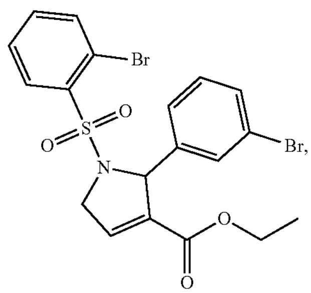
FS032
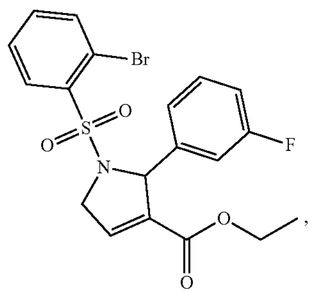
FS033
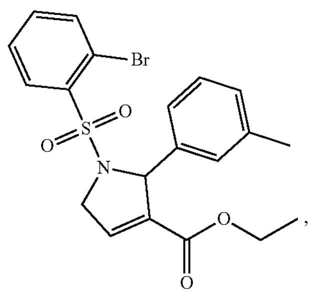
FS034
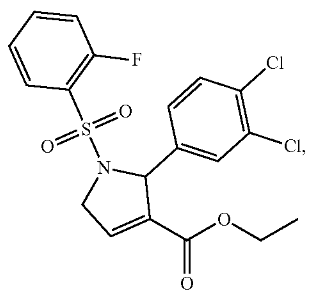
-continued
FS035
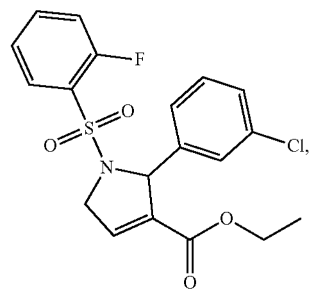
FS036
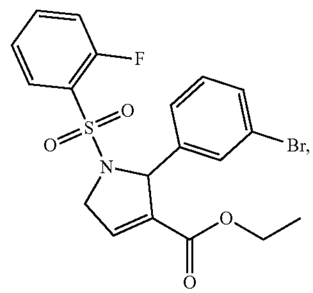
FS037
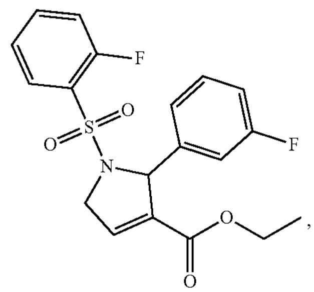
FS038
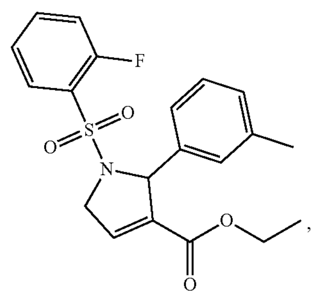
FS039
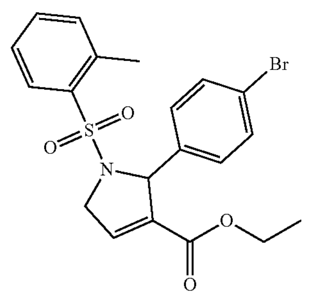

-continued
FS041
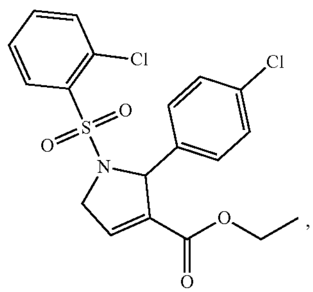
FS042
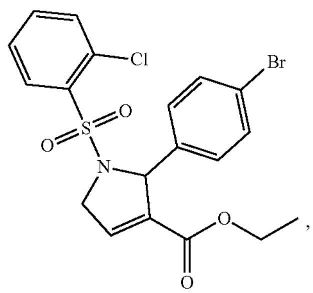
FS043
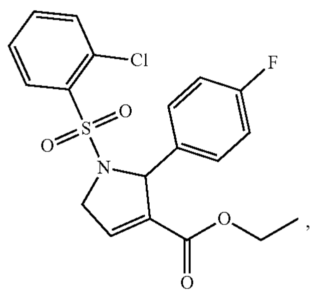
FS044
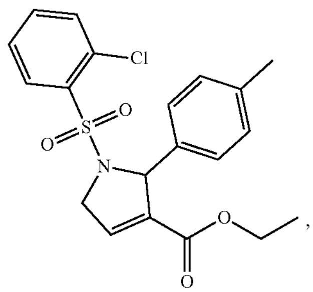
FS046
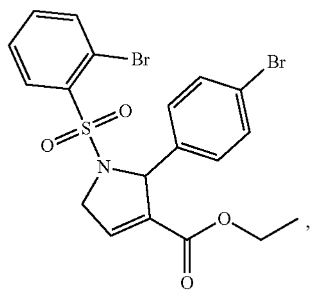
-continued
FS047
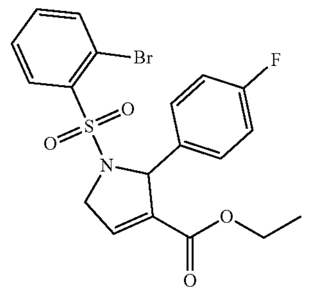
FS048
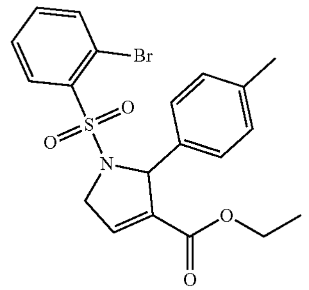
FS053
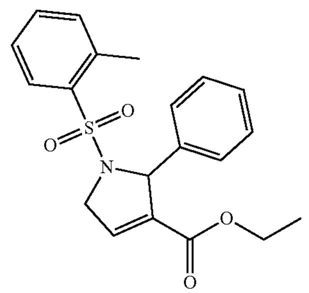
FS054
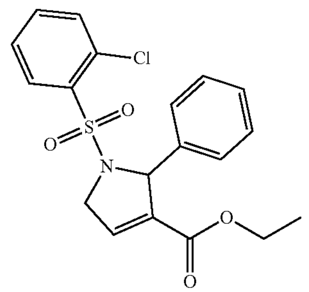
FS055
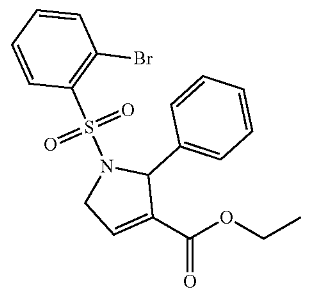

-continued
FS056
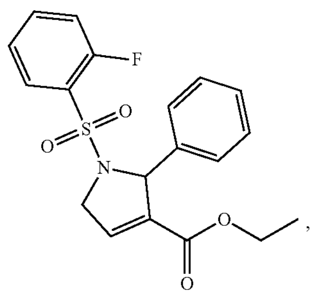
FS057
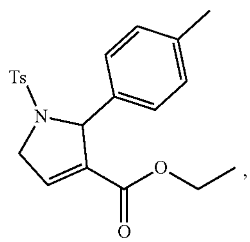
FS058
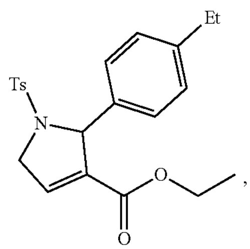
FS059
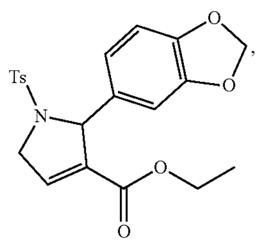
FS060
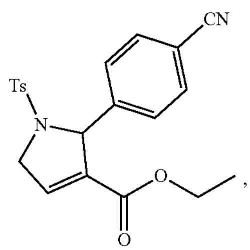
FS062
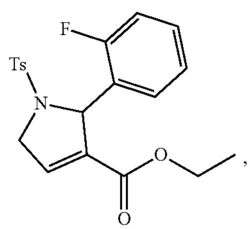
-continued
FS063
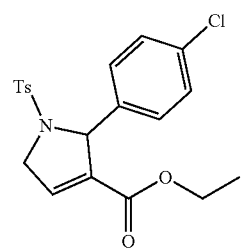
FS064
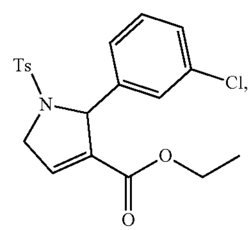
FS065
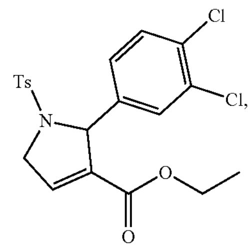
FS066
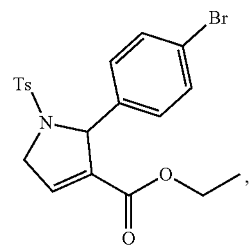
FS067
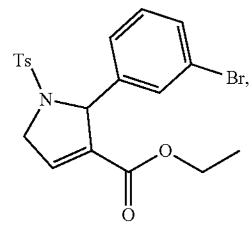
FS068
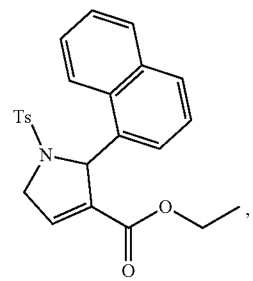

-continued
FS070
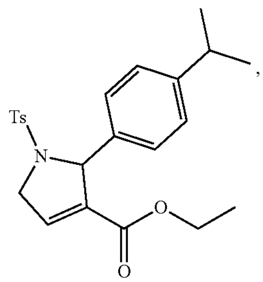
FS071
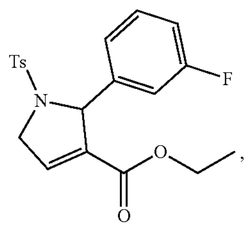
FS072
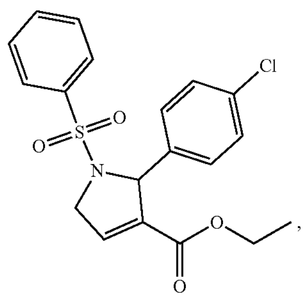
FS073
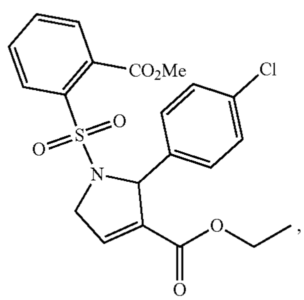
FS075
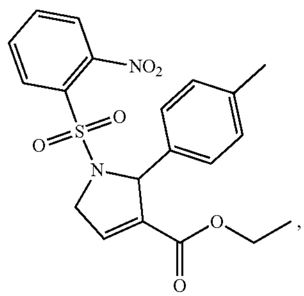
-continued
FS076
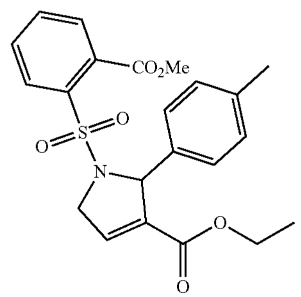
FS077
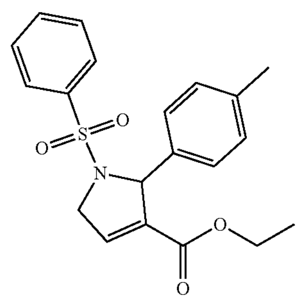
FS078
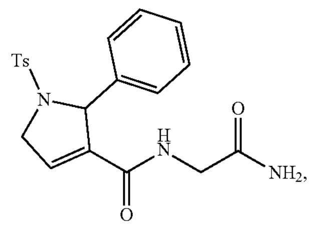
FS079
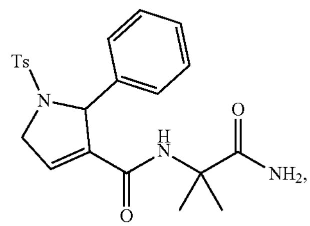
FS080
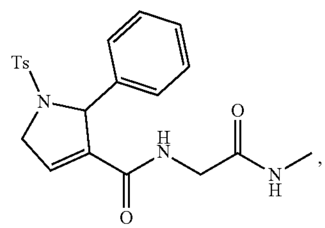
FS081
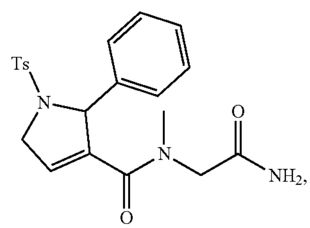

-continued
FS082
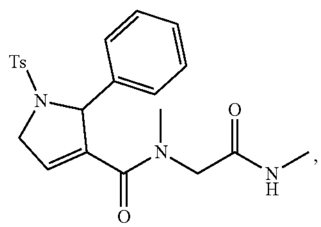
FS083
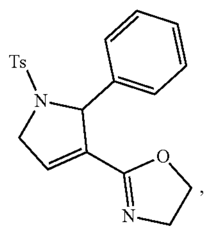
FS084
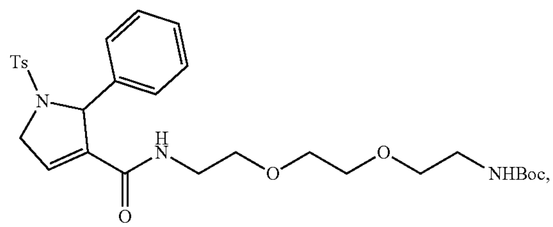
FS085
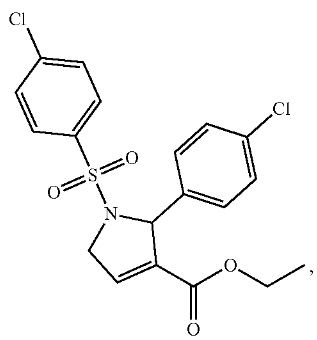
FS086
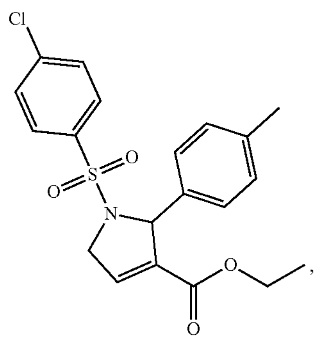
-continued
FS087
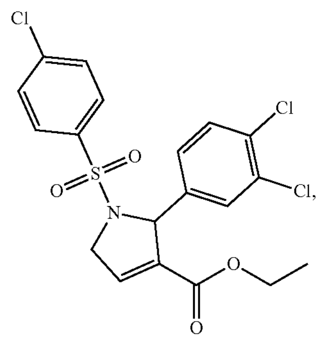
FS088
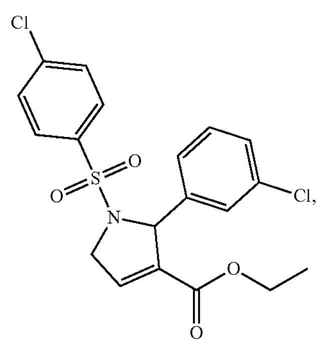
FS089
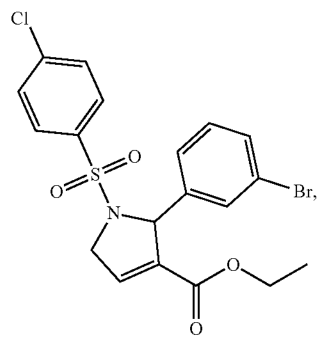
FS090
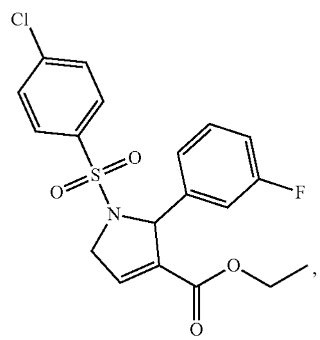

-continued
FS091
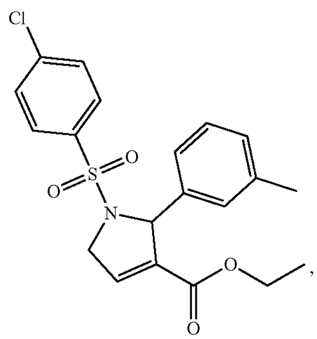
FS092
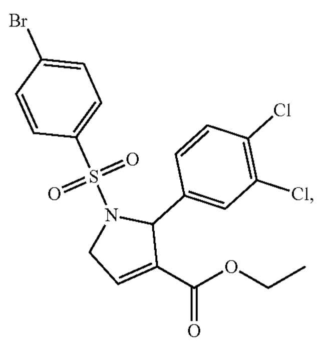
FS093
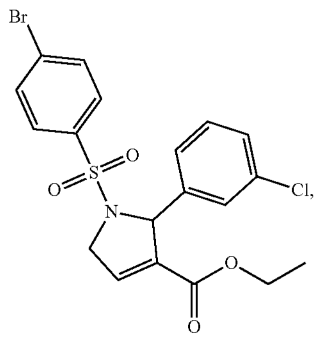
FS094
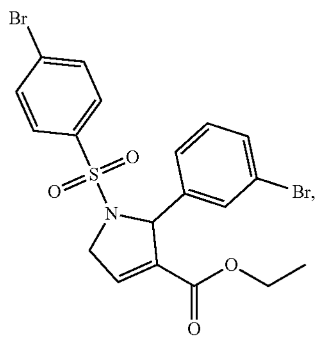
-continued
FS095
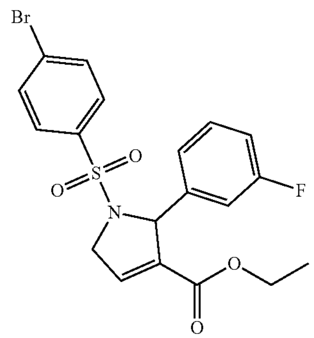
FS096
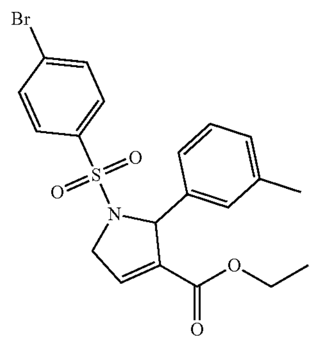
FS098
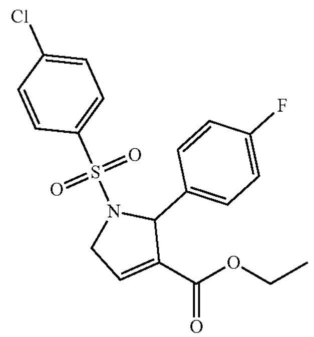
FS099
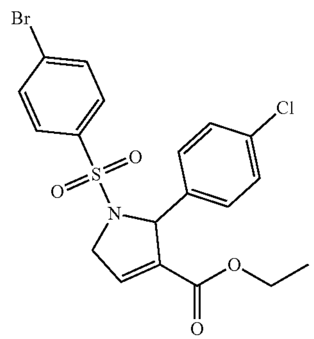

-continued
FS100
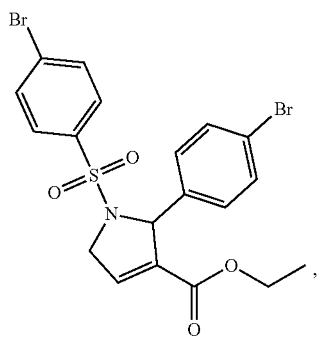
FS101
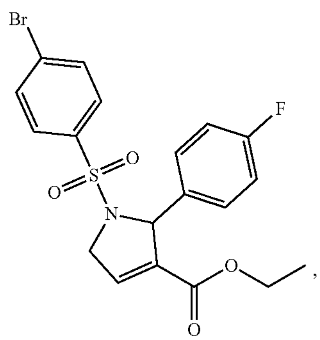
FS102
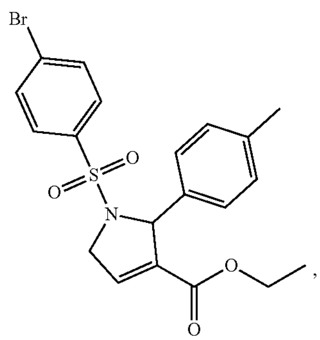
FS104
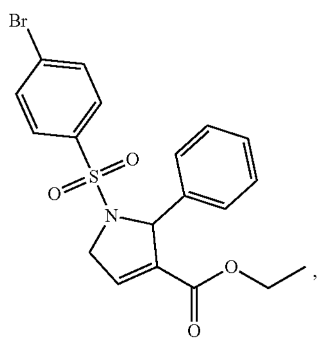
FS105
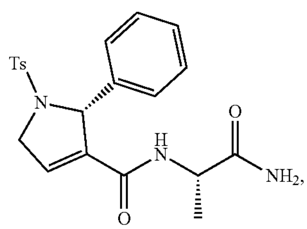
-continued
FS106
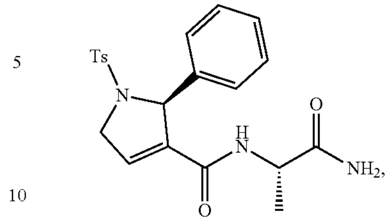
FS107
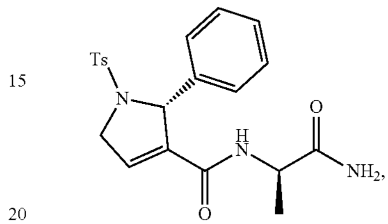
FS108
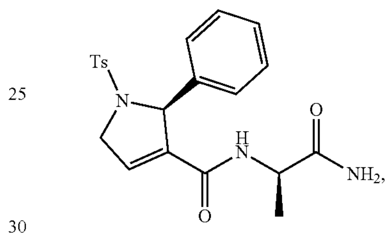
FS109
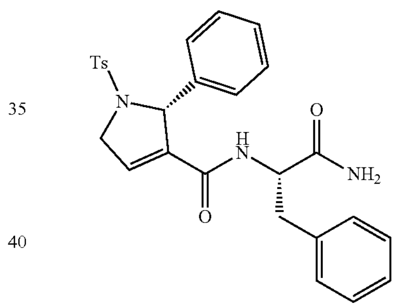
FS110
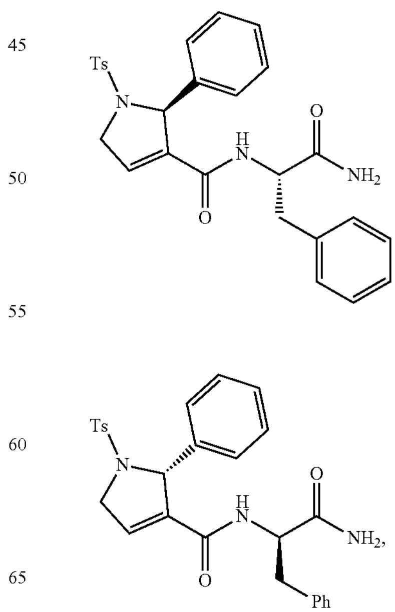
FS111

-continued
FS112
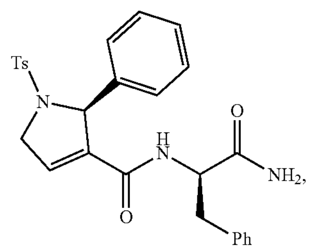
FS114
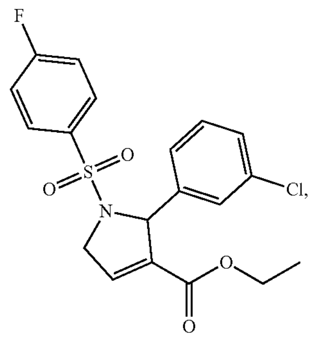
FS115
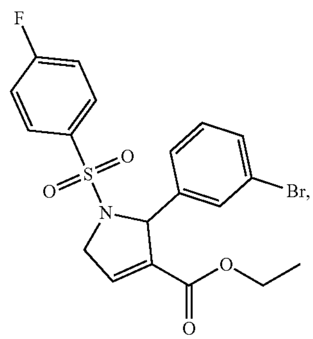
FS116
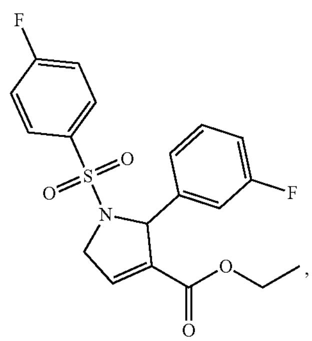
FS118
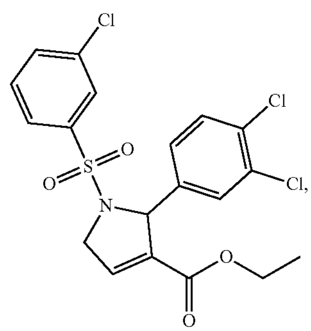
-continued
FS120
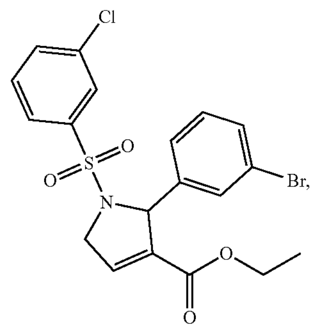
FS121
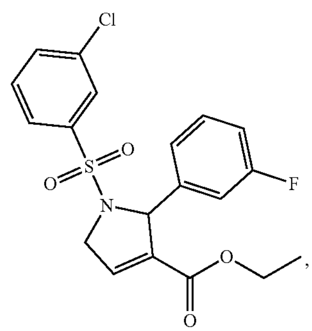
FS122
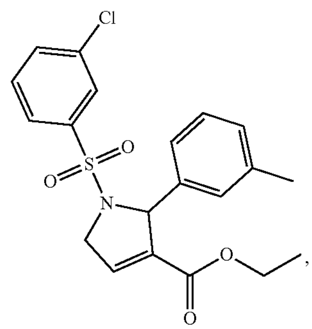
FS123
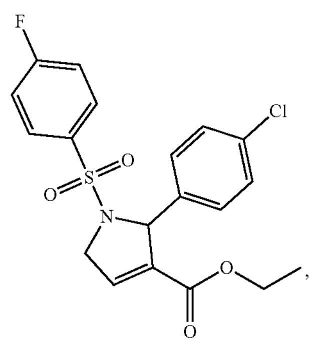

-continued
FS124
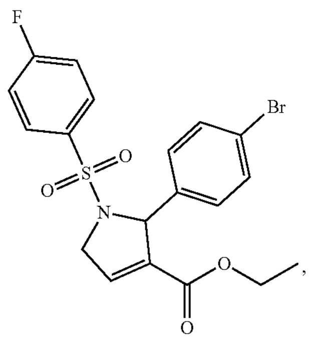
FS132
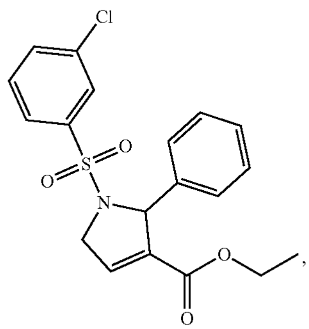
FS133
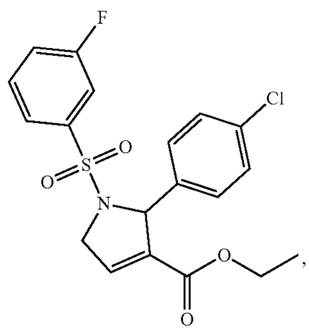
FS134
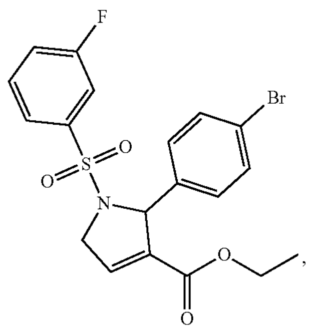
FS136
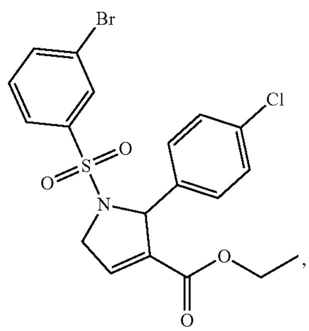
-continued
FS137
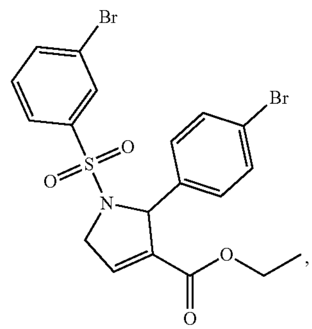
FS138
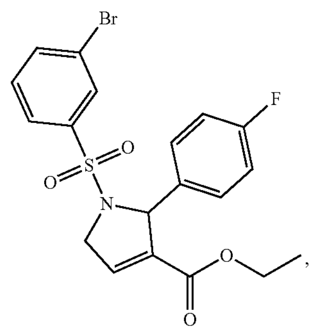
FS139
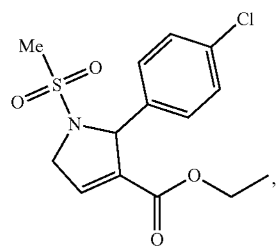
FS140
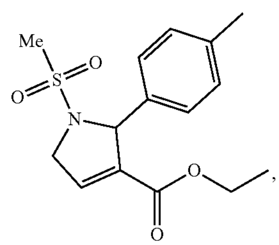
FS141
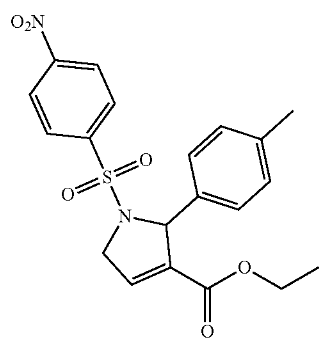

-continued
FS142
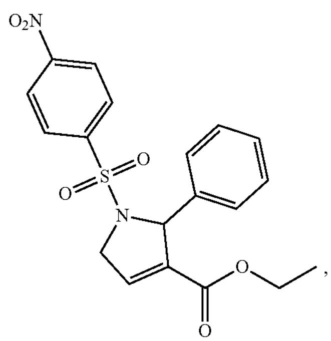
FS143
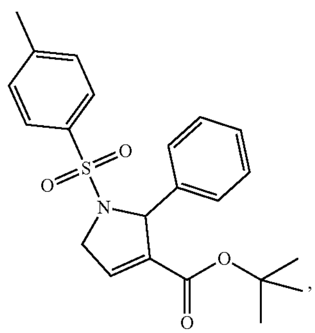
FS144
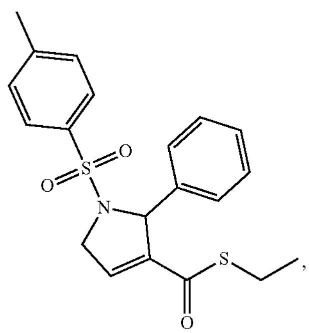
FS145
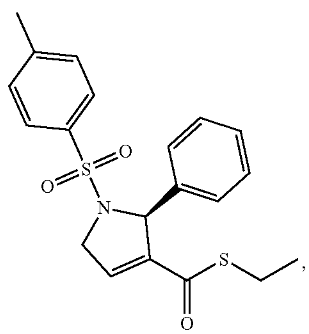
-continued
FS146
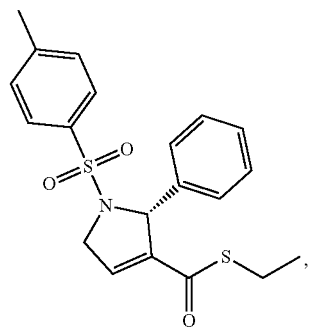
FS147
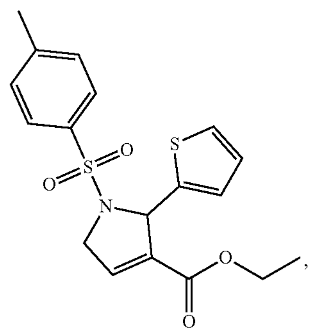
FS148
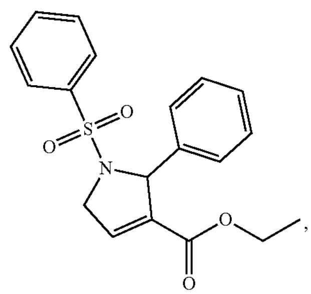
FS149
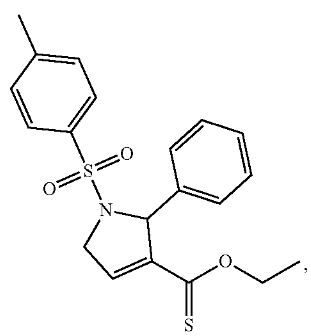
FS150
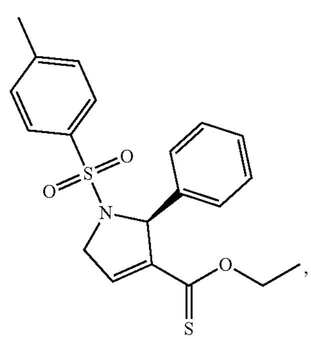

-continued
FS151
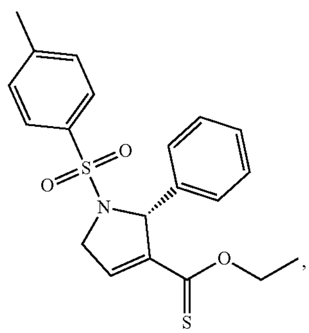
FS152
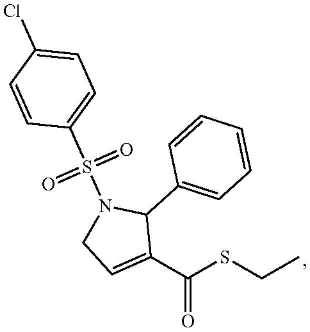
FS153
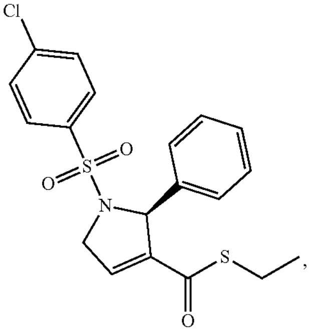
FS154
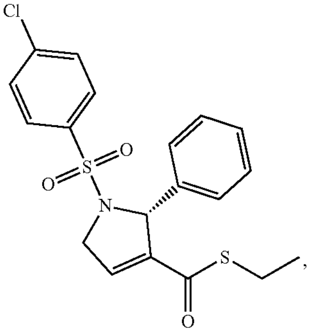
-continued
FS155
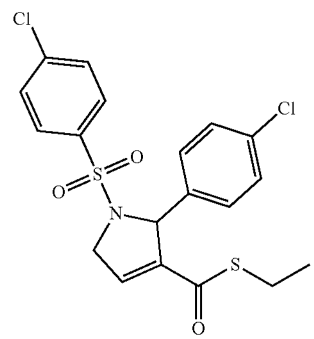
FS156
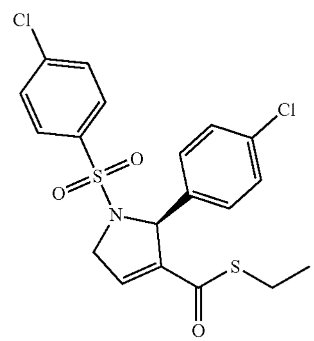
FS157
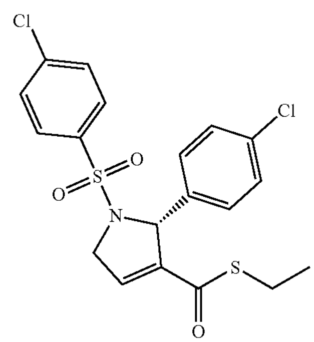
FS158
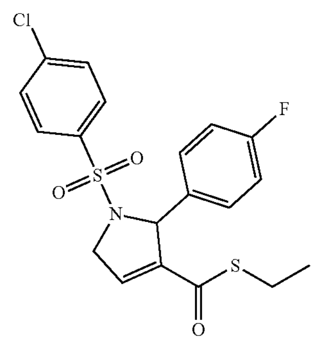

-continued
FS159
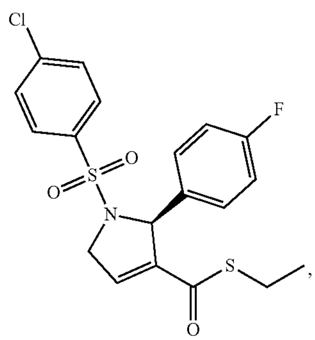
FS160
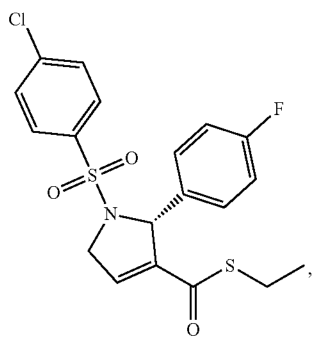
FS161
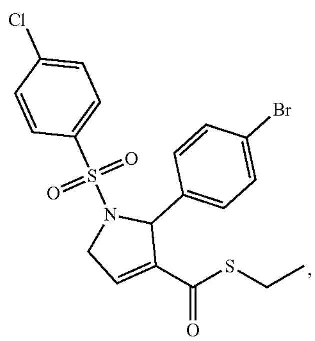
FS162
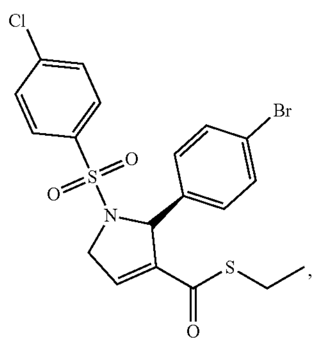
-continued
FS163
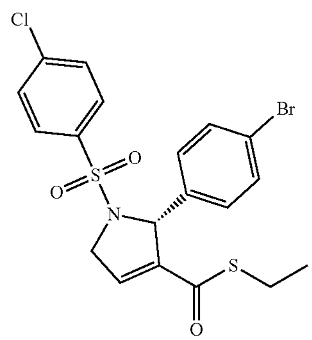
FS164
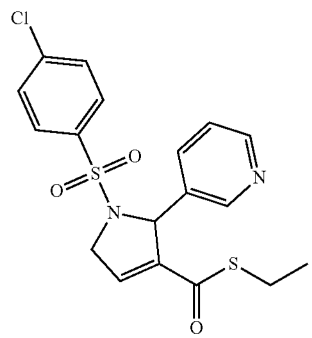
FS165
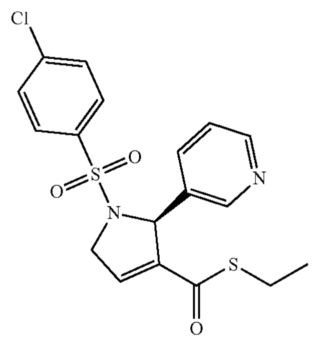
FS166
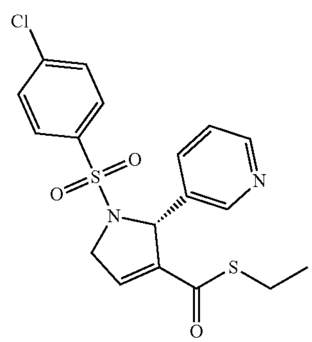

-continued
FS167
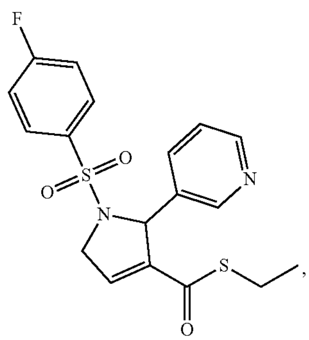
FS168
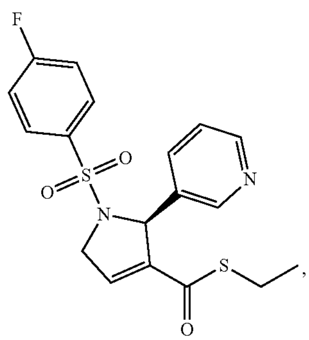
FS169
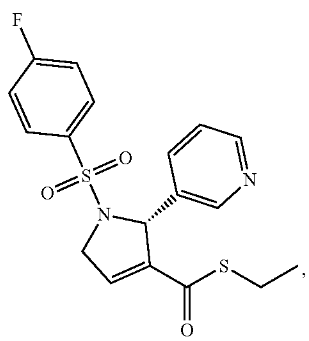
FS170
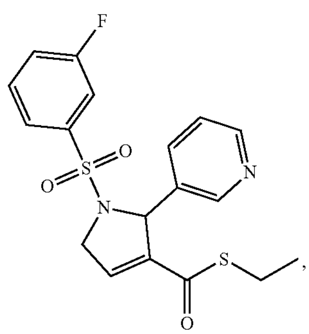
-continued
FS171
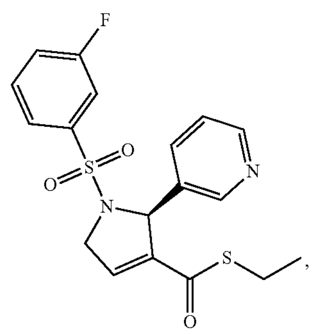
FS172
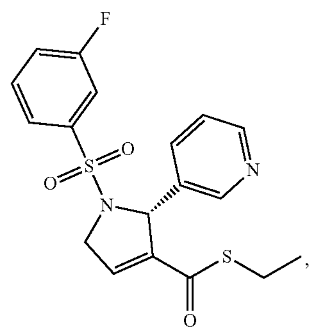
FS173
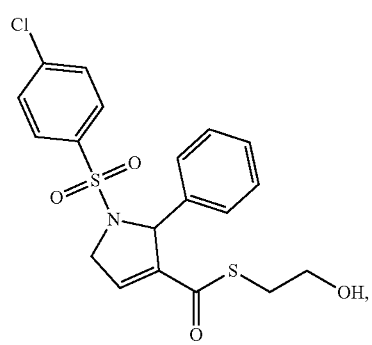
FS174
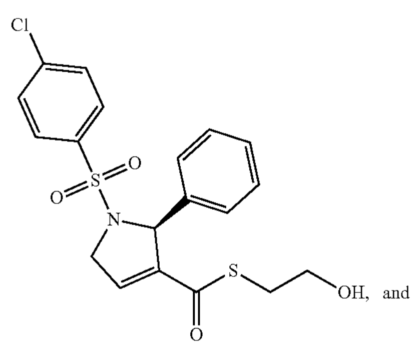
and -continued

FS175

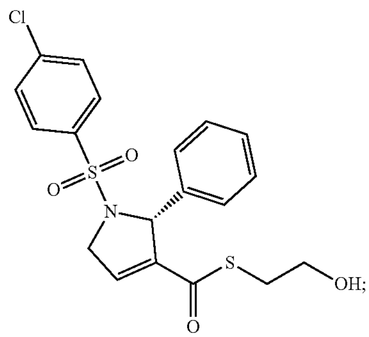

or a pharmaceutically acceptable salt thereof.

In some embodiments, the present disclosure provides compounds represented by Formula I':

I'

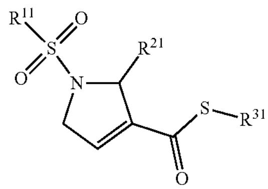

or a pharmaceutically acceptable salt thereof wherein $R^{11}$ is $C_1$-$C_6$alkyl, $C_3$-$C_6$cycloalkyl, or $C_6$-$C_{10}$aryl, wherein the $C_1$-$C_6$alkyl, $C_3$-$C_6$cycloalkyl, or $C_6$-$C_{10}$aryl are unsubstituted or substituted by 1, 2, 3, or 4 $R^{41}$;

$R^{21}$ is $C_6$-$C_{10}$aryl or $C_2$-$C_9$heteroaryl, wherein the $C_6$-$C_{10}$aryl or $C_2$-$C_9$heteroaryl are unsubstituted or substituted by 1, 2, 3, or 4 $R^{51}$;

$R^{31}$ is H or $C_1$-$C_6$alkyl that is unsubstituted or substituted by 1, 2, or 3 $R^{61}$;

each $R^{41}$ is independently selected from halogen, $C_1$-$C_6$alkyl, $C_1$-$C_6$haloalkyl, $C_3$-$C_6$cycloalkyl, $C_2$-$C_9$heterocycloalkyl, $C_2$-$C_9$heteroaryl, $C_6$-$C_{10}$aryl, oxo, —N($R^{71}$)$_2$, —CN, —C(═O)$R^{81}$, —C(═O)O$R^{71}$, —C(═O)N($R^{71}$)$_2$, —N$R^7$C(═O)$R^{81}$, —N$R^{71}$S(═O)$_2R^{81}$, —S(═O)$_2R^{81}$, and —S(═O)$_2$N($R^{71}$)$_2$;

each $R^{51}$ is independently selected from halogen, $C_1$-$C_6$alkyl, $C_1$-$C_6$haloalkyl, $C_3$-$C_6$cycloalkyl, $C_2$-$C_9$heterocycloalkyl, $C_2$-$C_9$heteroaryl, $C_6$-$C_{10}$aryl, oxo, —O$R^{71}$, —N($R^{71}$)$_2$, —CN, —C(═O)$R^{81}$, —C(═O)O$R^{71}$, —C(═O)N($R^{71}$)$_2$, —N$R^{71}$C(═O)$R^{81}$, —N$R^{71}$S(═O)$_2R^{81}$, —S(═O)$_2R^{81}$, and —S(═O)$_2$N($R^{71}$)$_2$;

each $R^{61}$ is independently selected from halogen, $C_1$-$C_6$alkyl, $C_1$-$C_6$haloalkyl, $C_3$-$C_6$cycloalkyl, $C_2$-$C_9$heterocycloalkyl, $C_2$-$C_9$heteroaryl, $C_6$-$C_{10}$aryl, oxo, —O$R^{71}$, —N($R^{71}$)$_2$, —CN, —C(═O)$R^{81}$, —C(═O)O$R^{71}$, —C(═O)N($R^{71}$)$_2$, —N$R^7$C(═O)$R^{81}$, —N$R^{71}$S(═O)$_2R^{81}$, —S(═O)$_2R^{81}$, and —S(═O)$_2$N($R^{71}$)$_2$;

each $R^{71}$ is independently selected from hydrogen, $C_1$-$C_6$alkyl, $C_3$-$C_6$cycloalkyl, $C_2$-$C_9$heterocycloalkyl, $C_2$-$C_9$heteroaryl, and phenyl, wherein $C_1$-$C_6$alkyl, $C_3$-$C_6$cycloalkyl, $C_2$-$C_9$heterocycloalkyl, $C_2$-$C_9$heteroaryl, and phenyl are unsubstituted or substituted with 1, 2, or 3 groups selected from halogen, $C_1$-$C_6$alkyl, $C_1$-$C_6$haloalkyl, $C_1$-$C_6$alkoxy, $C_1$-$C_6$haloalkoxy, $C_2$-$C_9$heterocycloalkyl, $C_2$-$C_9$heteroaryl, —O$R^{91}$, —N($R^{91}$)$_2$, —C(═O)O$R^{91}$, and —C(═O)N($R^{91}$)$_2$;

each $R^{81}$ is independently selected from $C_1$-$C_6$alkyl; and each $R^{91}$ is independently selected from hydrogen, $C_1$-$C_6$alkyl, and $C_1$-$C_6$haloalkyl.

In some embodiments, the compound is a compound of Formula I', wherein R', wherein $R^{11}$ is $C_6$-$C_{10}$aryl that is unsubstituted or substituted by 1, 2, 3, or 4 $R^{41}$. In some embodiments, the compound is a compound of Formula I', wherein $R^{11}$ is phenyl that is unsubstituted or substituted by 1, 2, 3, or 4 $R^{41}$. In some embodiments, the compound is a compound of Formula I', wherein $R^{11}$ is phenyl that is unsubstituted or substituted by 1, 2, or 3 $R^{41}$. In some embodiments, the compound is a compound of Formula I', wherein $R^{11}$ is phenyl that is unsubstituted or substituted by 1, 2, or 3 $R^{41}$ and each $R^{41}$ is independently selected from halogen, $C_1$-$C_6$alkyl, $C_1$-$C_6$haloalkyl, $C_3$-$C_6$cycloalkyl, $C_2$-$C_9$heterocycloalkyl, —O$R^{71}$, —N($R^{71}$)$_2$, —CN, —C(═O)$R^{81}$, —C(═O)O$R^{71}$, —C(═O)N($R^{71}$)$_2$, —S(═O)$_2R^{81}$, and —S(═O)$_2$N($R^{71}$)$_2$. In some embodiments, the compound is a compound of Formula I', wherein $R^{11}$ is phenyl that is unsubstituted or substituted by 1, 2, or 3 $R^{41}$ and each $R^{41}$ is independently selected from halogen, $C_1$-$C_6$alkyl, $C_1$-$C_6$haloalkyl, —O$R^{71}$, and —C(═O)O$R^{71}$. In some embodiments, the compound is a compound of Formula I', wherein $R^{11}$ is phenyl that is unsubstituted or substituted by 1, 2, or 3 $R^{41}$, each $R^{41}$ is independently selected from halogen, $C_1$-$C_6$alkyl, $C_1$-$C_6$haloalkyl, —O$R^{71}$, and —C(═O)O$R^{71}$, and each $R^{71}$ is independently selected from hydrogen and $C_1$-$C_6$alkyl. In some embodiments, the compound is a compound of Formula I', wherein $R^{11}$ is phenyl that is unsubstituted or substituted by 1 or 2 $R^{41}$, each $R^{41}$ is independently selected from halogen, $C_1$-$C_6$alkyl, $C_1$-$C_6$haloalkyl, —O$R^{71}$, and —C(═O)O$R^{71}$, and each $R^{71}$ is independently selected from hydrogen and $C_1$-$C_6$alkyl. In some embodiments, the compound is a compound of Formula I', wherein $R^{11}$ is phenyl that is unsubstituted or substituted by 1 or 2 $R^{41}$ and each $R^{41}$ is independently selected from halogen and $C_1$-$C_6$alkyl. In some embodiments, the compound is a compound of Formula I', wherein $R^{11}$ is phenyl substituted by 1 or 2 $R^{41}$ and each $R^{41}$ is independently selected from halogen and $C_1$-$C_6$alkyl. In some embodiments, the compound is a compound of Formula I', wherein $R^{11}$ is phenyl substituted by 2 $R^{41}$ and each $R^{41}$ is independently selected from halogen and $C_1$-$C_6$alkyl. In some embodiments, the compound is a compound of Formula I', wherein $R^{11}$ is phenyl substituted by 1 $R^{41}$ and $R^{41}$ is selected from halogen and $C_1$-$C_6$alkyl. In some embodiments, the compound is a compound of Formula I', wherein $R^{11}$ is phenyl substituted by 1 $R^{41}$ and $R^{41}$ is halogen. In some embodiments, the compound is a compound of Formula I', wherein $R^{11}$ is phenyl substituted by 1 $R^{41}$ and $R^{14}$ is $C_1$-$C_6$alkyl. In some embodiments, the compound is a compound of Formula I', wherein $R^{11}$ is unsubstituted phenyl. In some embodiments, the compound is a compound of Formula I', wherein $R^{11}$ is selected from:

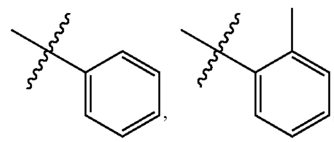

, ,

-continued

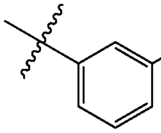, 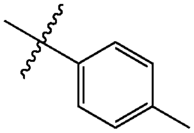,

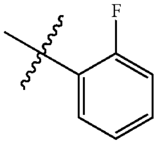, 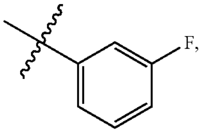

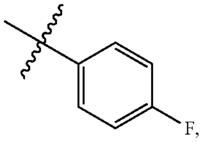 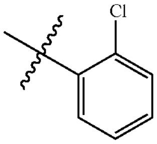,

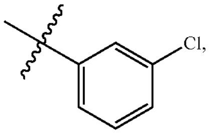 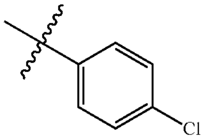,

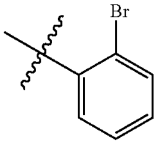, 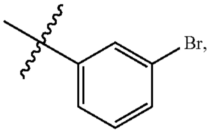

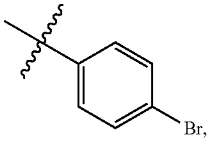 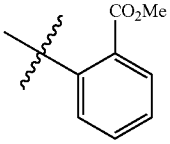,

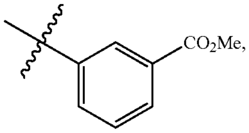 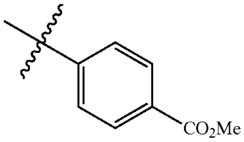,

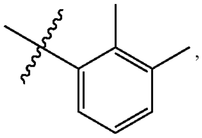, 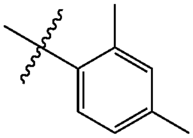,

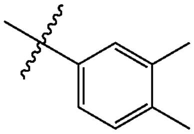, 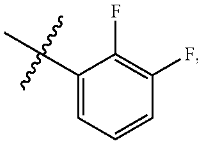

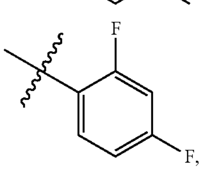 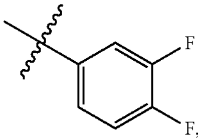

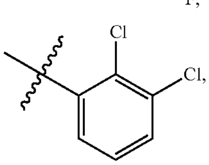 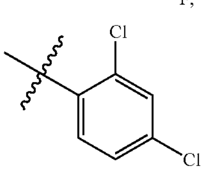,

-continued

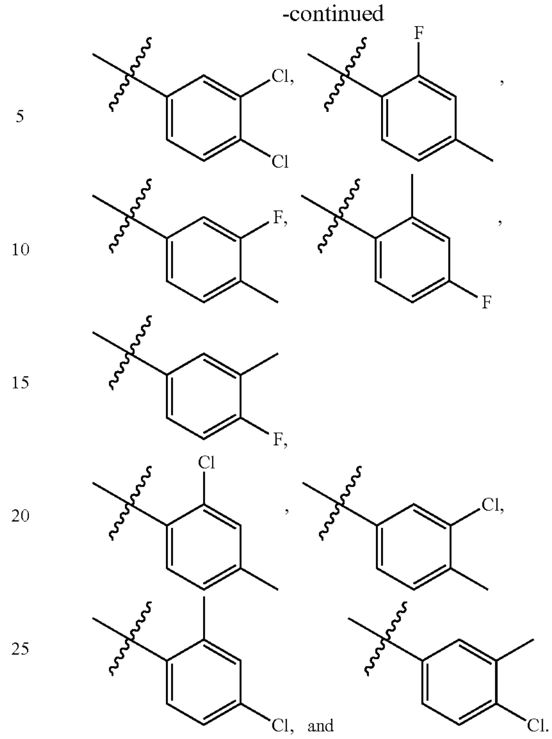

In some embodiments, the compound is a compound of Formula I', wherein $R^{11}$ is $C_1$-$C_6$alkyl that is unsubstituted or substituted by 1, 2, 3, or 4 $R^{41}$. In some embodiments, the compound is a compound of Formula I', wherein $R^{11}$ is $C_1$-$C_6$alkyl that is unsubstituted or substituted by 1, 2, or 3 $R^{41}$. In some embodiments, the compound is a compound of Formula I', wherein $R^{11}$ is $C_1$-$C_6$alkyl that is unsubstituted or substituted by 1, 2, or 3 $R^{41}$ and each $R^{41}$ is independently selected from halogen, $C_3$-$C_6$cycloalkyl, $C_2$-$C_9$heterocycloalkyl, —$OR^{71}$, —$N(R^{71})_2$, —CN, —C(═O)$R^{81}$, —C(═O)$OR^{71}$, —C(═O)$N(R^{71})_2$, —$S(═O)_2R^{81}$, and —$S(═O)_2N(R^{71})_2$. In some embodiments, the compound is a compound of Formula I', wherein $R^{11}$ is $C_1$-$C_6$alkyl that is unsubstituted or substituted by 1, 2, or 3 $R^{41}$, each $R^{41}$ is independently selected from halogen, —$OR^{71}$, and —C(═O)$OR^{71}$, and each $R^{71}$ is independently selected from hydrogen and $C_1$-$C_6$alkyl.

In some embodiments, the compound is a compound of Formula I', wherein $R^{11}$ is $C_3$-$C_6$cycloalkyl that is unsubstituted or substituted by 1, 2, 3, or 4 $R^{41}$. In some embodiments, the compound is a compound of Formula I', wherein $R^{11}$ is $C_3$-$C_6$cycloalkyl that is unsubstituted or substituted by 1, 2, or 3 $R^{41}$. In some embodiments, the compound is a compound of Formula I', wherein $R^{11}$ is $C_3$-$C_6$cycloalkyl that is unsubstituted or substituted by 1, 2, or 3 $R^{41}$ and each $R^{41}$ is independently selected from halogen, $C_1$-$C_6$alkyl, $C_1$-$C_6$haloalkyl, $C_3$-$C_6$cycloalkyl, $C_2$-$C_9$heterocycloalkyl, —$OR^{71}$, —$N(R^{71})_2$, —CN, —C(═O)$R^{81}$, —C(═O)$OR^{71}$, —C(═O)$N(R^{71})_2$, —$S(═O)_2R^{81}$, and —$S(═O)_2N(R^{71})_2$. In some embodiments, the compound is a compound of Formula I', wherein $R^{11}$ is $C_3$-$C_6$cycloalkyl that is unsubstituted or substituted by 1, 2, or 3 $R^{41}$, each $R^{41}$ is independently selected from halogen, $C_1$-$C_6$alkyl, $C_1$-$C_6$haloalkyl, —$OR^{71}$, and —C(═O)$OR^{71}$, and each $R^{71}$ is independently selected from hydrogen and $C_1$-$C_6$alkyl.

In some embodiments, the compound is a compound of Formula I', wherein $R^{21}$ is $C_6$-$C_{10}$aryl that is unsubstituted or substituted by 1, 2, 3, or 4 $R^{51}$. In some embodiments, the compound is a compound of Formula I', wherein $R^{21}$ is phenyl that is unsubstituted or substituted by 1, 2, 3, or 4 $R^{51}$. In some embodiments, the compound is a compound of Formula I', wherein $R^{21}$ is phenyl that is unsubstituted or substituted by 1, 2, or 3 $R^{51}$. In some embodiments, the compound is a compound of Formula I', wherein $R^{21}$ is phenyl that is unsubstituted or substituted by 1, 2, or 3 $R^{51}$ and each $R^{51}$ is independently selected from halogen, $C_1$-$C_6$alkyl, $C_1$-$C_6$haloalkyl, $C_3$-$C_6$cycloalkyl, $C_2$-$C_9$heterocycloalkyl, —$OR^{71}$, —$N(R^{71})_2$, —CN, —C(=O)$R^{81}$, —C(=O)$OR^{71}$, —C(=O)$N(R^{71})_2$, —S(=O)$_2R^{81}$, and —S(=O)$_2N(R^{71})_2$. In some embodiments, the compound is a compound of Formula I', wherein $R^{21}$ is phenyl that is unsubstituted or substituted by 1, 2, or 3 $R^{51}$ and each $R^{51}$ is independently selected from halogen, $C_1$-$C_6$alkyl, and $C_1$-$C_6$haloalkyl. In some embodiments, the compound is a compound of Formula I', wherein $R^{21}$ is phenyl that is unsubstituted or substituted by 1 or 2 $R^{51}$ and each $R^{51}$ is independently selected from halogen, $C_1$-$C_6$alkyl, and $C_1$-$C_6$haloalkyl. In some embodiments, the compound is a compound of Formula I', wherein $R^{21}$ is phenyl that is unsubstituted or substituted by 1 or 2 $R^{51}$ and each $R^{51}$ is independently selected from halogen and $C_1$-$C_6$alkyl. In some embodiments, the compound is a compound of Formula I', wherein $R^{21}$ is phenyl substituted by 1 or 2 $R^{5l}$ and each $R^{51}$ is independently selected from halogen and $C_1$-$C_6$alkyl. In some embodiments, the compound is a compound of Formula I', wherein $R^{21}$ is phenyl substituted by 2 $R^{51}$ and each $R^{51}$ is independently selected from halogen and $C_1$-$C_6$alkyl. In some embodiments, the compound is a compound of Formula I', wherein $R^{21}$ is phenyl substituted by 1 $R^{51}$ and $R^{51}$ is selected from halogen and $C_1$-$C_6$alkyl. In some embodiments, the compound is a compound of Formula I', wherein $R^{21}$ is phenyl substituted by 1 $R^{51}$ and $R^{51}$ is halogen. In some embodiments, the compound is a compound of Formula I', wherein $R^{21}$ is phenyl substituted by 1 $R^{51}$ and $R^{51}$ is $C_1$-$C_6$alkyl. In some embodiments, the compound is a compound of Formula I', wherein $R^{21}$ is unsubstituted phenyl. In some embodiments, the compound is a compound of Formula I', wherein $R^{21}$ is selected from:

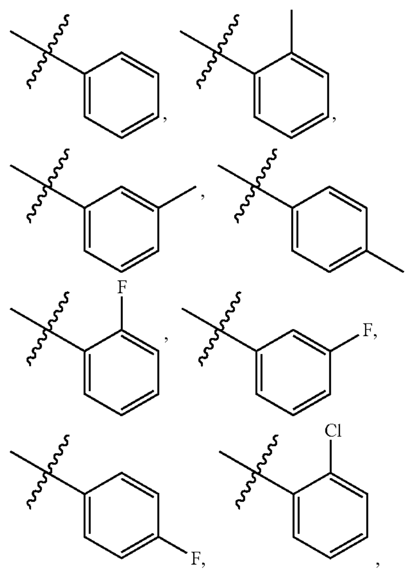

-continued

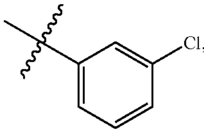 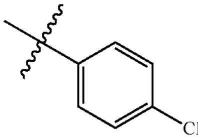 ,

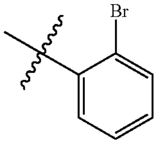 , 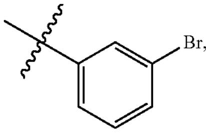

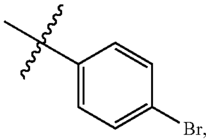

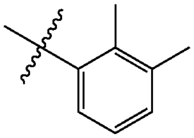 , 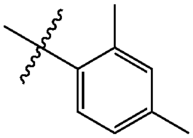 ,

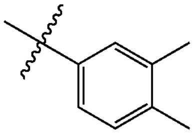 , 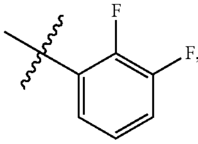

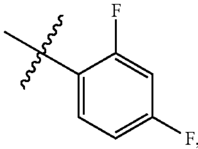 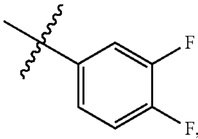

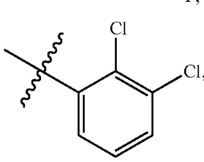 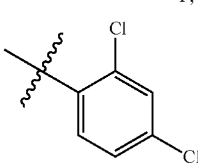 ,

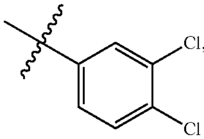 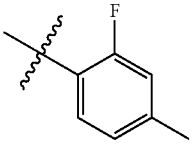 ,

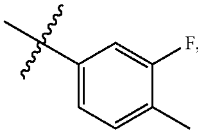 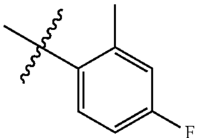 ,

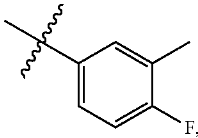

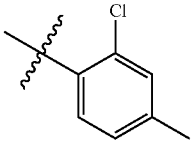 , 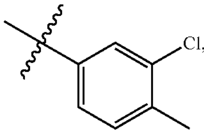

-continued

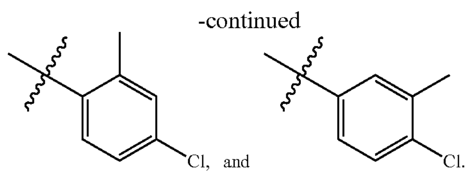

Cl, and Cl.

In some embodiments, the compound is a compound of Formula I', wherein $R^{21}$ is $C_2$-$C_9$heteroaryl that is unsubstituted or substituted by 1, 2, 3, or 4 $R^{51}$. In some embodiments, the compound is a compound of Formula I', wherein $R^{21}$ is pyridyl that is unsubstituted or substituted by 1, 2, 3, or 4 $R^{51}$. In some embodiments, the compound is a compound of Formula I', wherein $R^{21}$ is pyridyl that is unsubstituted or substituted by 1, 2, or 3 $R^{51}$. In some embodiments, the compound is a compound of Formula I' wherein $R^{21}$ is pyridyl that is unsubstituted or substituted by 1, 2, or 3 $R^{51}$ and each $R^{51}$ is independently selected from halogen, $C_1$-$C_6$alkyl, $C_1$-$C_6$haloalkyl, $C_3$-$C_6$cycloalkyl, $C_2$-$C_9$heterocycloalkyl, —$OR^{71}$, —$N(R^{71})_2$, —CN, —C(═O)$R^{81}$, —C(═O)$OR^{71}$, —C(═O)$N(R^{71})_2$, —S(═O)$_2R^{81}$, and —S(═O)$_2N(R^{71})_2$. In some embodiments, the compound is a compound of Formula I', wherein $R^{21}$ is pyridyl that is unsubstituted or substituted by 1, 2, or 3 $R^{51}$ and each $R^{51}$ is independently selected from halogen, $C_1$-$C_6$alkyl, and $C_1$-$C_6$haloalkyl. In some embodiments, the compound is a compound of Formula I', wherein $R^{21}$ is pyridyl that is unsubstituted or substituted by 1 or 2 $R^{51}$ and each $R^{51}$ is independently selected from halogen, $C_1$-$C_6$alkyl, and $C_1$-$C_6$haloalkyl. In some embodiments, the compound is a compound of Formula I', wherein $R^{21}$ is pyridyl that is unsubstituted or substituted by 1 or 2 $R^{51}$ and each $R^{51}$ is independently selected from halogen and $C_1$-$C_6$alkyl. In some embodiments, the compound is a compound of Formula I', wherein $R^{21}$ is pyridyl substituted by 1 or 2 $R^{51}$ and each $R^{51}$ is independently selected from halogen and $C_1$-$C_6$alkyl. In some embodiments, the compound is a compound of Formula I', wherein $R^{21}$ is pyridyl substituted by 2 $R^{51}$ and each $R^{51}$ is independently selected from halogen and $C_1$-$C_6$alkyl. In some embodiments, the compound is a compound of Formula I', wherein $R^{21}$ is pyridyl substituted by 1 $R^{51}$ and $R^{51}$ is selected from halogen and $C_1$-$C_6$alkyl. In some embodiments the compound is a compound of Formula I', wherein $R^{21}$ is pyridyl substituted by 1 $R^{51}$ and $R^{51}$ is halogen. In some embodiments, the compound is a compound of Formula I', wherein $R^{21}$ is pyridyl substituted by 1 $R^{51}$ and $R^{51}$ is $C_1$-$C_6$alkyl. In some embodiments, the compound is a compound of Formula I', wherein $R^{21}$ is unsubstituted pyridyl. In some embodiments, the compound is a compound of Formula I', wherein $R^{21}$ is selected from:

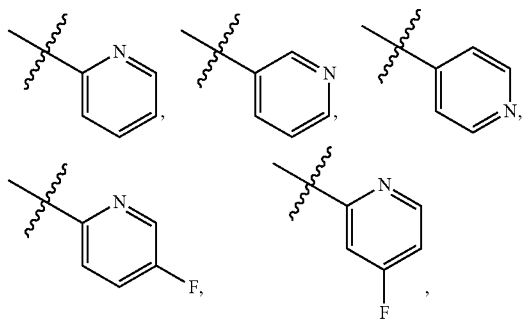

-continued

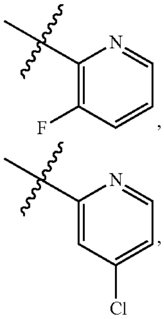

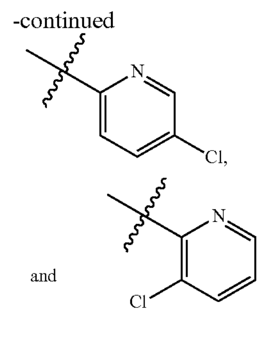

In some embodiments, the compound is a compound of Formula I', wherein $R^{31}$ is $C_1$-$C_6$alkyl that is unsubstituted or substituted by 1, 2, or 3 $R^{61}$. In some embodiments, the compound is a compound of Formula I', wherein $R^{31}$ is $C_1$-$C_6$alkyl that is unsubstituted or substituted by 1, 2, or 3 $R^{61}$ and each $R^{61}$ is independently selected from halogen, $C_3$-$C_6$cycloalkyl, $C_2$-$C_9$heterocycloalkyl, —$OR^{71}$, —$N(R^{71})_2$, —CN, —C(═O)$R^{81}$, —C(═O)$OR^{71}$, —C(═O)$N(R^{71})_2$, —S(═O)$_2R^{81}$, and —S(═O)$_2N(R^{71})_2$. In some embodiments, the compound is a compound of FormulaI', wherein $R^{31}$ is $C_1$-$C_6$alkyl that is unsubstituted or substituted by 1, 2, or 3 $R^{61}$, each $R^{61}$ is independently selected from halogen, —$OR^{71}$, and —C(═O)$OR^{71}$, and each $R^{71}$ is independently selected from hydrogen and $C_1$-$C_6$alkyl. In some embodiments, the compound is a compound of Formula I', wherein $R^{31}$ is unsubstituted $C_1$-$C_6$alkyl. In some embodiments, the compound is a compound of Formula I', wherein $R^{31}$ is —$CH_3$. In some embodiments, the compound is a compound of Formula I', wherein $R^{31}$ is —$CH_2CH_3$. In some embodiments, the compound is a compound of Formula I', wherein $R^{31}$ is H.

In some embodiments, the present disclosure provides compounds represented by Formula Ia':

Ia'

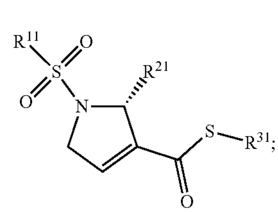

or a pharmaceutically acceptable salt thereof; wherein $R^{11}$ is $C_1$-$C_6$alkyl, $C_3$-$C_6$cycloalkyl, or $C_6$-$C_{10}$aryl, wherein the $C_1$-$C_6$alkyl, $C_3$-$C_6$cycloalkyl, or $C_6$-$C_{10}$aryl are unsubstituted or substituted by 1, 2, 3, or 4 $R^{41}$;

$R^{21}$ is $C_6$-$C_{10}$aryl or $C_2$-$C_9$heteroaryl, wherein $C_6$-$C_{10}$aryl or $C_2$-$C_9$heteroaryl are that is unsubstituted or substituted by 1, 2, 3, or 4 $R^{51}$;

$R^{31}$ is H or $C_1$-$C_6$alkyl that is unsubstituted or substituted by 1, 2, or 3 $R^{61}$;

each $R^{41}$ is independently selected from halogen, $C_1$-$C_6$alkyl, $C_1$-$C_6$haloalkyl, $C_3$-$C_6$cycloalkyl, $C_2$-$C_9$heterocycloalkyl, $C_2$-$C_9$heteroaryl, $C_6$-$C_{10}$aryl, oxo, —$OR^{71}$, —$N(R^{71})_2$, —CN, —C(═O)$R^{81}$, —C(═O)$OR^{71}$, —C(═O)$N(R^{71})_2$, —$NR^7$C(═O)$R^{81}$, —$NR^{71}$S(═O)$_2R^{81}$, —S(═O)$_2R^{81}$, and —S(═O)$_2$N$(R^{71})_2$;

each $R^{51}$ is independently selected from halogen, $C_1$-$C_6$alkyl, $C_1$-$C_6$haloalkyl, $C_3$-$C_6$cycloalkyl, $C_2$-$C_9$heterocycloalkyl, $C_2$-$C_9$heteroaryl, $C_6$-$C_{10}$aryl, oxo, —$OR^{71}$, —$N(R^{71})_2$, —CN, —C(═O)$R^{81}$, —C(═O)$OR^{71}$, —C(═O)$N(R^{71})_2$, —$NR^{71}$C(═O)$R^{81}$, —$NR^{71}S(═O)_2R^{81}$, —$S(═O)_2R^{81}$, and —$S(═O)_2N(R^{71})_2$;

each $R^{61}$ is independently selected from halogen, $C_1$-$C_6$alkyl, $C_1$-$C_6$haloalkyl, $C_3$-$C_6$cycloalkyl, $C_2$-$C_9$heterocycloalkyl, $C_2$-$C_9$heteroaryl, $C_6$-$C_{10}$aryl, oxo, —$OR^{71}$, —$N(R^{71})_2$, —CN, —C(═O)$R^{81}$, —C(═O)$OR^{71}$, —C(═O)$N(R^{71})_2$, —$NR^7$C(═O)$R^{81}$, —$NR^{71}S(═O)_2R^{81}$, —$S(═O)_2R^{81}$, and —$S(═O)_2N(R^{71})_2$;

each $R^{71}$ is independently selected from hydrogen, $C_1$-$C_6$alkyl, $C_3$-$C_6$cycloalkyl, $C_2$-$C_9$heterocycloalkyl, $C_2$-$C_9$heteroaryl, and phenyl, wherein $C_1$-$C_6$alkyl, $C_3$-$C_6$cycloalkyl, $C_2$-$C_9$heterocycloalkyl, $C_2$-$C_9$heteroaryl, and phenyl are unsubstituted or substituted with 1, 2, or 3 groups selected from halogen, $C_1$-$C_6$alkyl, $C_1$-$C_6$haloalkyl, $C_1$-$C_6$alkoxy, $C_1$-$C_6$haloalkoxy, $C_2$-$C_9$heterocycloalkyl, $C_2$-$C_9$heteroaryl, $C_2$-$C_9$heteroaryl, —$OR^{91}$, —$N(R^{91})_2$, —C(═O)$OR^{91}$, and —C(═O)$N(R^{91})_2$;

each $R^{81}$ is independently selected from $C_1$-$C_6$alkyl; and each $R^{91}$ is independently selected from hydrogen, $C_1$-$C_6$alkyl, and $C_1$-$C_6$haloalkyl.

In some embodiments, the compound is a compound of Formula Ia', wherein $R^{11}$ is $C_6$-$C_{10}$aryl that is unsubstituted or substituted by 1, 2, 3, or 4 $R^{41}$. In some embodiments, the compound is a compound of Formula Ia', wherein $R^{11}$ is phenyl that is unsubstituted or substituted by 1, 2, 3, or 4 $R^{41}$. In some embodiments, the compound is a compound of Formula Ia', wherein $R^{11}$ is phenyl that is unsubstituted or substituted by 1, 2, or 3 $R^{41}$. In some embodiments, the compound is a compound of Formula Ia', wherein $R^{11}$ is phenyl that is unsubstituted or substituted by 1, 2, or 3 $R^{41}$ and each $R^{41}$ is independently selected from halogen, $C_1$-$C_6$alkyl, $C_1$-$C_6$haloalkyl, $C_3$-$C_6$cycloalkyl, $C_2$-$C_9$heterocycloalkyl, —$OR^{71}$, —$N(R^{71})_2$, —CN, —C(═O)$R^{81}$, —C(═O)$OR^{71}$, —C(═O)$N(R^{71})_2$, —$S(═O)_2R^{81}$, and —$S(═O)_2N(R^{71})_2$. In some embodiments, the compound is a compound of Formula Ia', wherein $R^{11}$ is phenyl that is unsubstituted or substituted by 1, 2, or 3 $R^{41}$ and each $R^{41}$ is independently selected from halogen, $C_1$-$C_6$alkyl, $C_1$-$C_6$haloalkyl, —$OR^{71}$, and —C(═O)$OR^{71}$. In some embodiments, the compound is a compound of Formula Ia', wherein $R^{11}$ is phenyl that is unsubstituted or substituted by 1, 2, or 3 $R^{41}$, each $R^{41}$ is independently selected from halogen, $C_1$-$C_6$alkyl, $C_1$-$C_6$haloalkyl, —$OR^{71}$, and —C(═O)$OR^{71}$, and each $R^{71}$ is independently selected from hydrogen and $C_1$-$C_6$alkyl. In some embodiments, the compound is a compound of Formula Ia', wherein $R^{11}$ is phenyl that is unsubstituted or substituted by 1 or 2 $R^{41}$, each $R^{41}$ is independently selected from halogen, $C_1$-$C_6$alkyl, $C_1$-$C_6$haloalkyl, —$OR^{71}$, and —C(═O)$OR^{71}$, and each $R^{71}$ is independently selected from hydrogen and $C_1$-$C_6$alkyl. In some embodiments, the compound is a compound of Formula Ia', wherein $R^{11}$ is phenyl that is unsubstituted or substituted by 1 or 2 $R^{41}$ and each $R^{41}$ is independently selected from halogen and $C_1$-$C_6$alkyl. In some embodiments, the compound is a compound of Formula Ia', wherein $R^{11}$ is phenyl substituted by 1 or 2 $R^{41}$ and each $R^{41}$ is independently selected from halogen and $C_1$-$C_6$alkyl. In some embodiments, the compound is a compound of Formula Ia', wherein $R^{11}$ is phenyl substituted by 2 $R^{41}$ and each $R^{41}$ is independently selected from halogen and $C_1$-$C_6$alkyl. In some embodiments, the compound is a compound of Formula Ia', wherein $R^{11}$ is phenyl substituted by 1 $R^{41}$ and $R^{41}$ is selected from halogen and $C_1$-$C_6$alkyl. In some embodiments, the compound is a compound of Formula Ia', wherein $R^{11}$ is phenyl substituted by 1 $R^{41}$ and $R^{41}$ is halogen. In some embodiments, the compound is a compound of Formula Ia', wherein $R^{11}$ is phenyl substituted by 1 $R^{41}$ and $R^{41}$ is $C_1$-$C_6$alkyl. In some embodiments, the compound is a compound of Formula Ia', wherein $R^{11}$ is unsubstituted phenyl. In some embodiments, the compound is a compound of Formula Ia', wherein $R^{11}$ is selected from:

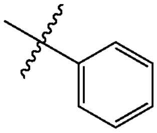,
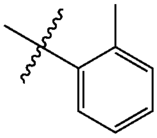,
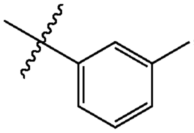,
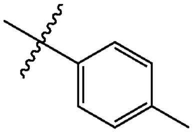,
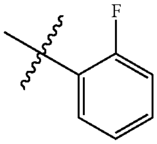,
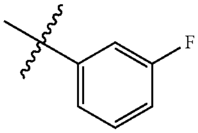,
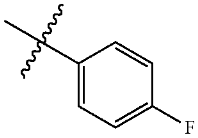,
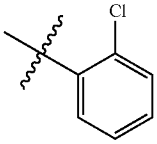,
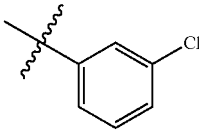,
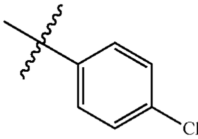,
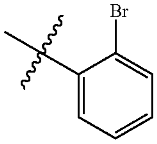,
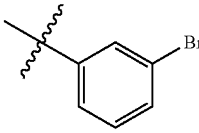,
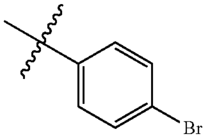,
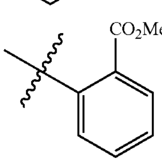,
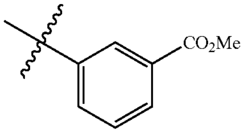,
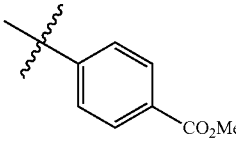,
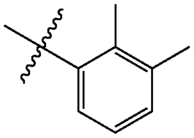,
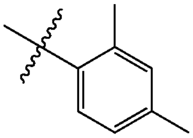, -continued

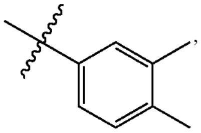,

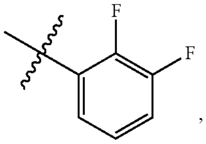, 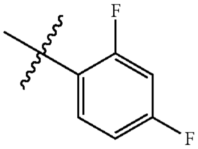,

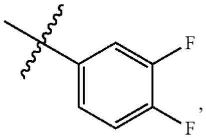, 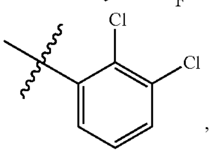,

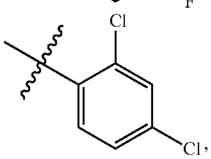, 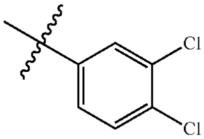,

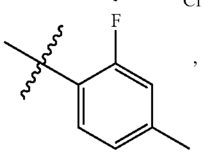, 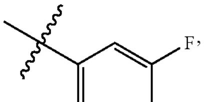,

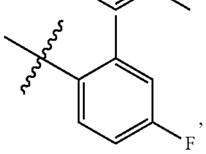, 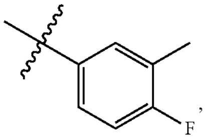,

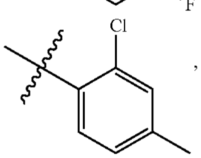, 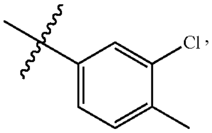,

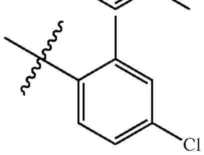, and 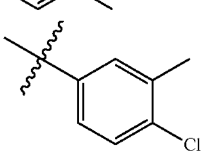.

In some embodiments, the compound is a compound of Formula Ia', wherein $R^{11}$ is $C_1$-$C_6$alkyl that is unsubstituted or substituted by 1, 2, 3, or 4 $R^{41}$. In some embodiments, the compound is a compound of Formula Ia', wherein $R^{11}$ is $C_1$-$C_6$alkyl that is unsubstituted or substituted by 1, 2, or 3 $R^{41}$. In some embodiments, the compound is a compound of Formula Ia', wherein $R^{11}$ is $C_1$-$C_6$alkyl that is unsubstituted or substituted by 1, 2, or 3 $R^{41}$ and each $R^{41}$ is independently selected from halogen, $C_3$-$C_6$cycloalkyl, $C_2$-$C_9$heterocycloalkyl, —$OR^{71}$, —$N(R^{71})_2$, —CN, —C(═O)$R^{81}$, —C(═O)$OR^{71}$, —C(═O)$N(R^{71})_2$, —S(═$O)_2R^{81}$, and —S(═$O)_2N(R^{71})_2$. In some embodiments, the compound is a compound of Formula Ia', wherein $R^{11}$ is $C_1$-$C_6$alkyl that is unsubstituted or substituted by 1, 2, or 3 $R^{41}$, each $R^{41}$ is independently selected from halogen, —$OR^{71}$, and —C(═O)$OR^{71}$, and each $R^{71}$ is independently selected from hydrogen and $C_1$-$C_6$alkyl.

In some embodiments, the compound is a compound of Formula Ia', wherein $R^{11}$ is $C_3$-$C_6$cycloalkyl that is unsubstituted or substituted by 1, 2, 3, or 4 $R^{41}$. In some embodiments, the compound is a compound of Formula Ia', wherein $R^{11}$ is $C_3$-$C_6$cycloalkyl that is unsubstituted or substituted by 1, 2, or 3 $R^{41}$. In some embodiments, the compound is a compound of Formula Ia', wherein $R^{11}$ is $C_3$-$C_6$cycloalkyl that is unsubstituted or substituted by 1, 2, or 3 $R^{41}$ and each $R^{41}$ is independently selected from halogen, $C_1$-$C_6$alkyl, $C_1$-$C_6$haloalkyl, $C_3$-$C_6$cycloalkyl, $C_2$-$C_9$heterocycloalkyl, —$OR^{71}$, —$N(R^{71})_2$, —CN, —C(═O)$R^{81}$, —C(═O)$OR^{71}$, —C(═O)$N(R^{71})_2$, —S(═$O)_2R^{81}$, and —S(═$O)_2N(R^{71})_2$. In some embodiments, the compound is a compound of Formula Ia', wherein $R^1$ is $C_3$-$C_6$cycloalkyl that is unsubstituted or substituted by 1, 2, or 3 $R^{41}$, each $R^{41}$ is independently selected from halogen, $C_1$-$C_6$alkyl, $C_1$-$C_6$haloalkyl, —$OR^{71}$, and —C(═O)$OR^{71}$, and each $R^{71}$ is independently selected from hydrogen and $C_1$-$C_6$alkyl.

In some embodiments, the compound is a compound of Formula Ia', wherein $R^{21}$ is $C_6$-$C_{10}$aryl that is unsubstituted or substituted by 1, 2, 3, or 4 $R^{51}$. In some embodiments, the compound is a compound of Formula Ia', wherein $R^{21}$ is phenyl that is unsubstituted or substituted by 1, 2, 3, or 4 $R^{51}$. In some embodiments, the compound is a compound of Formula Ia', wherein $R^{21}$ is phenyl that is unsubstituted or substituted by 1, 2, or 3 $R^{51}$. In some embodiments, the compound is a compound of Formula Ia', wherein $R^{21}$ is phenyl that is unsubstituted or substituted by 1, 2, or 3 $R^{51}$ and each $R^{51}$ is independently selected from halogen, $C_1$-$C_6$alkyl, $C_1$-$C_6$haloalkyl, $C_3$-$C_6$cycloalkyl, $C_2$-$C_9$heterocycloalkyl, —$OR^{71}$, —$N(R^{71})_2$, —CN, —C(═O)$R^{81}$, —C(═O)$OR^{71}$, —C(═O)$N(R^{71})_2$, —S(═$O)_2R^{81}$, and —S(═$O)_2N(R^{71})_2$. In some embodiments, the compound is a compound of Formula Ia', wherein $R^{21}$ is phenyl that is unsubstituted or substituted by 1, 2, or 3 $R^{51}$ and each $R^{51}$ is independently selected from halogen, $C_1$-$C_6$alkyl, and $C_1$-$C_6$haloalkyl. In some embodiments, the compound is a compound of Formula Ia', wherein $R^{21}$ is phenyl that is unsubstituted or substituted by 1 or 2 $R^{51}$ and each $R^{51}$ is independently selected from halogen, $C_1$-$C_6$alkyl, and $C_1$-$C_6$haloalkyl. In some embodiments, the compound is a compound of Formula Ia', wherein $R^{21}$ is phenyl that is unsubstituted or substituted by 1 or 2 $R^{51}$ and each $R^{51}$ is independently selected from halogen and $C_1$-$C_6$alkyl. In some embodiments, the compound is a compound of Formula Ia', wherein $R^{21}$ is phenyl substituted by 1 or 2 $R^{51}$ and each $R^{51}$ is independently selected from halogen and $C_1$-$C_6$alkyl. In some embodiments, the compound is a compound of Formula Ia', wherein $R^{21}$ is phenyl substituted by 2 $R^{51}$ and each $R^{51}$ is independently selected from halogen and $C_1$-$C_6$alkyl. In some embodiments, the compound is a compound of Formula Ia', wherein $R^{21}$ is phenyl substituted by 1 $R^{51}$ and $R^{51}$ is selected from halogen and $C_1$-$C_6$alkyl. In some embodiments, the compound is a compound of Formula Ia', wherein $R^{21}$ is phenyl substituted by 1 $R^{51}$ and $R^{51}$ is halogen. In some embodiments, the compound is a compound of Formula Ia', wherein $R^{21}$ is phenyl substituted by 1 $R^{51}$ and $R^{51}$ is $C_1$-$C_6$alkyl. In some embodiments, the compound is a compound of Formula Ia', wherein $R^{21}$ is unsubstituted phenyl. In some embodiments, the compound is a compound of Formula Ia', wherein $R^{21}$ is selected from:

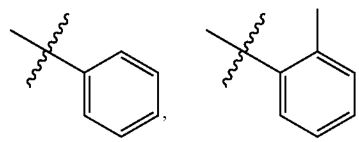

-continued

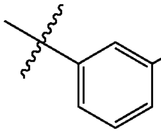, 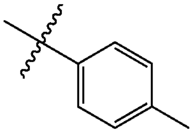,

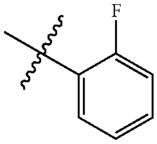, 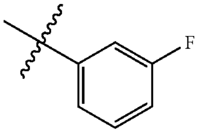,

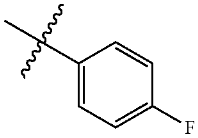, 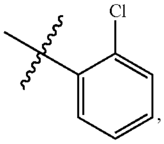,

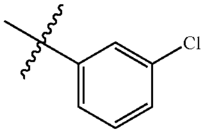, 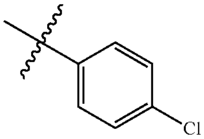,

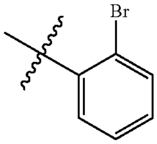, 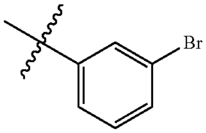,

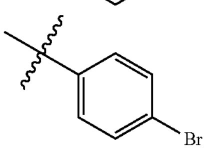,

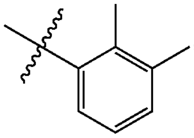, 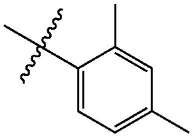,

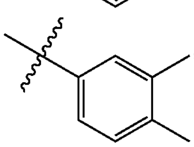,

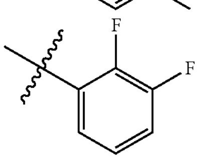, 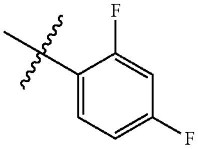,

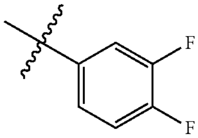, 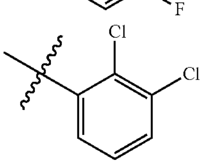,

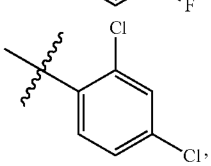, 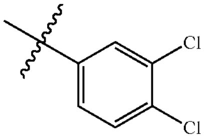,

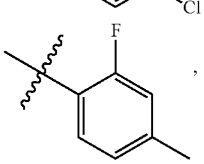, 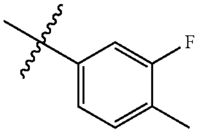,

-continued

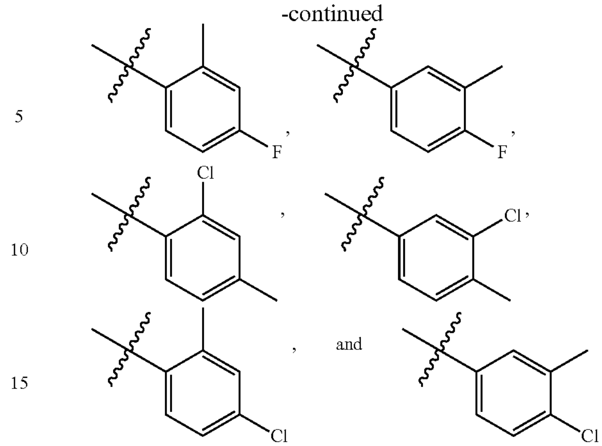

In some embodiments, the compound is a compound of Formula Ia', wherein $R^{21}$ is $C_2$-$C_9$heteroaryl that is unsubstituted or substituted by 1, 2, 3, or 4 $R^{51}$. In some embodiments the compound is a compound of Formula Ia', wherein $R^{21}$ is pyridyl that is unsubstituted or substituted by 1, 2, 3, or 4 $R^{51}$. In some embodiments, the compound is a compound of Formula Ia', wherein $R^{21}$ is pyridyl that is unsubstituted or substituted by 1, 2, or 3 $R^{51}$. In some embodiments, the compound is a compound of Formula Ia', wherein $R^{21}$ is pyridyl that is unsubstituted or substituted by 1, 2, or 3 $R^{51}$ and each $R^{51}$ is independently selected from halogen, $C_1$-$C_6$alkyl, $C_1$-$C_6$haloalkyl, $C_3$-$C_6$cycloalkyl, $C_2$-$C_9$heterocycloalkyl, —$OR^{71}$, —$N(R^{71})_2$, —CN, —$C(=O)R^{81}$, —$C(=O)OR^{71}$, —$C(=O)N(R^{71})_2$, —$S(=O)_2R^{81}$, and —$S(=O)_2N(R^{71})_2$. In some embodiments, the compound is a compound of Formula Ia', wherein $R^{21}$ is pyridyl that is unsubstituted or substituted by 1, 2, or 3 $R^{51}$ and each $R^{51}$ is independently selected from halogen, $C_1$-$C_6$alkyl, and $C_1$-$C_6$haloalkyl. In some embodiments, the compound is a compound of Formula Ia', wherein $R^{21}$ is pyridyl that is unsubstituted or substituted by 1 or 2 $R^{51}$ and each $R^{51}$ is independently selected from halogen, $C_1$-$C_6$alkyl, and $C_1$-$C_6$haloalkyl. In some embodiments, the compound is a compound of Formula Ia', wherein $R^{21}$ is pyridyl that is unsubstituted or substituted by 1 or 2 $R^{51}$ and each $R^{51}$ is independently selected from halogen and $C_1$-$C_6$alkyl. In some embodiments, the compound is a compound of Formula Ia', wherein $R^{21}$ is pyridyl substituted by 1 or 2 $R^{51}$ and each $R^{51}$ is independently selected from halogen and $C_1$-$C_6$alkyl. In some embodiments, the compound is a compound of Formula Ia', wherein $R^{21}$ is pyridyl substituted by 2 $R^{51}$ and each $R^{51}$ is independently selected from halogen and $C_1$-$C_6$alkyl. In some embodiments, the compound is a compound of Formula Ia', wherein $R^{21}$ is pyridyl substituted by 1 $R^{51}$ and $R^{51}$ is selected from halogen and $C_1$-$C_6$alkyl. In some embodiments, the compound is a compound of Formula Ia', wherein $R^{21}$ is pyridyl substituted by 1 $R^{51}$ and $R^{51}$ is halogen. In some embodiments, the compound is a compound of Formula Ia', wherein $R^{21}$ is pyridyl substituted by 1 $R^{51}$ and $R^{51}$ is $C_1$-$C_6$alkyl. In some embodiments, the compound is a compound of Formula Ia', wherein $R^{21}$ is unsubstituted pyridyl. In some embodiments, the compound is a compound of Formula Ia', wherein $R^{21}$ is selected from:

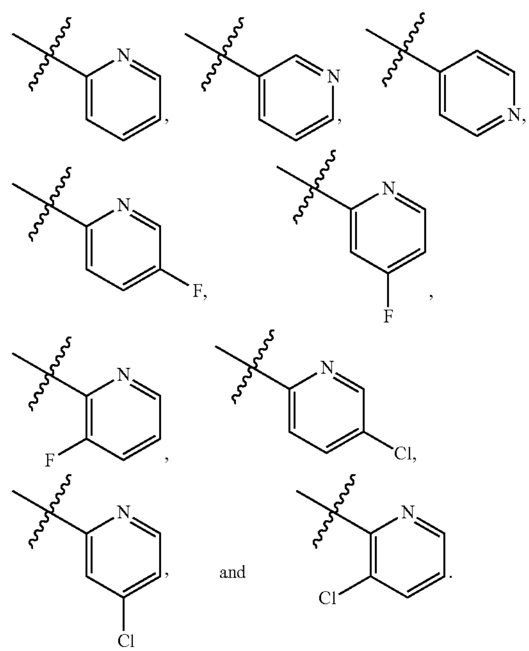

In some embodiments, the compound is a compound of Formula Ia', wherein $R^{31}$ is $C_1$-$C_6$alkyl that is unsubstituted or substituted by 1, 2, or 3 $R^{61}$. In some embodiments, the compound is a compound of Formula Ia', wherein $R^{31}$ is $C_1$-$C_6$alkyl that is unsubstituted or substituted by 1, 2, or 3 $R^{61}$ and each $R^{61}$ is independently selected from halogen, $C_3$-$C_6$cycloalkyl, $C_2$-$C_9$heterocycloalkyl, —$OR^{71}$, —$N(R^{71})_2$, —CN, —C(═O)$R^{81}$, —C(═O)$OR^{71}$, —C(═O)$N(R^{71})_2$, —S(═$O)_2R^{81}$, and —S(═$O)_2N(R^{71})_2$. In some embodiments, the compound is a compound of Formula Ia', wherein $R^{31}$ is $C_1$-$C_6$alkyl that is unsubstituted or substituted by 1, 2, or 3 $R^{61}$, each $R^{61}$ is independently selected from halogen, —$OR^{71}$, and —C(═O)$OR^{71}$, and each $R^{71}$ is independently selected from hydrogen and $C_1$-$C_6$alkyl. In some embodiments, the compound is a compound of Formula Ia', wherein $R^{31}$ is unsubstituted $C_1$-$C_6$alkyl. In some embodiments, the compound is a compound of Formula Ia', wherein $R^{31}$ is —$CH_3$. In some embodiments, the compound is a compound of Formula Ia', wherein $R^{31}$ is —$CH_2CH_3$. In some embodiments, the compound is a compound of Formula Ia', wherein $R^{31}$ is H.

In some embodiments, the present disclosure provides compounds represented by Formula Ib':

Formula Ib'

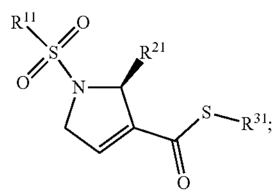

or a pharmaceutically acceptable salt thereof; wherein $R^{11}$ is $C_1$-$C_6$alkyl, $C_3$-$C_6$cycloalkyl, or $C_6$-$C_{10}$aryl, wherein the $C_1$-$C_6$alkyl, $C_3$-$C_6$cycloalkyl, or $C_6$-$C_{10}$aryl are unsubstituted or substituted by 1, 2, 3, or 4 $R^{41}$;

$R^{21}$ is $C_6$-$C_{10}$aryl or $C_2$-$C_9$heteroaryl, wherein the $C_6$-$C_{10}$aryl or $C_2$-$C_9$heteroaryl are unsubstituted or substituted by 1, 2, 3, or 4 $R^{51}$;

$R^{31}$ is H or $C_1$-$C_6$alkyl that is unsubstituted or substituted by 1, 2, or 3 $R^{61}$; each $R^{41}$ is independently selected from halogen, $C_1$-$C_6$alkyl, $C_1$-$C_6$haloalkyl, $C_3$-$C_6$cycloalkyl, $C_2$-$C_9$heterocycloalkyl, $C_2$-$C_9$heteroaryl, $C_6$-$C_{10}$aryl, oxo, —$OR^{71}$, —$N(R^{71})_2$, —CN, —C(═O)R81, —C(═O)$OR^{71}$, —C(═O)$N(R^{71})^2$, —$NR^{71}$C(═O)$R^{81}$, —$NR^{71}$S(═$O)_2R^{81}$, —S(═$O)_2R^{81}$, and —S(═$O)_2N(R^{71})_2$;

each $R^{51}$ is independently selected from halogen, $C_1$-$C_6$alkyl, $C_1$-$C_6$haloalkyl, $C_3$-$C_6$cycloalkyl, $C_2$-$C_9$heterocycloalkyl, $C_2$-$C_9$heteroaryl, $C_6$-$C_{10}$aryl, oxo, —$OR^{71}$, —$N(R^{71})_2$, —CN, —C(═O)R81, —C(═O)$OR^{71}$, —C(═O)$N(R^{71})^2$, —$NR^{71}$C(═O)$R^{81}$, —$NR^{71}$S(═$O)_2R^{81}$, —S(═$O)_2R^{81}$, and —S(═$O)_2N(R^{71})_2$;

each $R^{61}$ is independently selected from halogen, $C_1$-$C_6$alkyl, $C_1$-$C_6$haloalkyl, $C_3$-$C_6$cycloalkyl, $C_2$-$C_9$heterocycloalkyl, $C_2$-$C_9$heteroaryl, $C_6$-$C_{10}$aryl, oxo, —$OR^{71}$, —$N(R^{71})_2$, —CN, —C(═O)$R^{81}$, —C(═O)$OR^{71}$, —C(═O)$N(R^{71})_2$, —$NR^{71}$C(═O)$R^{81}$, —$NR^{71}$S(═$O)_2R^{81}$, —S(═$O)_2R^{81}$, and —S(═$O)_2N(R^{71})_2$;

each $R^{71}$ is independently selected from hydrogen, $C_1$-$C_6$alkyl, $C_3$-$C_6$cycloalkyl, $C_2$-$C_9$heterocycloalkyl, $C_2$-$C_9$heteroaryl, and phenyl, wherein the $C_1$-$C_6$alkyl, C3-$C_6$cycloalkyl, $C_2$-$C_9$heterocycloalkyl, $C_2$-$C_9$heteroaryl, and phenyl are unsubstituted or substituted with 1, 2, or 3 groups selected from halogen, $C_1$-$C_6$alkyl, $C_1$-$C_6$haloalkyl, $C_1$-$C_6$alkoxy, $C_1$-$C_6$haloalkoxy, $C_2$-$C_9$heterocycloalkyl, $C_2$-$C_9$heteroaryl, —$OR^{91}$, —$N(R^{91})_2$, —C(═O)$OR^{91}$, and —C(═O)$N(R^{9\ 1})_2$;

each $R^{81}$ is independently selected from $C_1$-$C_6$alkyl; and each $R^{91}$ is independently selected from hydrogen, $C_1$-$C_6$alkyl, and $C_1$-$C_6$haloalkyl.

In some embodiments, the compound is a compound of Formula Ib', wherein $R^{11}$ is $C_6$-$C_{10}$aryl that is unsubstituted or substituted by 1, 2, 3, or 4 $R^{41}$. In some embodiments, the compound is a compound of Formula Ib', wherein $R^{11}$ is phenyl that is unsubstituted or substituted by 1, 2, 3, or 4 $R^{41}$. In some embodiments, the compound is a compound of Formula Ib', wherein $R^{11}$ is phenyl that is unsubstituted or substituted by 1, 2, or 3 $R^{41}$. In some embodiments, the compound is a compound of Formula Ib', wherein $R^{11}$ is phenyl that is unsubstituted or substituted by 1, 2, or 3 $R^{41}$ and each $R^{41}$ is independently selected from halogen, $C_1$-$C_6$alkyl, $C_1$-$C_6$haloalkyl, $C_3$-$C_6$cycloalkyl, $C_2$-$C_9$heterocycloalkyl, —$OR^{71}$, —$N(R^{71})_2$, —CN, —C(═O)$R^{81}$, —C(═O)$OR^{71}$, —C(═O)$N(R^{71})_2$, —S(═$O)_2R^{81}$, and —S(═$O)_2N(R^{71})_2$. In some embodiments, the compound is a compound of Formula Ib', wherein $R^{11}$ is phenyl that is unsubstituted or substituted by 1, 2, or 3 $R^{41}$ and each $R^{41}$ is independently selected from halogen, $C_1$-$C_6$alkyl, $C_1$-$C_6$haloalkyl, —$OR^{71}$, and —C(═O)$OR^{71}$. In some embodiments, the compound is a compound of Formula Ib', wherein $R^{11}$ is phenyl that is unsubstituted or substituted by 1, 2, or 3 $R^{41}$ each $R^{41}$ is independently selected from halogen, $C_1$-$C_6$alkyl, $C_1$-$C_6$haloalkyl, —$OR^{71}$, and —C(═O)$OR^{71}$, and each $R^{71}$ is independently selected from hydrogen and $C_1$-$C_6$alkyl. In some embodiments, the compound is a compound of Formula Ib', wherein $R^{11}$ is phenyl that is unsubstituted or substituted by 1 or 2 $R^{41}$, each $R^{41}$ is independently selected from halogen, $C_1$-$C_6$alkyl, $C_1$-$C_6$haloalkyl, —$OR^{71}$, and —C(═O)$OR^{71}$, and each $R^{71}$ is independently selected from hydrogen and $C_1$-$C_6$alkyl. In some embodiments, the compound is a compound of Formula Ib', wherein $R^{11}$ is phenyl that is unsubstituted or substituted by 1 or 2 $R^{41}$ and each $R^{41}$ is independently selected from halogen and $C_1$-$C_6$alkyl. In some embodiments, the compound is a compound of Formula Ib', wherein $R^{11}$ is phenyl substituted by 1 or 2 $R^{41}$ and each $R^{41}$ is independently selected from halogen and $C_1$-$C_6$alkyl. In some embodiments, the compound is a compound of Formula Ib', wherein $R^{11}$ is phenyl substituted by 2 $R^{41}$ and each $R^{41}$ is independently selected from halogen and $C_1$-$C_6$alkyl. In some embodiments, the compound is a compound of Formula Ib', wherein $R^{11}$ is phenyl substituted by 1 $R^{41}$ and $R^{41}$ is selected from halogen and $C_1$-$C_6$alkyl. In some embodiments, the compound is a compound of Formula Ib', wherein $R^{11}$ is phenyl substituted by 1 $R^{41}$ and $R^{41}$ is halogen. In some embodiments, the compound is a compound of Formula Ib', wherein $R^{11}$ is phenyl substituted by 1 $R^{41}$ and $R^{41}$ is $C_1$-$C_6$alkyl. In some embodiments, the compound is a compound of Formula Ib', wherein $R^{11}$ is unsubstituted phenyl. In some embodiments, the compound is a compound of Formula Ib', wherein $R^{11}$ is selected from:

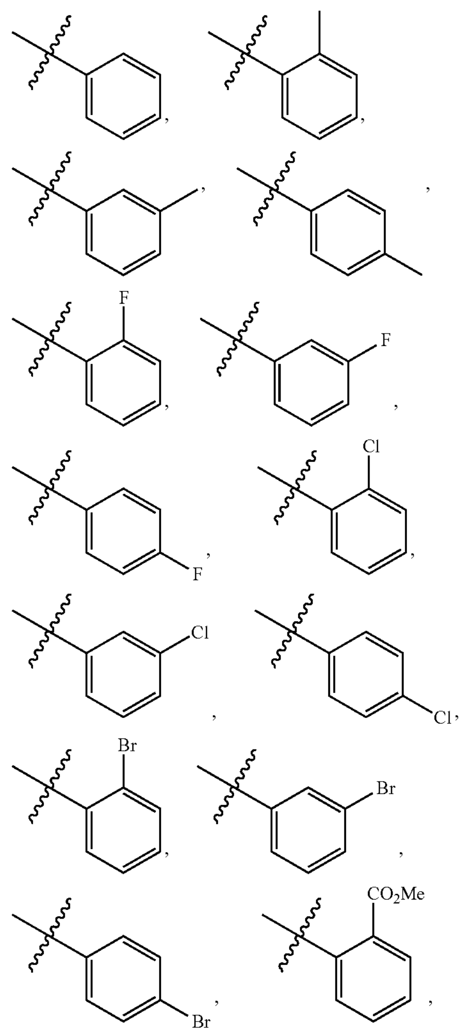

-continued

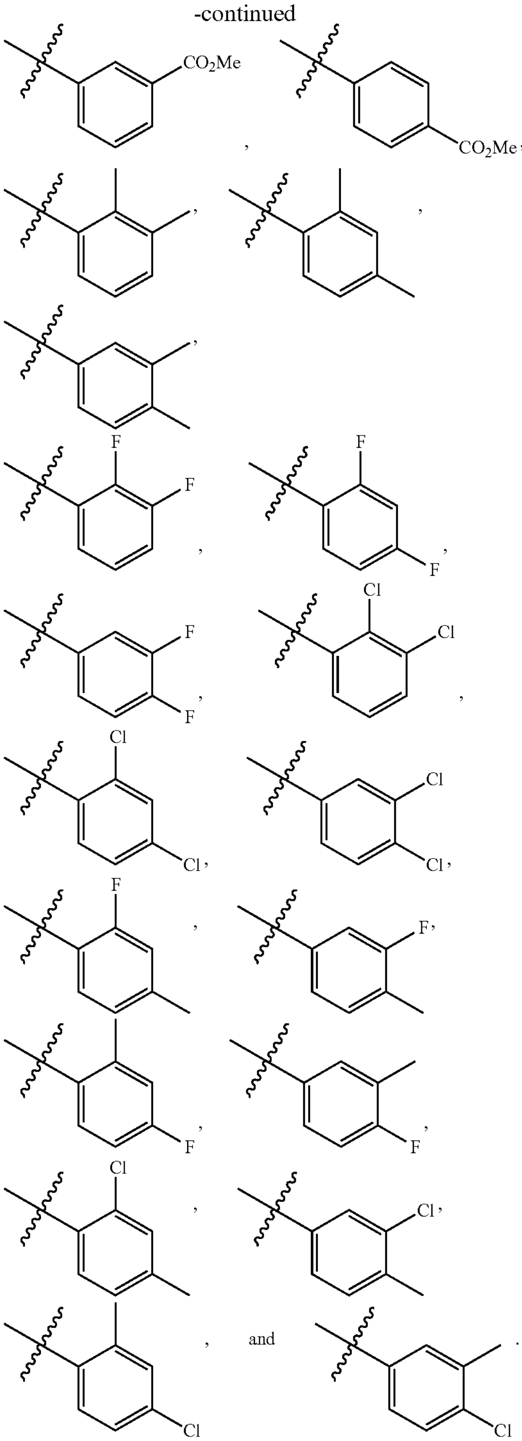

and

In some embodiments, the compound is a compound of Formula Ib', wherein $R^{11}$ is $C_1$-$C_6$alkyl that is unsubstituted or substituted by 1, 2, 3, or 4 $R^{41}$. In some embodiments, the compound is a compound of Formula Ib', wherein $R^{11}$ is $C_1$-$C_6$alkyl that is unsubstituted or substituted by 1, 2, or 3 $R^{41}$. In some embodiments, the compound is a compound of Formula Ib', wherein $R^{11}$ is $C_1$-$C_6$alkyl that is unsubstituted or substituted by 1, 2, or 3 $R^{41}$ and each $R^{41}$ is independently selected from halogen, $C_3$-$C_6$cycloalkyl, $C_2$-$C_9$heterocycloalkyl, —$OR^{41}$, —$N(R^{71})_2$, —CN, —C(═O)$R^{81}$, —C(═O)$OR^{71}$, —C(═O)$N(R^{71})_2$, —$S(=O)_2R^{81}$, and —$S(=O)_2N(R^{71})_2$. In some embodiments, the compound is a compound of Formula Ib', wherein $R^{11}$ is $C_1$-$C_6$alkyl that is unsubstituted or substituted by 1, 2, or 3 $R^{41}$, each $R^{41}$ is independently selected from halogen, —$OR^{71}$, and —$C(=O)OR^{71}$, and each $R^{71}$ is independently selected from hydrogen and $C_1$-$C_6$alkyl.

In some embodiments, the compound is a compound of Formula Ib', wherein $R^{11}$ is $C_3$-$C_6$cycloalkyl that is unsubstituted or substituted by 1, 2, 3, or 4 $R^{41}$. In some embodiments, the compound is a compound of Formula Ib', wherein $R^{11}$ is $C_3$-$C_6$cycloalkyl that is unsubstituted or substituted by 1, 2, or 3 $R^{41}$. In some embodiments, the compound is a compound of Formula Ib', wherein $R^{11}$ is $C_3$-$C_6$cycloalkyl that is unsubstituted or substituted by 1, 2, or 3 $R^{41}$ and each $R^{41}$ is independently selected from halogen, $C_1$-$C_6$alkyl, $C_1$-$C_6$haloalkyl, $C_3$-$C_6$cycloalkyl, $C_2$-$C_9$heterocycloalkyl, —$N(R^{71})_2$, —CN, —$C(=O)R^{81}$, —$C(=O)OR^{71}$, —$C(=O)N(R^{71})_2$, —$S(=O)_2R^{81}$, and —$S(=O)_2N(R^{71})_2$. In some embodiments, the compound is a compound of Formula Ib', wherein $R^{11}$ is $C_3$-$C_6$cycloalkyl that is unsubstituted or substituted by 1, 2, or $3R^{41}$, each $R^{41}$ is independently selected from halogen, $C_1$-$C_6$alkyl, $C_1$-$C_6$haloalkyl, —$OR^{71}$, and —$C(=O)OR^{71}$, and each $R^{71}$ is independently selected from hydrogen and $C_1$-$C_6$alkyl.

In some embodiments, the compound is a compound of Formula Ib', wherein $R^{21}$ is $C_6$-$C_{10}$aryl that is unsubstituted or substituted by 1, 2, 3, or 4 $R^{51}$. In some embodiments, the compound is a compound of Formula Ib', wherein $R^{21}$ is phenyl that is unsubstituted or substituted by 1, 2, 3, or 4 $R^{51}$. In some embodiments, the compound is a compound of Formula Ib', wherein $R^{21}$ is phenyl that is unsubstituted or substituted by 1, 2, or 3 $R^{51}$. In some embodiments, the compound is a compound of Formula Ib', wherein $R^{21}$ is phenyl that is unsubstituted or substituted by 1, 2, or 3 $R^1$ and each $R^5$ is independently selected from halogen, $C_1$-$C_6$alkyl, $C_1$-$C_6$haloalkyl, $C_3$-$C_6$cycloalkyl, $C_2$-$C_9$heterocycloalkyl, —$N(R^{71})_2$, —CN, —$C(=O)R^{81}$, —$C(=O)OR^{71}$, —$C(=O)N(R^{71})_2$, —$S(=O)_2R^{81}$, and —$S(=O)_2N(R^{71})_2$. In some embodiments, the compound is a compound of Formula Ib', wherein $R^{21}$ is phenyl that is unsubstituted or substituted by 1, 2, or 3 $R^{15}$ and each $R^{51}$ is independently selected from halogen, $C_1$-$C_6$alkyl, and $C_1$-$C_6$haloalkyl. In some embodiments, the compound is a compound of Formula Ib', wherein $R^{21}$ is phenyl that is unsubstituted or substituted by 1 or 2 $R^{51}$ and each $R^{51}$ is independently selected from halogen, $C_1$-$C_6$alkyl, and $C_1$-$C_6$haloalkyl. In some embodiments, the compound is a compound of Formula Ib', wherein $R^{21}$ is phenyl that is unsubstituted or substituted by 1 or 2 $R^1$ and each $R^{51}$ is independently selected from halogen and $C_1$-$C_6$alkyl. In some embodiments, the compound is a compound of Formula Ib', wherein $R^{21}$ is phenyl substituted by 1 or 2 $R^{51}$ and each $R^{51}$ is independently selected from halogen and $C_1$-$C_6$alkyl. In some embodiments, the compound is a compound of Formula Ib', wherein $R^{21}$ is phenyl substituted by 2 $R^{51}$ and each $R^{51}$ is independently selected from halogen and $C_1$-$C_6$alkyl. In some embodiments, the compound is a compound of Formula Ib', wherein $R^{21}$ is phenyl substituted by 1 $R^{51}$ and $R^{51}$ is selected from halogen and $C_1$-$C_6$alkyl. In some embodiments, the compound is a compound of Formula Ib', wherein $R^{21}$ is phenyl substituted by 1 $R^{51}$ and $R^{51}$ is halogen. In some embodiments, the compound is a compound of Formula Ib', wherein $R^{21}$ is phenyl substituted by 1 $R^{51}$ and $R^{51}$ is $C_1$-$C_6$alkyl. In some embodiments, the compound is a compound of Formula Ib', wherein $R^{21}$ is unsubstituted phenyl. In some embodiments, the compound is a compound of Formula Ib', wherein $R^{21}$ is selected from:

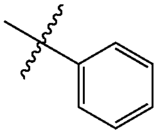, 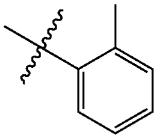,

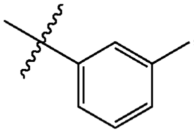, 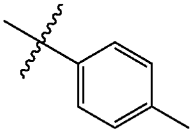,

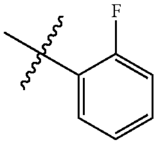, 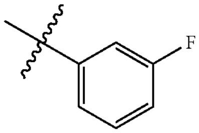,

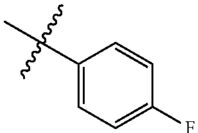, 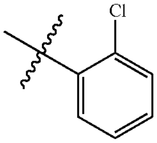,

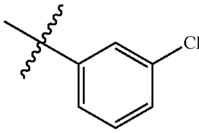, 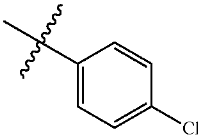,

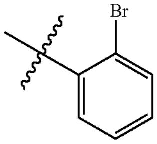, 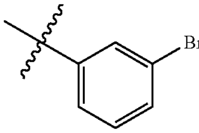,

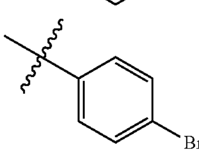,

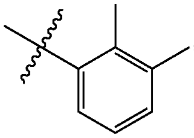, 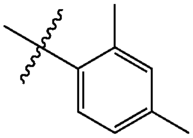,

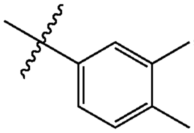,

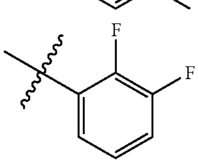, 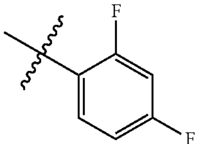,

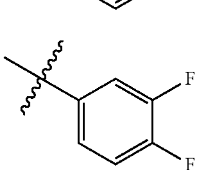, 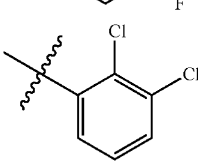,

-continued

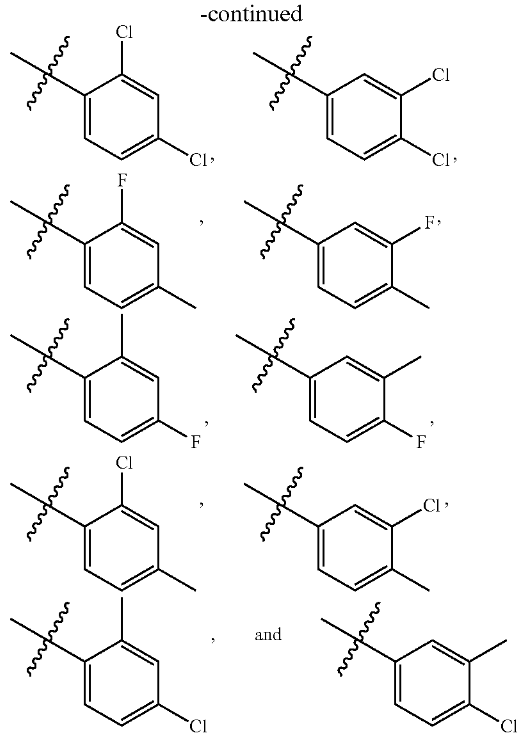

In some embodiments, the compound is a compound of Formula Ib', wherein $R^{21}$ is $C_2$-$C_9$heteroaryl that is unsubstituted or substituted by 1, 2, 3, or 4 $R^{51}$. In some embodiments, the compound is a compound of Formula Ib', wherein $R^{21}$ is pyridyl that is unsubstituted or substituted by 1, 2, 3, or 4 $R^{51}$. In some embodiments, the compound is a compound of Formula Ib', wherein $R^{21}$ is pyridyl that is unsubstituted or substituted by 1, 2, or 3 $R^{51}$. In some embodiments, the compound is a compound of Formula Ib', wherein $R^{21}$ is pyridyl that is unsubstituted or substituted by 1, 2, or 3 $R^{51}$ and each $R^{51}$ is independently selected from halogen, $C_1$-$C_6$alkyl, $C_1$-$C_6$haloalkyl, $C_3$-$C_6$cycloalkyl, $C_2$-$C_9$heterocycloalkyl, —$OR^{71}$, —$N(R^{71})_2$, —CN, —C(═O)$R^{81}$, —C(═O)$OR^{71}$, —C(═O)$N(R^{71})_2$, —S(═$O)_2R^{81}$, and —S(═$O)_2N(R^{71})_2$. In some embodiments, the compound is a compound of Formula Ib', wherein $R^{21}$ is pyridyl that is unsubstituted or substituted by 1, 2, or 3 $R^{51}$ and each $R^{51}$ is independently selected from halogen, $C_1$-$C_6$alkyl, and $C_1$-$C_6$haloalkyl. In some embodiments, the compound is a compound of Formula Ib', wherein $R^{21}$ is pyridyl that is unsubstituted or substituted by 1 or 2 $R^{51}$ and each $R^{51}$ is independently selected from halogen, $C_1$-$C_6$alkyl, and $C_1$-$C_6$haloalkyl. In some embodiments, the compound is a compound of Formula Ib', wherein $R^{21}$ is pyridyl that is unsubstituted or substituted by 1 or 2 $R^{51}$ and each $R^{51}$ is independently selected from halogen and $C_1$-$C_6$alkyl. In some embodiments, the compound is a compound of Formula Ib', wherein $R^{21}$ is pyridyl substituted by 1 or 2 $R^{51}$ and each $R^{51}$ is independently selected from halogen and $C_1$-$C_6$alkyl. In some embodiments, the compound is a compound of Formula Ib', wherein $R^{21}$ is pyridyl substituted by 2 $R^{51}$ and each $R^{51}$ is independently selected from halogen and $C_1$-$C_6$alkyl. In some embodiments, the compound is a compound of Formula Ib', wherein $R^{21}$ is pyridyl substituted by 1 $R^{51}$ and $R^{51}$ is selected from halogen and $C_1$-$C_6$alkyl. In some embodiments the compound is a compound of Formula Ib', wherein $R^{21}$ is pyridyl substituted by 1 $R^{51}$ and $R^{51}$ is halogen. In some embodiments, the compound is a compound of Formula Ib', wherein $R^{21}$ is pyridyl substituted by 1 $R^{51}$ and $R^{51}$ is $C_1$-$C_6$alkyl. In some embodiments, the compound is a compound of Formula Ib', wherein $R^{21}$ is unsubstituted pyridyl. In some embodiments, the compound is a compound of Formula Ib', wherein $R^{21}$ is selected from:

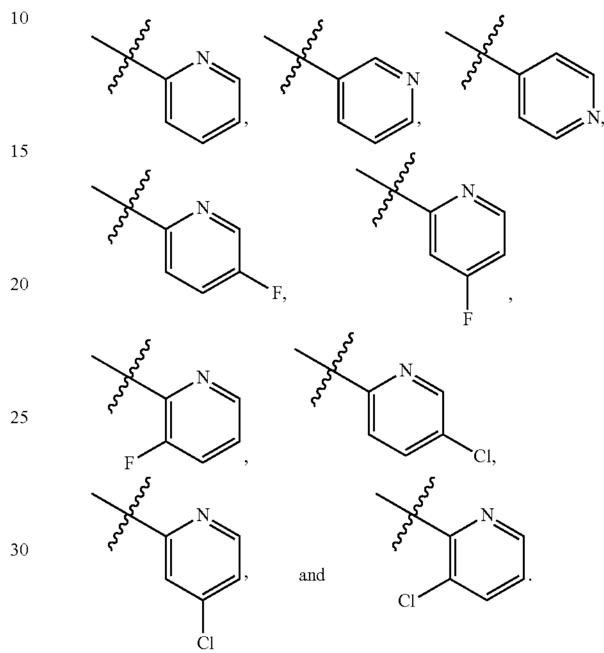

In some embodiments, the compound is a compound of Formula Ib', wherein $R^{31}$ is $C_1$-$C_6$alkyl that is unsubstituted or substituted by 1, 2, or 3 $R^{61}$. In some embodiments, the compound is a compound of Formula Ib', wherein $R^{31}$ is $C_1$-$C_6$alkyl that is unsubstituted or substituted by 1, 2, or 3 $R^{61}$ and each $R^{61}$ is independently selected from halogen, $C_3$-$C_6$cycloalkyl, $C_2$-$C_9$heterocycloalkyl, —$OR^{71}$, —$N(R^{71})_2$, —CN, —C(═O)$R^{81}$, —(═O)$OR^{71}$, —C(═O)$N(R^{71})_2$, —S(═$O)_2R^{81}$, and —S(═$O)_2N(R^{71})_2$. In some embodiments, the compound is a compound of Formula Ib', wherein $R^{31}$ is $C_1$-$C_6$alkyl that is unsubstituted or substituted by 1, 2, or 3 $R^{61}$, each $R^{61}$ is independently selected from halogen, —$OR^{71}$, and —C(═O)$OR^{71}$, and each $R^{71}$ is independently selected from hydrogen and $C_1$-$C_6$alkyl. In some embodiments, the compound is a compound of Formula Ib', wherein $R^{31}$ is unsubstituted $C_1$-$C_6$alkyl. In some embodiments, the compound is a compound of Formula Ib', wherein $R^{31}$ is —$CH_3$. In some embodiments, the compound is a compound of Formula Ib', wherein $R^{31}$ is —$CH_2CH_3$. In some embodiments, the compound is a compound of Formula Ib', wherein $R^{31}$ is H.

In further aspects, the present disclosure provides compositions comprising a compound of Formula I and at least one pharmaceutically acceptable excipient. In certain embodiments, the compound has an enantiomeric excess (ee) greater than 95%, 96%, 97%, 98%, or 99%. In certain embodiments, the compound is substantially free of one enantiomer. In certain embodiments, the enantiomer is the R enantiomer. In other embodiments, the enantiomer is the S enantiomer.

In yet further aspects, the present disclosure provides methods of modulating cardiac rhythmicity in a subject, comprising administering a compound of Formula I or a composition thereof to the subject. In certain embodiments, the cardiac rhythmicity is increased. In certain embodiments, the cardiac rhythmicity is modulated by $Ca^{+}$ or $Ca^{2+}$ homeostasis. In certain embodiments, the compounds of the disclosure increase $Ca^{+}$ or $Ca^{2+}$ homeostasis. In certain embodiments, the cardiac rhythmicity is modulated by $Ca^{+}$ homeostasis. In certain embodiments, the compounds of the disclosure increase $Ca^{+}$ homeostasis. In certain embodiments, the cardiac rhythmicity is modulated by $Ca^{2+}$ homeostasis. In certain embodiments, the compounds of the disclosure increase $Ca^{2+}$ homeostasis. In certain embodiments, the cardiac rhythmicity is modulated by VDAC2 or VDAC1. In certain embodiments, the compounds of the disclosure increase VDAC2 or VDAC1 expression. In certain embodiments, the compounds of the disclosure activate VDAC2 or VDAC1. In certain embodiments, the compounds of the disclosure induce $Ca^{2+}$ transporting activity of VDAC2 or VDAC1. In certain embodiments, the cardiac rhythmicity is modulated by MUC or MICU1. In certain embodiments, the compounds of the disclosure increase MUC or MICU1 expression. In certain embodiments, the compounds of the disclosure activate MUC or MICU1.

In yet further aspects, the present disclosure provides methods of treating a cardiac disorder in a subject, comprising administering a compound of Formula I or a composition thereof to the subject. In certain embodiments, the cardiac disorder is modulated by $Ca^{+}$ or $Ca^{2+}$ homeostasis. In certain embodiments, the compounds of the disclosure increase $Ca^{+}$ or $Ca^{2+}$ homeostasis. In certain embodiments, the cardiac disorder is modulated by $Ca^{+}$ homeostasis. In certain embodiments, the compounds of the disclosure increase $Ca^{+}$ homeostasis. In certain embodiments, the cardiac disorder is modulated by $Ca^{2+}$ homeostasis. In certain embodiments, the compounds of the disclosure increase $Ca^{2+}$ homeostasis. In certain embodiments, the cardiac disorder is modulated by VDAC2 or VDAC1. In certain embodiments, the cardiac disorder is the result of VDAC2 or VDAC1 underexpression. In certain embodiments, the compounds of the disclosure increase VDAC2 or VDAC1 expression. In certain embodiments, the compounds of the disclosure activate VDAC2 or VDAC1. In certain embodiments, the compounds of the disclosure induce $Ca^{2+}$ transporting activity of VDAC2 or VDAC1. In certain embodiments, the cardiac disorder is modulated by MUC or MICU1 . In certain embodiments, the cardiac disorder is the result of MUC or MICU1 underexpression. In certain embodiments, the compounds of the disclosure increase MUC or MICU1 expression. In certain embodiments, the compounds of the disclosure activate MUC or MICU1 . In certain embodiments, the cardiac disorder is cardiac fibrillation, arrhythmia, atrial fibrillation, sick sinus syndrome, catecholaminergic polymorphic ventricular tachycardia, or cardiomyopathy.

In yet further aspects, the present disclosure provides methods of making compounds of Formula I, wherein the method comprises performing a transformation according to Scheme I:

Scheme I

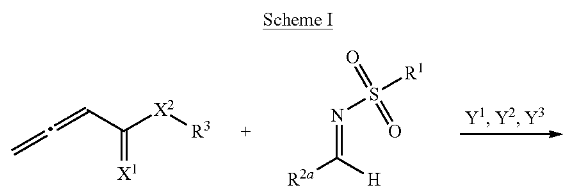

-continued

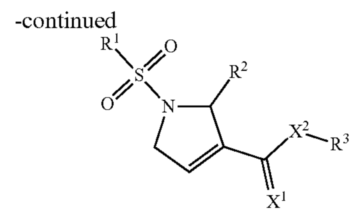

wherein, $Y^1$ is a chiral phosphine;

$Y^2$ is a chiral ligand;

$Y^3$ is a solvent;

$X^1$ is O, S, or $NR^4$; or $X^1$, $X^2$, and $R^3$ combine to form a heterocyclyl;

$X^2$ is O, S, or $NR^5$; or $X^2$ and $R^3$ combine to form a heterocyclyl;

$R^1$ is alkyl, cycloalkyl, or aryl;

$R^2$ and $R^{2a}$ are each aryl or heteroaryl;

$R^3$ is H or alkyl; and $R^4$ and $R^5$ are each independently selected from H or alkyl.

In certain embodiments of Scheme I, the compound has an enantiomeric excess (ee) greater than 95%, 96%, 97%, 98%, or 99%. In certain embodiments, the compound is substantially free of one enantiomer.

In certain embodiments of Scheme I, $R^2$ is in the R-configuration. In other embodiments, $R^2$ is in the S-configuration.

In certain embodiments of Scheme I, the chiral phosphine is represented by formula IV:

IV

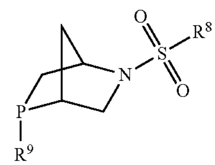

wherein, $R^8$ and $R^9$ are each independently selected from is alkyl, cycloalkyl, and aryl.

In certain embodiments of formula IV, $R^8$ is aryl (e.g., phenyl).

In certain embodiments of formula IV, $R^9$ is aryl (e.g., phenyl).

In certain embodiments of Scheme I, the chiral ligand is a chiral bi-naphthalene substituted with at least two hydroxyl groups. In certain embodiments, the chiral ligand is S-BINOL. In other embodiments, the chiral ligand is R-BINOL.

In certain embodiments of Scheme I, the solvent is an aprotic solvent. In certain embodiments, the aprotic solvent is a chlorinated solvent (e.g., dichloromethane).

In certain embodiments of Scheme I, the step according to Scheme I is performed at about −25° C. to about 10° C. In certain embodiments, the step according to Scheme I is performed at about 0° C.

In certain embodiments of Scheme I, the chiral phosphine is present at about 0.5 mol % to about 50 mol. % as compared to

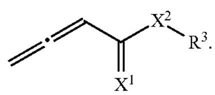

In certain embodiments, the chiral phosphine is present at about 5 mol. %, 10 mol. %, 15 mol. %, 20 mol. %, 25 mol. %, or 30 mol. %, as compared to

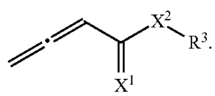

In certain embodiments, the chiral phosphine is present at about 20 mol. % as compared to

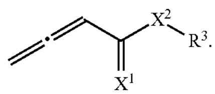

In certain embodiments of Scheme I, the chiral ligand is present at about 0.5 mol % to about 50 mol. % as compared to

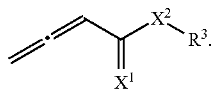

In certain embodiments, the chiral ligand is present at about 5 mol. %, 10 mol. %, 15 mol. %, 20 mol. %, 25 mol. %, or 30 mol. %, as compared to

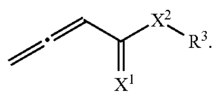

In certain embodiments, the chiral ligand is present at about 20 mol. as compared to

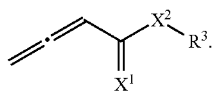

In certain embodiments of Scheme I, the method further comprises a purification step. In certain embodiments, the purification step comprises recrystallization, column chromatography, preparative thin layer chromatography, or high performance liquid chromatography. In certain embodiments, the purification step comprises recrystallization.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, Mass. (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, Calif. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO-CH2-O-alkyl, $—OP(O)(O\text{-alkyl})_2$ or $—CH_2—OP(O)(O\text{-alkyl})_2$. Preferably, "optionally substituted" refers to the replacement of one to four hydrogen radicals in a given structure with the substituents mentioned above. More preferably, one to three hydrogen radicals are replaced by the sub stituents as mentioned above. It is understood that the substituent can be further substituted.

As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS-.

The term "amide", as used herein, refers to a group

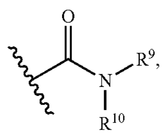

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

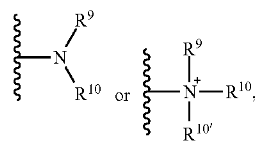

wherein $R^9$, $R^{10}$, and $R^{10}$, each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

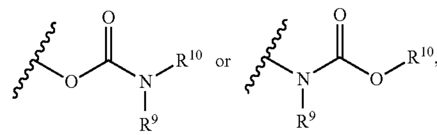

wherein $R^9$ and $R^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group $—OCO_2—$. The term "carboxy", as used herein, refers to a group represented by the formula $—CO_2H$.

The term "ester", as used herein, refers to a group $—C(O)OR^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group $—OSO_3H$, or a pharmaceutically acceptable salt thereof.

The term "sulfonamide" is art-recognized and refers to the group represented by the general formulae

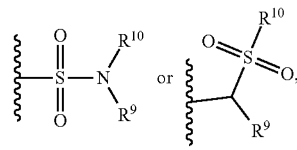

wherein $R^9$ and $R^{10}$ independently represents hydrogen or hydrocarbyl.

The term "sulfoxide" is art-recognized and refers to the group-S(O)—.

The term "sulfonate" is art-recognized and refers to the group $SO_3H$, or a pharmaceutically acceptable salt thereof.

The term "sulfone" is art-recognized and refers to the group $—S(O)_2—$.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group $—C(O)SR^9$ or $—SC(O)R^9$ wherein $R^9$ represents a hydrocarbyl.

The term "thioether", as used herein, is equivalent to an ether, wherein the oxygen is replaced with a sulfur.

The term "urea" is art-recognized and may be represented by the general formula

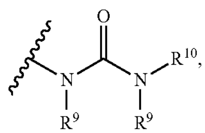

wherein $R^9$ and $R^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

In certain embodiments, compounds of the disclosure may be racemic. In certain embodiments, compounds of the disclosure may be enriched in one enantiomer. For example, a compound of the disclosure may have greater than about 30% ee, 40% ee, 50% ee, 60% ee, 70% ee, 80% ee, 90% ee, 95%, 96% ee, 97% ee, 98% ee, 99% ee, or greater ee.

As is generally understood in the art, single bonds drawn without stereochemistry do not indicate the stereochemistry of the compound. The compound of formula I provides an example of a compound for which no stereochemistry is indicated.

In certain embodiments, a composition or compound of the disclosure may be enriched to provide predominantly one enantiomer of a compound. An enantiomerically enriched composition or compound may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound contains 98 grams of a first enantiomer and 2 grams of a second enantiomer, it would be said to contain 98 mol percent of the first enantiomer and only 2 mol % of the second enantiomer.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "LogS" or "logS" as used herein is used in the art to quantify the aqueous solubility of a compound. The aqueous solubility of a compound significantly affects its absorption and distribution characteristics. A low solubility often goes along with a poor absorption. LogS value is a unit stripped logarithm (base 10) of the solubility measured in mol/liter.

EXAMPLES

The invention now being generally described, it will be more readily understood by reference to the following examples which are included merely for purposes of illustration of certain aspects and embodiments of the present invention, and are not intended to limit the invention.

Example 1

Preparation of Exemplary Compounds of the Disclosure FS001 (efsevin)

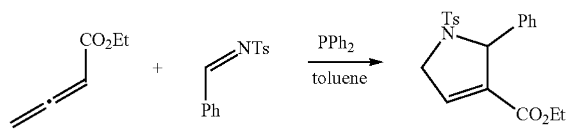

The purity was checked by HPLC analysis using Poroshell 120 EC-C18 column and $H_2O/CH_3CN$ (40/60) as eluent: flow rate=0.5 mL/min, λ254 nm, retention time: t=8.49 min.

FS002 [(R)-efsevin]

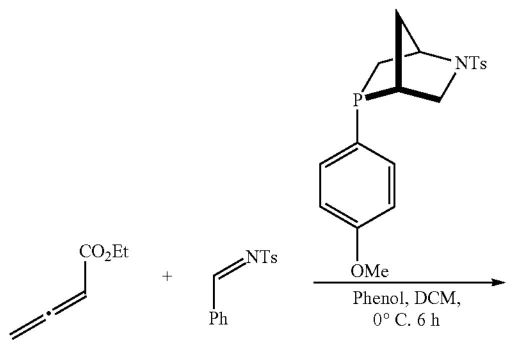

-continued

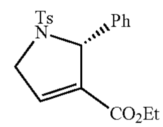

The $_D$-Hyp derived chiral phosphine endo-p-anisyl-Hyp-Phos (0.2 equiv) was weighed and added to a flask in a glove box. The reaction vessel was removed from the glove box, then the imine (1 equiv) and phenol (0.1 equiv) were quickly added. Dichloromethane (DCM; 0.1 M) was added and the reaction vessel was cooled with an ice bath. Ethyl allenoate (1.5 equiv) was added dropwise to the reaction mixture via syringe. The reaction was stirred until the compete consumption of the imine was observed (6 h, TLC, 40% EtOAc in hexanes, $R_f$=0.3). The reaction was warmed to room temperature. The solvent was removed by rotary evaporation, and the product was then purified by FCC (SiO2, EtOAc in Hexanes). After FCC fractions were concentration, a white crystalline product formed (95% yield and 91-92% ee). These crystals were collected and subjected to two rounds of recrystallization. First, the solids were dissolved in boiling 9% EtOAc in cyclohexane. The solution was allowed to cool to room temperature and sit overnight undisturbed. Resulting crystals (97% ee) were collected and subjected to the next recrystallization immediately. Hexanes (approx. 1 mL/50 mg) was layered over the crystals and heated to a boil. While heating, a dropwise addition of EtOAc was continued until the solid was completely dissolved. The solution was allowed to cool to room temperature and stand. The crystals formed were collected to obtain (R)-efsevin (99% ee). Efsevin (in racemic forms) has been synthesized previously; its spectral data matched the reported in the following reference: (*J. Am. Chem. Soc.* 2008, 130, 5660.) The enantiomeric accesses were determined by HPLC analysis using REGIS (R, R)-DACH DNB column and hexanes/$CH_2Cl_2$ (40/60) as eluent with a flow rate of 2 mL/min. The purity was checked by HPLC analysis using Poroshell 120 EC-C18 column and $H_2O/CH_3CN$ (40/60) as eluent: flow rate=0.5 mL/min, λ=254 nm, retention time: t=8.08 min.

FS003 [(S)-efsevin]

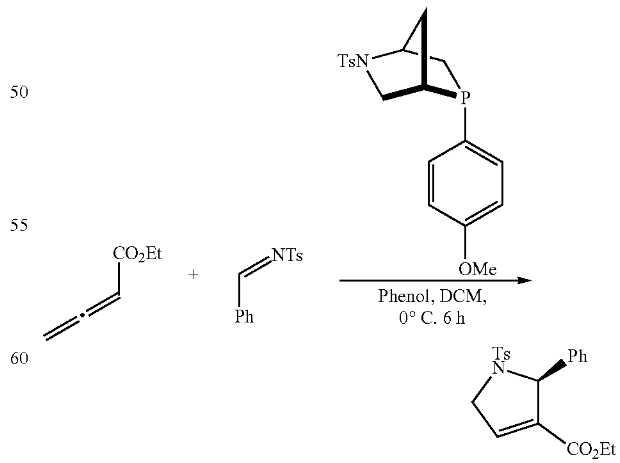

See the synthetic procedure for FS002. The purity was checked by HPLC analysis using Poroshell 120 EC-C18 column and $H_2O/CH_3CN$ (40/60) as eluent: flow rate=0.5 mL/min, λ=254 nm, retention time: t=8.10 min.

FS004

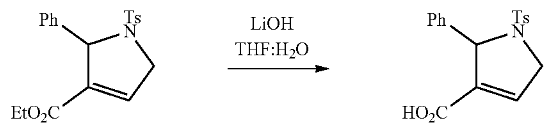 [SMILES: CCOC(=O)C1=CCN(S(=O)(=O)c2ccc(C)cc2)C1c1ccccc1 ; Cc1ccc(S(=O)(=O)N2CC=C(C(=O)O)C2c2ccccc2)cc1]

The purity was checked by HPLC analysis using Poroshell 120 EC-C18 column and $H_2O/CH_3CN$ (40/60) as eluent: flow rate=0.5 mL/min, λ=254 nm, retention time: t=3.74 min.

FS007

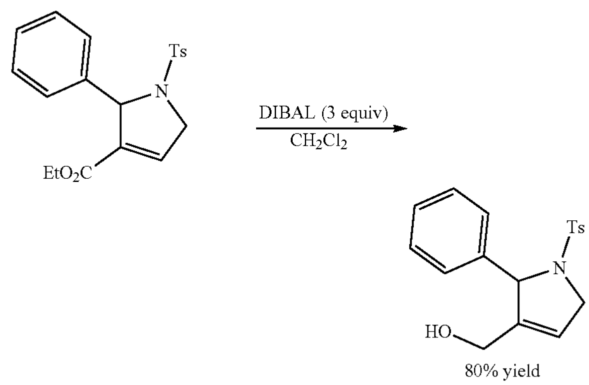

To a cooled (0° C.) stirred solution of ethyl 2-phenyl-1-tosyl-2,5-dihydro-1H-pyrrole-3-carboxylate (0.1 g, 0.27 mmol) in $CH_2Cl_2$ (3 mL) was added DIBAL (1.0 M in toluene) (0.81 mL, 0.81 mmol). The mixture was stirred for 1 h, quenched with MeOH, and concentrated under reduced pressure. The residue was chromatographed on silica gel to yield the title compound in 80% yield. The purity was checked by HPLC analysis using Poroshell 120 EC-C18 column and $H_2O/CH_3CN$ (40/60) as eluent: flow rate=0.5 mL/min, λ=254 nm, retention time: t=3.96 min.

FS008

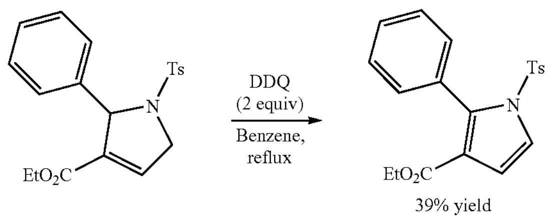 [SMILES: CCOC(=O)C1=CCN(S(=O)(=O)c2ccc(C)cc2)C1c1ccccc1 ; CCOC(=O)c1ccn(S(=O)(=O)c2ccc(C)cc2)c1-c1ccccc1]

A mixture of 2-phenyl-1-tosyl-2,5-dihydro-1H-pyrrole-3-carboxylate (0.1 g, 0.27 mmol) and DDQ (0.12 g, 0.54 mmol) in benzene (3 mL) was heated at about 130° C. under nitrogen and monitored by TLC. After the reaction was complete, the reaction mixture was concentrated under reduced pressure and the residue was purified by column chromatography on silica gel to afford the title compound in 39% yield.

FS009

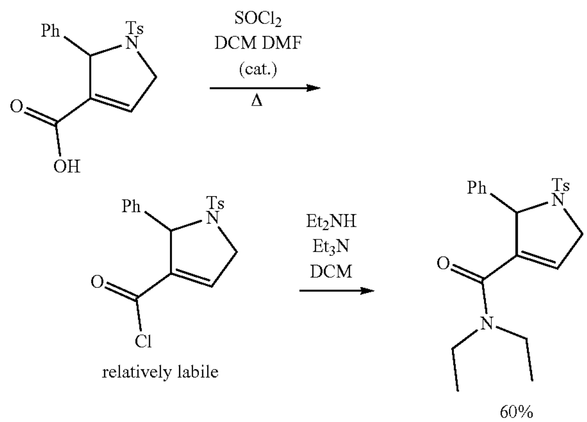

F7 carboxylic acid was dissolved in DCM (0.3 M). DMF was added (~1 drop per 5 mL of DCM) followed by SOCI2 (5 equiv) and the solution was heated to reflux until consumption of starting material (~4 h, TLC, 40% EtOAc in hexanes, Rf=0.5). The solution was cooled to room temperature and solvent/excess SOCI2 was removed by rotary evaporation. The flask was then attached to a high vacuum line to ensure complete removal of SOCI2. The acid chloride was used for the next step without further purification. The acid chloride was dissolved in DCM (0.2 M). The reaction was cooled with an ice bath and the amine (1.3 equiv) was added, followed by TEA (1 equiv for free amine, 2.6 equiv for amine HCI salt). The solution was slowly allowed to warm to room temperature and stirred overnight. The reaction was quenched with water and entranced with DCM (x3) and washed with brine (x1). The combined organic layer was dried with $Na_2SO_4$. The solvent was removed by rotary evaporation, and the amide was then purified by FCC (SiO2, EtOAc in Hexanes). The purity was checked by HPLC analysis using Poroshell 120 EC-C18 column and $H_2O$/CH3CN (40/60) as eluent: flow rate=0.5 mL/min, λ=254 nm, retention time: t=5.60 min.

FS010

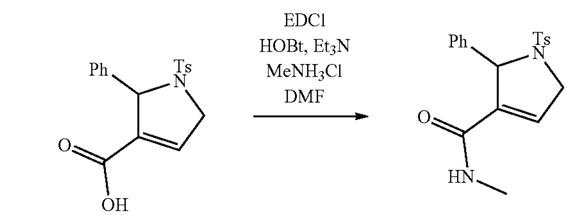 [SMILES: Cc1ccc(S(=O)(=O)N2CC=C(C(=O)O)C2c2ccccc2)cc1 ; CNC(=O)C1=CCN(S(=O)(=O)c2ccc(C)cc2)C1c1ccccc1]

F7 carboxylic acid and HOBt (1.2 equiv) were dissolved in DMF (0.1M). The reaction was then cooled with an ice bath. The amine (1.5 equiv), EDCI (1.2 equiv) and TEA (1 equiv for free amine, 3 equiv for amine HCI salt), were added in that order. The reaction was allowed to slowly warm to room temperature and stirred for 16 h. The reaction was diluted with an equal portion water and extracted with EtOAc. The combined organic layer was then washed with water (x3) and washed with brine once. The combined organic layer was dried with $Na_2SO_4$. The solvent was removed by rotary evaporation, and the amide was then purified by FCC ($SiO_2$, 50% EtOAc in Hexanes). The purity was checked by HPLC analysis using Poroshell 120 EC-C18 column and $H_2O/CH_3CN$ (40/60) as eluent: flow rate=0.5 mL/min, λ=254 nm, retention time: t=3.45 min.

FS011

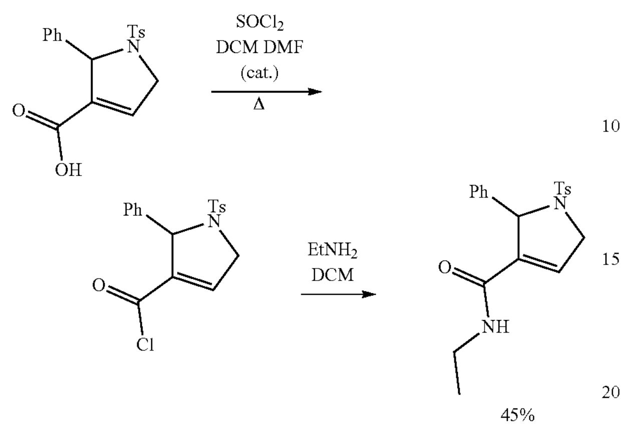

See the synthetic procedure for FS009. The purity was checked by HPLC analysis using Poroshell 120 EC-C18 column and $H_2O/CH_3CN$ (40/60) as eluent: flow rate=0.5 mL/min, λ=254 nm, retention time: t=3.95 min.

FS012

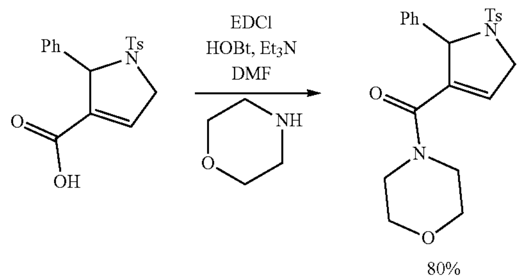

See the synthetic procedure for FS010. The purity was checked by HPLC analysis using Poroshell 120 EC-C18 column and $H_2O/CH_3CN$ (40/60) as eluent: flow rate=0.5 mL/min, λ=254 nm, retention time: t=3.80 min.

FS013

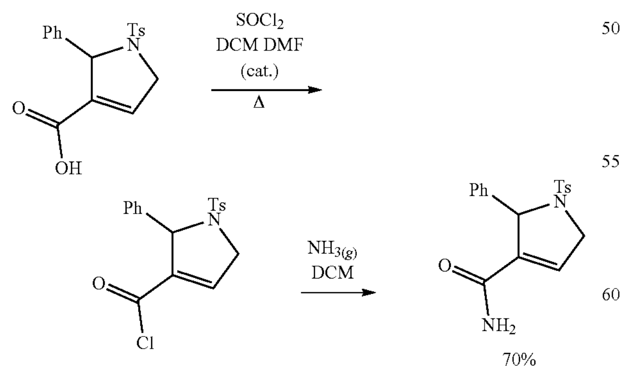

The acid chloride was dissolved in DCM (0.05 M) and cooled with an ice bath. Ammonia was slowly bubbled through the reaction mixture until completion (~2 h, TLC, 80% EtOAc in hexanes, $R_f$=0.3). The reaction was quenched with the addition of water, extracted with EtOAc (x3) and washed with brine. The combined organic layer was dried with $Na_2SO_4$. The solvent was removed by rotary evaporation, and the amide was then purified by FCC ($SiO_2$, 80% EtOAc in Hexanes). The purity was checked by HPLC analysis using Poroshell 120 EC-C18 column and $H_2O/CH_3CN$ (40/60) as eluent: flow rate=0.5 mL/min, λ=254 nm, retention time: t=3.17 min.

FS014

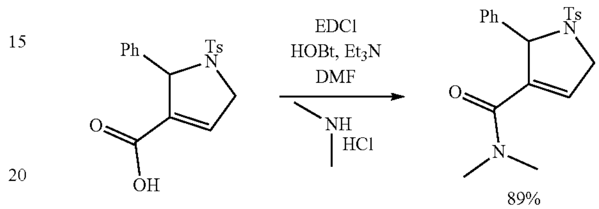

See the synthetic procedure for FS010. The purity was checked by HPLC analysis using Poroshell 120 EC-C18 column and $H_2O/CH_3CN$ (40/60) as eluent: flow rate=0.5 mL/min, λ=254 nm, retention time: t=3.97 min.

FS015

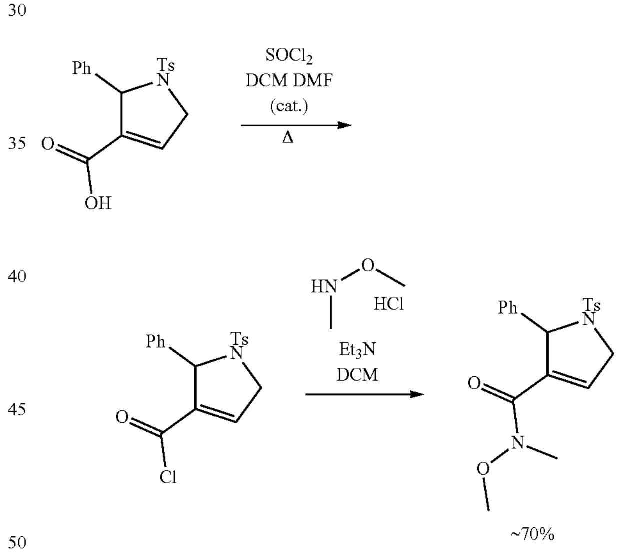

See the synthetic procedure for FS009. The purity was checked by HPLC analysis using Poroshell 120 EC-C18 column and $H_2O/CH_3CN$ (40/60) as eluent: flow rate=0.5 mL/min, λ=254 nm, retention time: t=4.56 min.

FS016

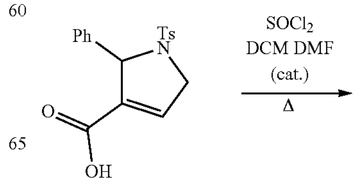

-continued

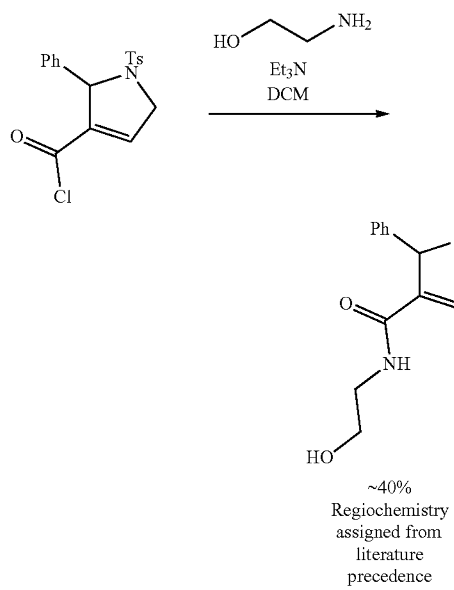

See the synthetic procedure for FS009.

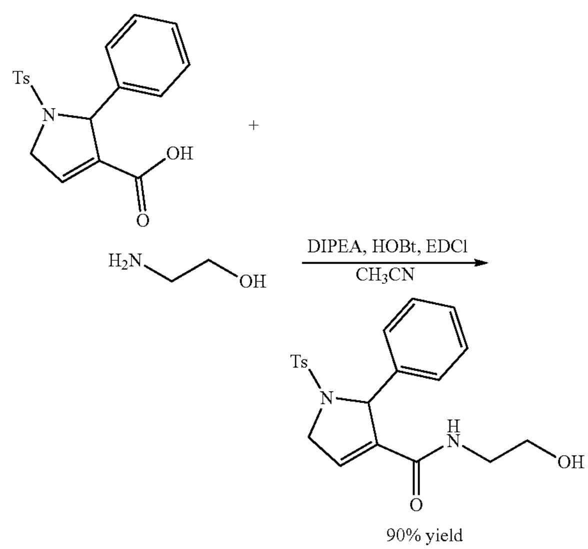

See the synthetic procedure for FS078. The purity was checked by HPLC analysis using Poroshell 120 EC-C18 column and $H_2O/CH_3CN$ (40/60) as eluent: flow rate=0.5 mL/min, λ=254 nm, retention time: t=2.91 min.

FS059

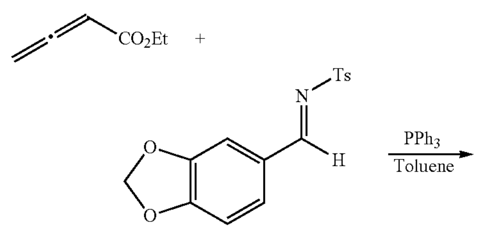

-continued

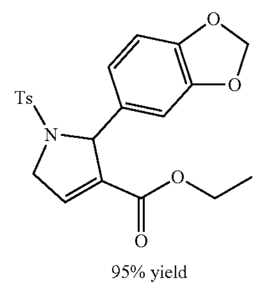

The imine (91 mg, 0.3 mmol) and triphenylphosphine (78.6 mg, 0.3 mmol) were dissolved in toluene. Ethyl buta-2,3-dienoate (40 mg, 0.36 mmol) was added dropwised. The mixture was stirred at room temperature overnight. Solvent was removed under vacuum and the residue was purified by flash chromatography to yield the title compound in 95% yield. The purity was checked by HPLC analysis using Poroshell 120 EC-C18 column and $H_2O/CH_3CN$ (20/80) as eluent: flow rate=0.5 mL/min, λ=254 nm, retention time: t=3.38 min.

FS060

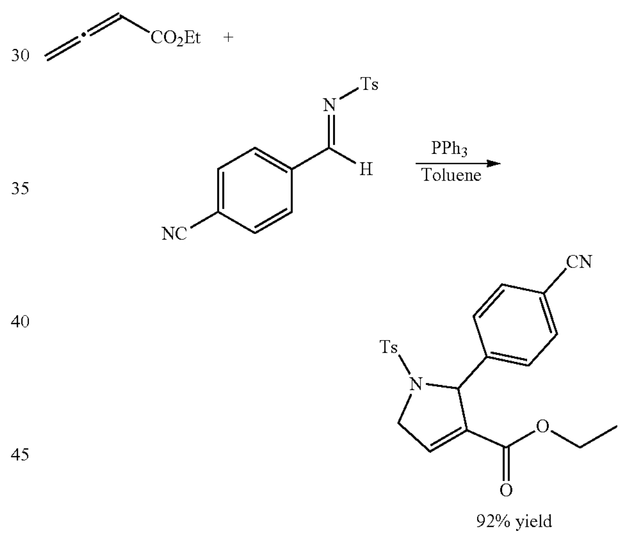

The imine (170 mg, 0.6 mmol) and triphenylphosphine (157.2 mg, 0.6 mmol) were dissolved in toluene. Ethyl buta-2,3-dienoate (80 mg, 0.72 mmol) was added dropwised. The mixture was stirred at room temperature overnight. Solvent was removed under vacuum and the residue was purified by flash chromatography to yield the title compound in 92% yield. The purity was checked by HPLC analysis using Poroshell 120 EC-C18 column and $H_2O/CH_3CN$ (20/80) as eluent: flow rate=0.5 mL/min, λ=254 nm, retention time: t=3.38 min.

FS061

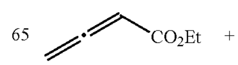

-continued

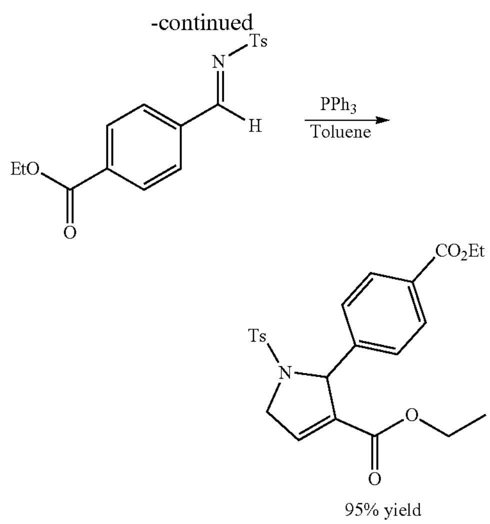

The imine (99 mg, 0.3 mmol) and triphenylphosphine (78.6 mg, 0.3 mmol) were dissolved in toluene. Ethyl buta-2,3-dienoate (40 mg, 0.36 mmol) was added dropwised. The mixture was stirred at room temperature overnight. Solvent was removed under vacuum and the residue was purified by flash chromatography to yield the title compound in 95% yield. The purity was checked by HPLC analysis using Poroshell 120 EC-C18 column and $H_2O/CH_3CN$ (20/80) as eluent: flow rate=0.5 mL/min, λ=254 nm, retention time: t=3.92 min.

FS076

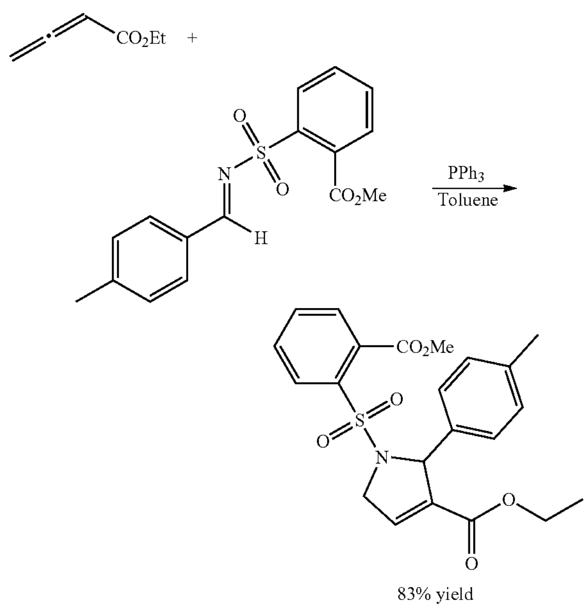

The imine (95 mg, 0.3 mmol) and triphenylphosphine (78.6 mg, 0.3 mmol) were dissolved in toluene. Ethyl buta-2,3-dienoate (40 mg, 0.36 mmol) was added dropwised. The mixture was stirred at room temperature overnight. Solvent was removed under vacuum and the residue was purified by flash chromatography to yield the title compound in 83% yield.

To a solution of 2-phenyl-1-tosyl-2,5-dihydro-1H-pyrrole-3-carboxylic acid (150 mg, 0.44 mmol) and 2-aminoethan-1-ol (35 μL, 0.57 mmol) in $CH_3CN$ (10 mL) was added HOBt (89 mg, 0.66 mmol), EDCI (126 mg, 0.66 mmol) and DIPEA (230 μL, 1.32 mmol) at 0° C. The reaction mixture was stirred at rt for 16 h. The reaction mixture was diluted with EtOAc, washed with 1N HCl, saturated $NaHCO_3$, brine, dried over $Na_2SO_4$, filtered and concentrated under reduced pressure. The residue was purified by column chromatography on silica gel to afford the title compound in 90% yield. The purity was checked by HPLC analysis using Poroshell 120 EC-C18 column and $H_2O/CH_3CN$ (20/80) as eluent: flow rate=0.5 mL/min, λ=254 nm, retention time: t=3.54 min.

FSO78

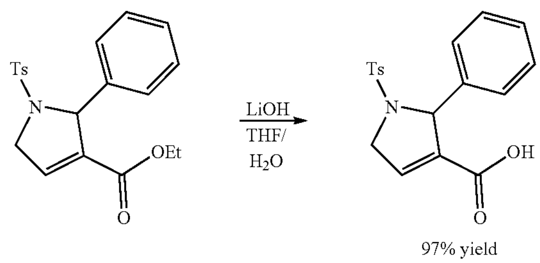 [SMILES: CCOC(=O)C1=CCN(S(=O)(=O)c2ccc(C)cc2)C1c1ccccc1 ; "LiOH" ; Cc1ccc(S(=O)(=O)N2CC=C(C(=O)O)C2c2ccccc2)cc1]

To a cooled (0° C.) stirred solution of ethyl 2-phenyl-1-tosyl-2,5-dihydro-1H-pyrrole-3-carboxylate (0.37 g, 1 mmol) in THF (5 mL) and $H_2O$ (5 mL) was added LiOH (48 mg, 2 mmol). After being stirred at room temperature for 1.5 h, the mixture was quenched with 2M aqueous HCl and extracted with EtOAc. The combined extracts were washed with saturated brine, dried over $Na_2SO_4$ and concentrated under reduced pressure to provide the product in 97% yield.

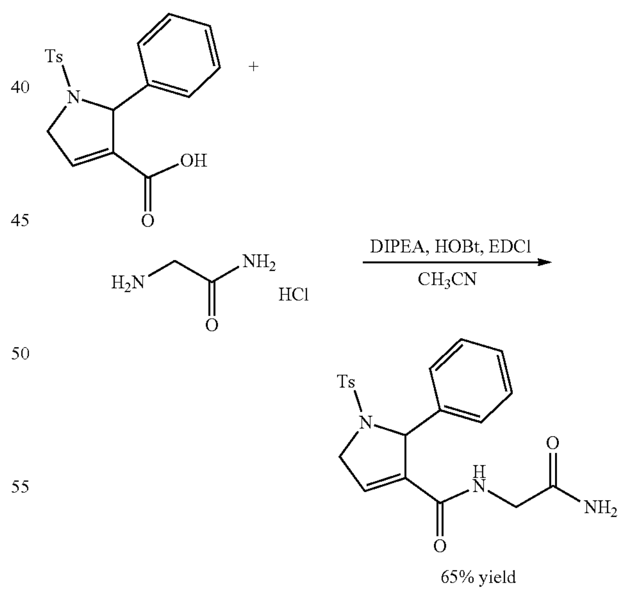

To a solution of 2-phenyl-1-tosyl-2,5-dihydro-1H-pyrrole-3-carboxylic acid (150 mg, 0.44 mmol) and 2-aminoacetamide hydrochloride (63 mg, 0.57 mmol) in $CH_3CN$ (10 mL) was added HOBt (89 mg, 0.66 mmol), EDCI (126 mg, 0.66 mmol) and DIPEA (230 μL, 1.32 mmol) at 0° C. The reaction mixture was stirred at rt for 16 h. The reaction mixture was diluted with EtOAc, washed with 1N HCl, saturated $NaHCO_3$, brine, dried over $Na_2SO_4$, filtered and concentrated under reduced pressure. The residue was purified by column chromatography on silica gel to afford the title compound in 64% yield. The purity was checked by HPLC analysis using Poroshell 120 EC-C18 column and $H_2O/CH_3CN$ (40/60) as eluent: flow rate=0.5 mL/min, λ=254 nm, retention time: t=2.63 min.

FS079

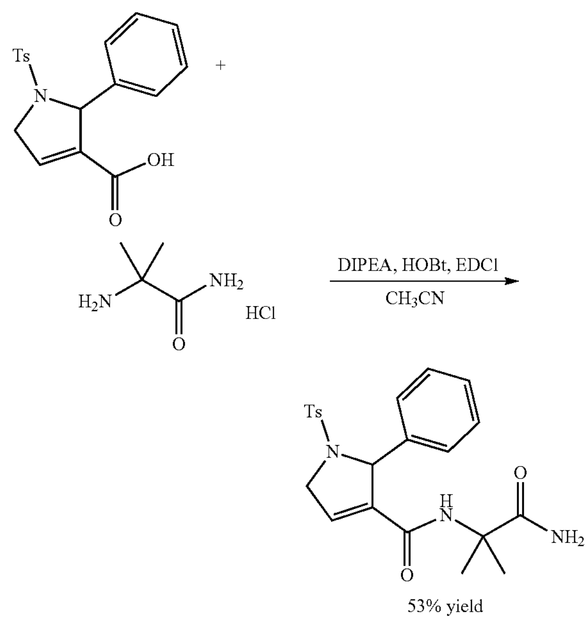

To a solution of 2-phenyl-1-tosyl-2,5-dihydro-1H-pyrrole-3-carboxylic acid (150 mg, 0.44 mmol) and 2-amino-2-methylpropanamide (58 mg, 0.57 mmol) in $CH_3CN$ (10 mL) was added HOBt (89 mg, 0.66 mmol), EDCI (126 mg, 0.66 mmol) and DIPEA (153 μL, 0.88 mmol) at 0° C. The reaction mixture was stirred at rt for 16 h. The reaction mixture was diluted with EtOAc, washed with 1N HCl, saturated $NaHCO_3$, brine, dried over $Na_2SO_4$, filtered and concentrated under reduced pressure. The residue was purified by column chromatography on silica gel to afford the title compound in 53% yield. The purity was checked by HPLC analysis using Poroshell 120 EC-C18 column and $H_2O/CH_3CN$ (40/60) as eluent: flow rate=0.5 mL/min, λ=254 nm, retention time: t=2.87 min.

FS080

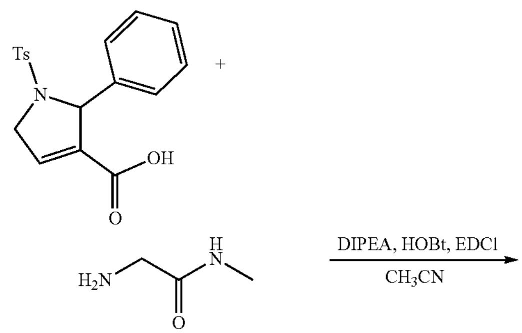

-continued

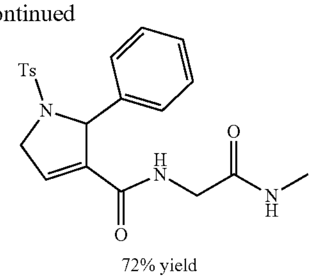

To a solution of 2-phenyl-1-tosyl-2,5-dihydro-1H-pyrrole-3-carboxylic acid (150 mg, 0.44 mmol) and 2-amino-N-methylacetamide (50 mg, 0.57 mmol) in $CH_3CN$ (10 mL) was added HOBt (89 mg, 0.66 mmol), EDCI (126 mg, 0.66 mmol) and DIPEA (153 μL, 0.88 mmol) at 0° C. The reaction mixture was stirred at rt for 16 h. The reaction mixture was diluted with EtOAc, washed with 1N HCl, saturated $NaHCO_3$, brine, dried over $Na_2SO_4$, filtered and concentrated under reduced pressure. The residue was purified by column chromatography on silica gel to afford the title compound in 72% yield. The purity was checked by HPLC analysis using Poroshell 120 EC-C18 column and $H_2O/CH_3CN$ (40/60) as eluent: flow rate=0.5 mL/min, λ=254 nm, retention time: t=6.53 min.

FS081

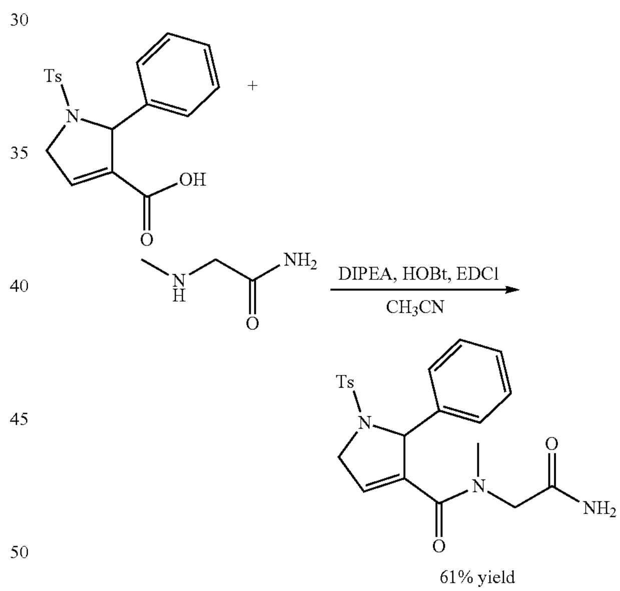

To a solution of 2-phenyl-1-tosyl-2,5-dihydro-1H-pyrrole-3-carboxylic acid (150 mg, 0.44 mmol) and 2-(methylamino)acetamide (50 mg, 0.57 mmol) in $CH_3CN$ (10 mL) was added HOBt (89 mg, 0.66 mmol), EDCI (126 mg, 0.66 mmol) and DIPEA (153 μL, 0.88 mmol) at 0° C. The reaction mixture was stirred at rt for 16 h. The reaction mixture was diluted with EtOAc, washed with 1N HCl, saturated $NaHCO_3$, brine, dried over $Na_2SO_4$, filtered and concentrated under reduced pressure. The residue was purified by column chromatography on silica gel to afford the title compound in 61% yield. The purity was checked by HPLC analysis using Poroshell 120 EC-C18 column and $H_2O/CH_3CN$ (40/60) as eluent: flow rate=0.5 mL/min, λ=254 nm, retention time: t=6.27 min.

FS082

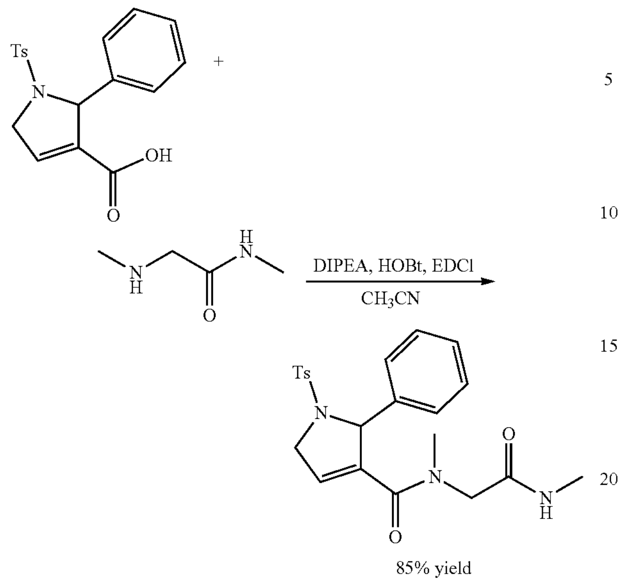

To a solution of 2-phenyl-1-tosyl-2,5-dihydro-1H-pyrrole-3-carboxylic acid (150 mg, 0.44 mmol) and N-methyl-2-(methylamino)acetamide (58.2 mg, 0.57 mmol) in $CH_3CN$ (10 mL) was added HOBt (89 mg, 0.66 mmol), EDCI (126.5 mg, 0.66 mmol) and DIPEA (230 μL, 1.32 mmol) at 0° C. The reaction mixture was stirred at rt for 16 h. The reaction mixture was diluted with EtOAc, washed with 1N HCl, saturated $NaHCO_3$, brine, dried over $Na_2SO_4$, filtered and concentrated under reduced pressure. The residue was purified by column chromatography on silica gel to afford the title compound in 85% yield. The purity was checked by HPLC analysis using Poroshell 120 EC-C18 column and $H_2O/CH_3CN$ (40/60) as eluent: flow rate=0.5 mL/min, λ=254 nm, retention time: t=7.21 min.

FS083

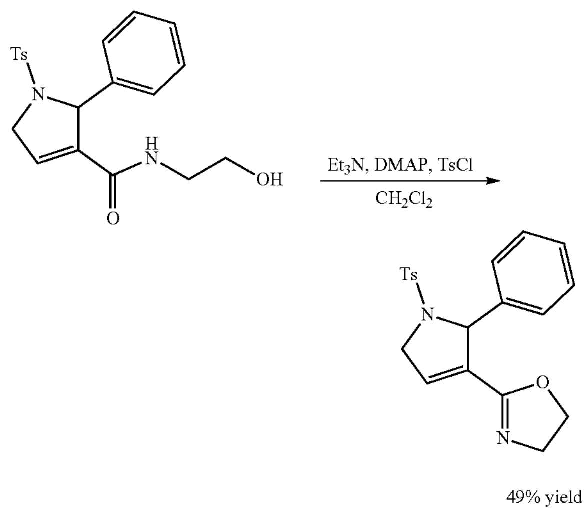

To a dried round bottomed flask was added the amide (73 mg, 0.19 mmol) and dry dichloromethane (3 mL). With stirring $Et_3N$ (50 μL, 0.36 mmol) was then added, followed by DMAP (4.64 mg, 0.038 mmol) and p-TsCl (61.6 mg, 0.323 mmol). The reaction mixture was allowed to stir at room temperature overnight, before being diluted with dichloromethane and water. The mixture was then transferred to a separating funnel and the layers partitioned. The aqueous layer was further extracted with dichloromethane. The combined organic layers were dried over anhydrous $Na_2SO_4$, filtered and the solvent was removed in vacuo. The crude residue was dissolved in MeOH (5 mL) and NaOH (22.8 mg, 0.57 mmol) were added in one portion. The reaction mixture was stirred at room temperature for 2-3 h before removing the solvent in vacuo. The residue was dissolved in dichloromethane and water, and transferred to a separating funnel. The layers were partitioned and the aqueous layer was further extracted with dichloromethane and ethyl acetate. The combined organic layers were dried over anhydrous $Na_2SO_4$, filtered and the solvent was removed in vacuo. The residue was purified by flash column chromatography on silica gel to afford the oxazoline products in 49% yield.

FS084

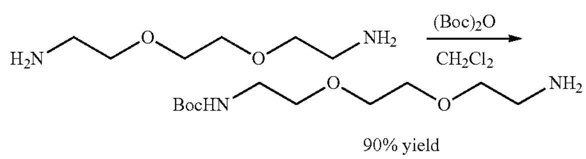

To a solution of 2,2'-(ethane-1,2-diylbis(oxy))bis(ethan-1-amine) (1.0 g, 6.75 mmol) in $CHCl_3$ (20 mL), a solution of di-tert-butyl dicarbonate (148 mg, 0.78 mmol) in $CHCl_3$ (20 mL) was added dropwise at 0° C. under inert atmosphere. At the end of the addition, the reaction mixture was allowed to warm up to rt and was stirred for overnight. After that time, solvents were evaporated, water (20 mL) was added, and the mixture was extracted with $CH_2Cl2$. The combined organic fractions were dried over $Na_2SO_4$ and evaporated to afford the title compound in 90% yield.

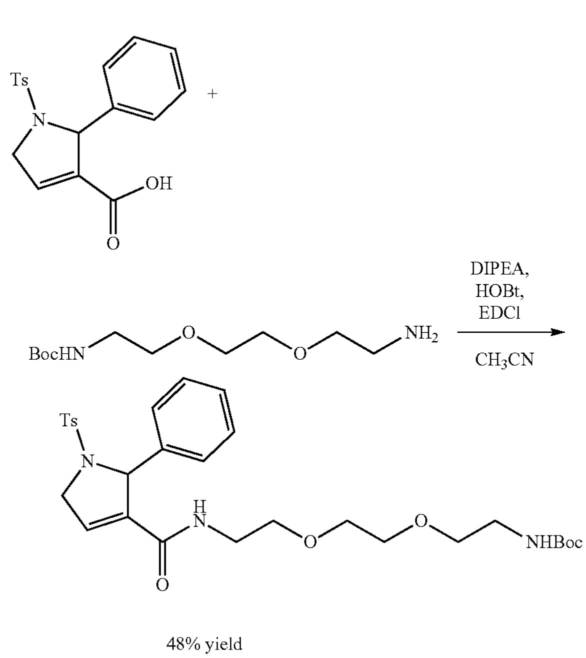

To a solution of 2-phenyl-1-tosyl-2,5-dihydro-1H-pyrrole-3-carboxylic acid (150 mg, 0.44 mmol) and tert-butyl (2-(2-(2-aminoethoxy)ethoxy)ethyl)carbamate (35 μL, 0.57 mmol) in $CH_3CN$ (10 mL) was added HOBt (89 mg, 0.66 mmol), EDCI (126 mg, 0.66 mmol) and DIPEA (230 μL, 1.32 mmol) at 0° C. The reaction mixture was stirred at rt for 16 h. The reaction mixture was diluted with EtOAc, washed with 1N HCl, saturated $NaHCO_3$, brine, dried over $Na_2SO_4$, filtered and concentrated under reduced pressure. The residue was purified by column chromatography on silica gel to afford the title compound in 90% yield.

FS105

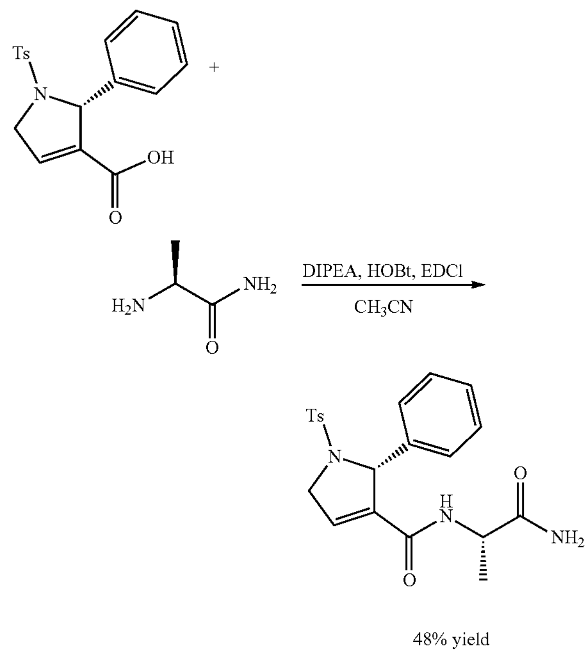

To a solution of (R)-2-phenyl-1-tosyl-2,5-dihydro-1H-pyrrole-3-carboxylic acid (75 mg, 0.22 mmol) and (S)-2-aminopropanamide (50 mg, 0.57 mmol) in $CH_3CN$ (5 mL) was added HOBt (45 mg, 0.33 mmol), EDCI (63 mg, 0.33 mmol) and DIPEA (115 μL, 0.66 mmol) at 0° C. The reaction mixture was stirred at rt for 16 h. The reaction mixture was diluted with EtOAc, washed with 1N HCl, saturated $NaHCO_3$, brine, dried over $Na_2SO_4$, filtered and concentrated under reduced pressure. The residue was purified by column chromatography on silica gel to afford the title compound in 48% yield. The purity was checked by HPLC analysis using Poroshell 120 EC-C18 column and $H_2O/CH_3CN$ (40/60) as eluent: flow rate=0.5 mL/min, λ=254 nm, retention time: t=6.77 min.

FS106

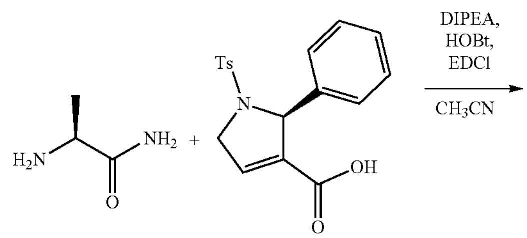

-continued

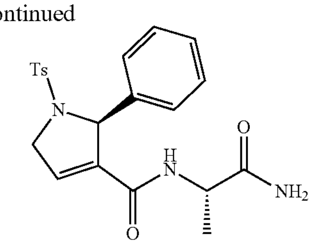

50% yield

To a solution of (S)-2-phenyl-1-tosyl-2,5-dihydro-1H-pyrrole-3-carboxylic acid (75 mg, 0.22 mmol) and (S)-2-aminopropanamide (50 mg, 0.57 mmol) in $CH_3CN$ (5 mL) was added HOBt (45 mg, 0.33 mmol), EDCI (63 mg, 0.33 mmol) and DIPEA (115 μL, 0.66 mmol) at 0° C. The reaction mixture was stirred at rt for 16 h. The reaction mixture was diluted with EtOAc, washed with 1N HCl, saturated $NaHCO_3$, brine, dried over $Na_2SO_4$, filtered and concentrated under reduced pressure. The residue was purified by column chromatography on silica gel to afford the title compound in 50% yield.The purity was checked by HPLC analysis using Poroshell 120 EC-C18 column and $H_2O/CH_3CN$ (40/60) as eluent: flow rate=0.5 mL/min, λ=254 nm, retention time: t=6.45 min.

FS107

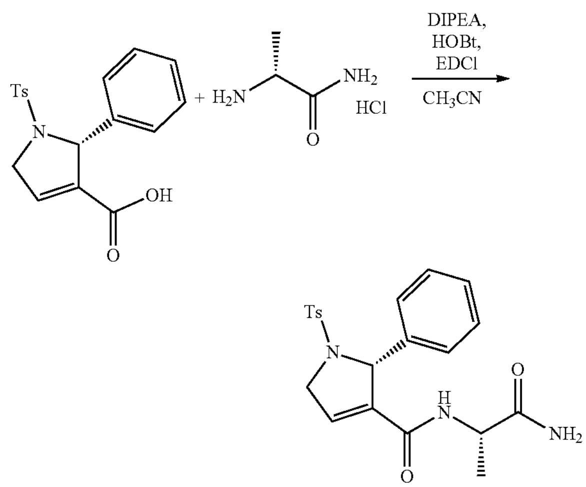

66% yield

To a solution of (R)-2-phenyl-1-tosyl-2,5-dihydro-1H-pyrrole-3-carboxylic acid (75 mg, 0.22 mmol) and (R)-2-aminopropanamide (36 mg, 0.29 mmol) in $CH_3CN$ (5 mL) was added HOBt (45 mg, 0.33 mmol), EDCI (63 mg, 0.33 mmol) and DIPEA (115 μL, 0.66 mmol) at 0° C. The reaction mixture was stirred at rt for 16 h. The reaction mixture was diluted with EtOAc, washed with 1N HCl, saturated $NaHCO_3$, brine, dried over $Na_2SO_4$, filtered and concentrated under reduced pressure. The residue was purified by column chromatography on silica gel to afford the title compound in 66% yield. The purity was checked by HPLC analysis using Poroshell 120 EC-C18 column and $H_2O/CH_3CN$ (40/60) as eluent: flow rate=0.5 mL/min, λ=254 nm, retention time: t=6.70 min.

FS108

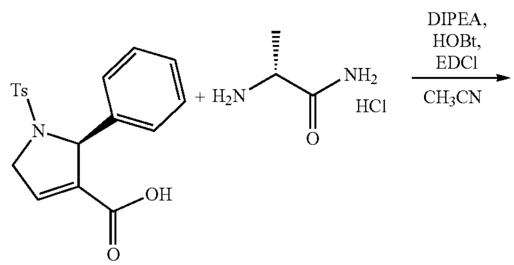

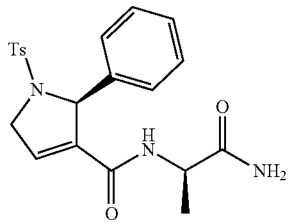

71% yield

To a solution of (S)-2-phenyl-1-tosyl-2, 5-dihydro-1H-pyrrole-3-carboxylic acid (75 mg, 0.22 mmol) and (R)-2-aminopropanamide (36 mg, 0.29 mmol) in $CH_3CN$ (5 mL) was added HOBt (45 mg, 0.33 mmol), EDCI (63 mg, 0.33 mmol) and DIPEA (115 μL, 0.66 mmol) at 0° C. The reaction mixture was stirred at rt for 16 h. The reaction mixture was diluted with EtOAc, washed with 1N HCl, saturated $NaHCO_3$, brine, dried over $Na_2SO_4$, filtered and concentrated under reduced pressure. The residue was purified by column chromatography on silica gel to afford the title compound in 71% yield. The purity was checked by HPLC analysis using Poroshell 120 EC-C18 column and $H_2O/CH_3CN$ (40/60) as eluent: flow rate=0.5 mL/min, λ=254 nm, retention time: t=6.66 min.

FS109

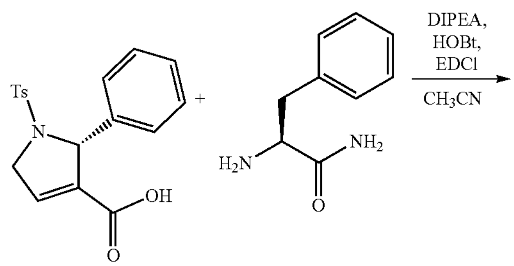

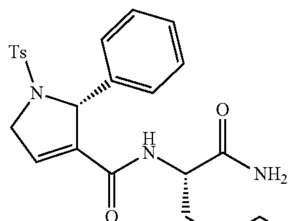

46% yield

To a solution of (R)-2-phenyl-1-tosyl-2,5-dihydro-1H-pyrrole-3-carboxylic acid (75 mg, 0.22 mmol) and (S)-2-amino-3-phenylpropanamide (93.5 mg, 0.57 mmol) in $CH_3CN$ (5 mL) was added HOBt (45 mg, 0.33 mmol), EDCI (63 mg, 0.33 mmol) and DIPEA (115 μL, 0.66 mmol) at 0° C. The reaction mixture was stirred at rt for 16 h. The reaction mixture was diluted with EtOAc, washed with 1N HCl, saturated $NaHCO_3$, brine, dried over $Na_2SO_4$, filtered and concentrated under reduced pressure. The residue was purified by column chromatography on silica gel to afford the title compound in 46% yield. The purity was checked by HPLC analysis using Poroshell 120 EC-C18 column and $H_2O/CH_3CN$ (40/60) as eluent: flow rate=0.5 mL/min, λ=254 nm, retention time: t=3.79 min.

FS110

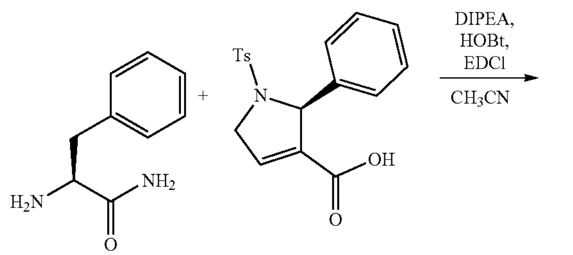

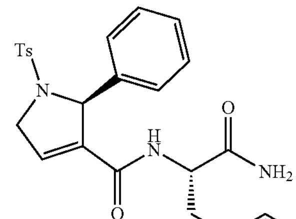

49% yield

To a solution of (S)-2-phenyl-1-tosyl-2, 5-dihydro-1H-pyrrole-3-carboxylic acid (75 mg, 0.22 mmol) and (S)-2-amino-3-phenylpropanamide (93.5 mg, 0.57 mmol) in $CH_3CN$ (5 mL) was added HOBt (45 mg, 0.33 mmol), EDCI (63 mg, 0.33 mmol) and DIPEA (115 μL, 0.66 mmol) at 0° C. The reaction mixture was stirred at rt for 16 h. The reaction mixture was diluted with EtOAc, washed with 1N HCl, saturated $NaHCO_3$, brine, dried over $Na_2SO_4$, filtered and concentrated under reduced pressure. The residue was purified by column chromatography on silica gel to afford the title compound in 49% yield. The purity was checked by HPLC analysis using Poroshell 120 EC-C18 column and $H_2O/CH_3CN$ (40/60) as eluent: flow rate=0.5 mL/min, λ=254 nm, retention time: t=3.81 min.

FS111

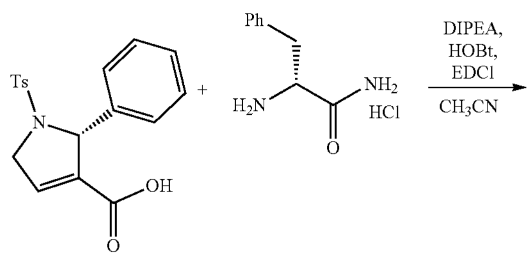

-continued

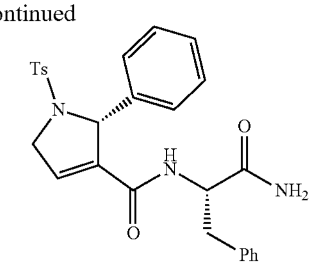

58% yield

To a solution of (R)-2-phenyl-1-tosyl-2,5-dihydro-1H-pyrrole-3-carboxylic acid (75 mg, 0.22 mmol) and (R)-2-amino-3-phenylpropanamide (58 mg, 0.29 mmol) in $CH_3CN$ (5 mL) was added HOBt (45 mg, 0.33 mmol), EDCI (63 mg, 0.33 mmol) and DIPEA (115 μL, 0.66 mmol) at 0° C. The reaction mixture was stirred at rt for 16 h. The reaction mixture was diluted with EtOAc, washed with 1N HCl, saturated $NaHCO_3$, brine, dried over $Na_2SO_4$, filtered and concentrated under reduced pressure. The residue was purified by column chromatography on silica gel to afford the title compound in 58% yield. The purity was checked by HPLC analysis using Poroshell 120 EC-C18 column and $H_2O/CH_3CN$ (40/60) as eluent: flow rate=0.5 mL/min, λ=254 nm, retention time: t=3.76 min.

FS112

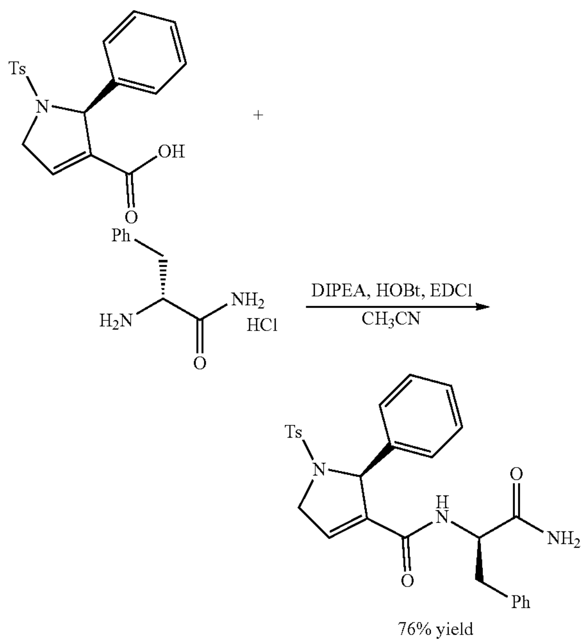

To a solution of (S)-2-phenyl-1-tosyl-2, 5-dihydro-1H-pyrrole-3-carboxylic acid (75 mg, 0.22 mmol) and (R)-2-amino-3-phenylpropanamide (58 mg, 0.29 mmol) in $CH_3CN$ (5 mL) was added HOBt (45 mg, 0.33 mmol), EDCI (63 mg, 0.33 mmol) and DIPEA (115 μL, 0.66 mmol) at 0° C. The reaction mixture was stirred at rt for 16 h. The reaction mixture was diluted with EtOAc, washed with 1N HCl, saturated $NaHCO_3$, brine, dried over $Na_2SO_4$, filtered and concentrated under reduced pressure. The residue was purified by column chromatography on silica gel to afford the title compound in 76% yield. The purity was checked by HPLC analysis using Poroshell 120 EC-C18 column and $H_2O/CH_3CN$ (40/60) as eluent: flow rate=0.5 mL/min, λ=254 nm, retention time: t=3.74 min.

FS115

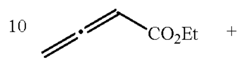

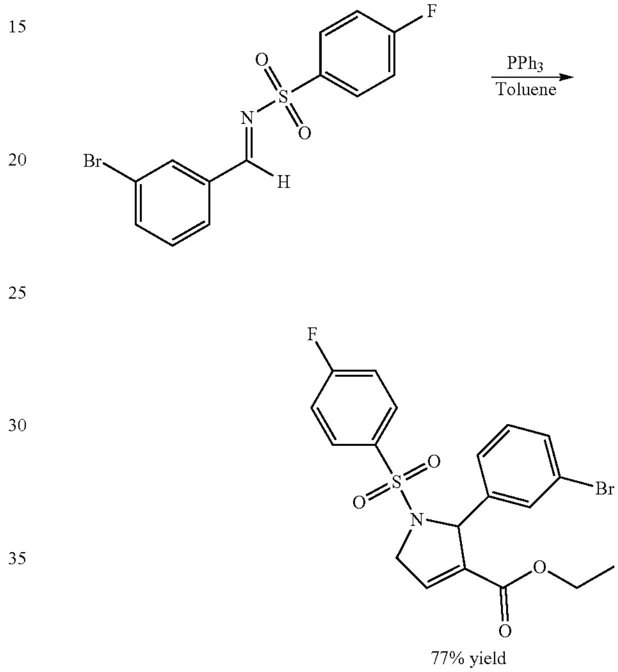

The imine (102.6 mg, 0.3 mmol) and triphenylphosphine (78.6 mg, 0.3 mmol) were dissolved in toluene. Ethyl buta-2,3-dienoate (40 mg, 0.36 mmol) was added dropwised. The mixture was stirred at room temperature overnight. Solvent was removed under vacuum and the residue was purified by flash chromatography to yield the title compound in 77% yield. The purity was checked by HPLC analysis using Poroshell 120 EC-C18 column and $H_2O/CH_3CN$ (20/80) as eluent: flow rate=0.5 mL/min, λ=254 nm, retention time: t=4.03 min.

FS133

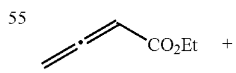

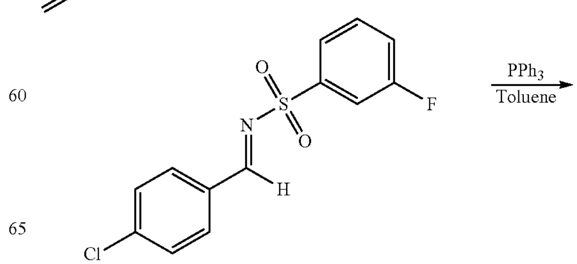

-continued

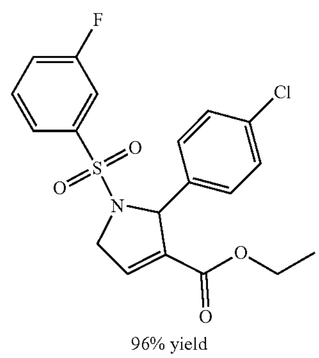

The imine (89.3 mg, 0.3 mmol) and triphenylphosphine (78.6 mg, 0.3 mmol) were dissolved in toluene. Ethyl buta-2,3-dienoate (40 mg, 0.36 mmol) was added dropwised. The mixture was stirred at room temperature overnight. Solvent was removed under vacuum and the residue was purified by flash chromatography to yield the title compound in 96% yield. The purity was checked by HPLC analysis using Poroshell 120 EC-C18 column and $H_2O/CH_3CN$ (20/80) as eluent: flow rate=0.5 mL/min, λ=254 nm, retention time: t=3.94 min.

FS134

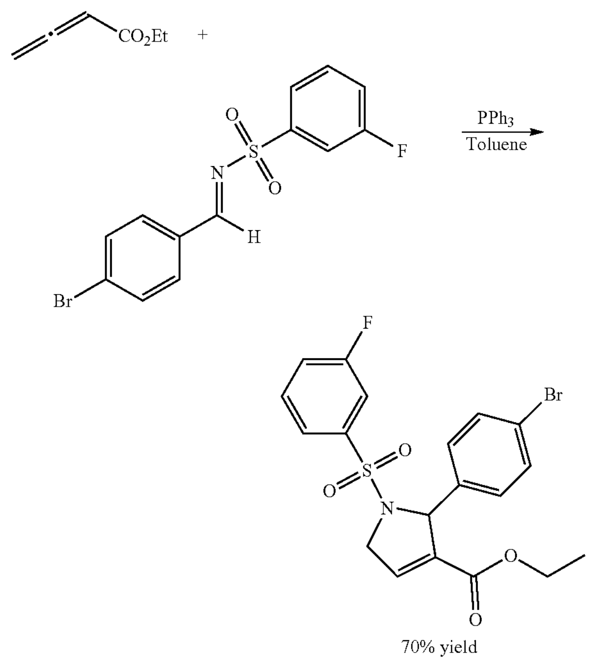

The imine (102.6 mg, 0.3 mmol) and triphenylphosphine (78.6 mg, 0.3 mmol) were dissolved in toluene. Ethyl buta-2,3-dienoate (40 mg, 0.36 mmol) was added dropwised. The mixture was stirred at room temperature overnight. Solvent was removed under vacuum and the residue was purified by flash chromatography to yield the title compound in 70% yield. The purity was checked by HPLC analysis using Poroshell 120 EC-C18 column and $H_2O/CH_3CN$ (20/80) as eluent: flow rate=0.5 mL/min, λ=254 nm, retention time: t=4.15 min.

FS135

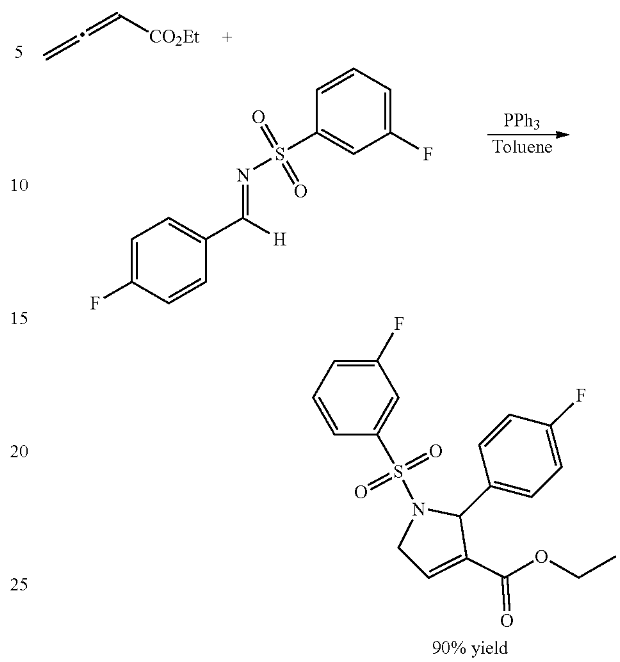

The imine (84.4 mg, 0.3 mmol) and triphenylphosphine (78.6 mg, 0.3 mmol) were dissolved in toluene. Ethyl buta-2,3-dienoate (40 mg, 0.36 mmol) was added dropwised. The mixture was stirred at room temperature overnight. Solvent was removed under vacuum and the residue was purified by flash chromatography to yield the title compound in 90% yield. The purity was checked by HPLC analysis using Poroshell 120 EC-C18 column and $H_2O/CH_3CN$ (20/80) as eluent: flow rate=0.5 mL/min, λ=254 nm, retention time: t=3.45 min.

FS136

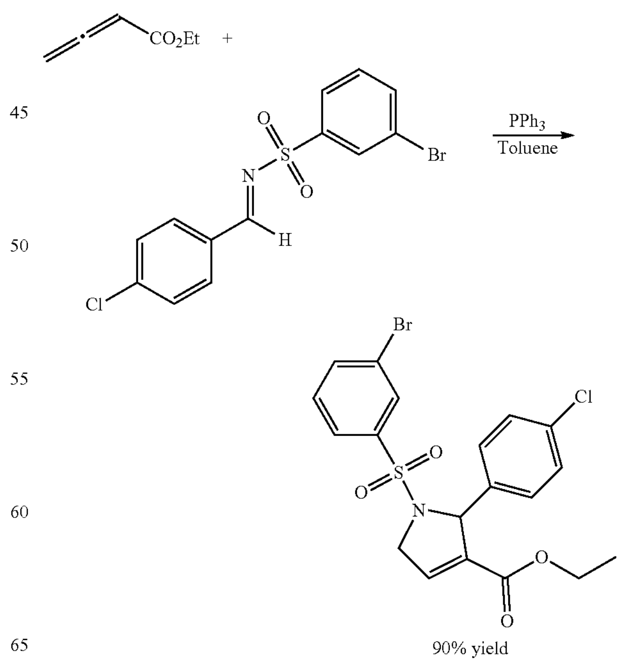

The imine (107.6 mg, 0.3 mmol) and triphenylphosphine (78.6 mg, 0.3 mmol) were dissolved in toluene. Ethyl buta-2,3-dienoate (40 mg, 0.36 mmol) was added dropwised. The mixture was stirred at room temperature overnight. Solvent was removed under vacuum and the residue was purified by flash chromatography to yield the title compound in 90% yield. The purity was checked by HPLC analysis using Poroshell 120 EC-C18 column and $H_2O$/$CH_3CN$ (20/80) as eluent: flow rate=0.5 mL/min, =254 nm, retention time: t=4.89 min.

FS137

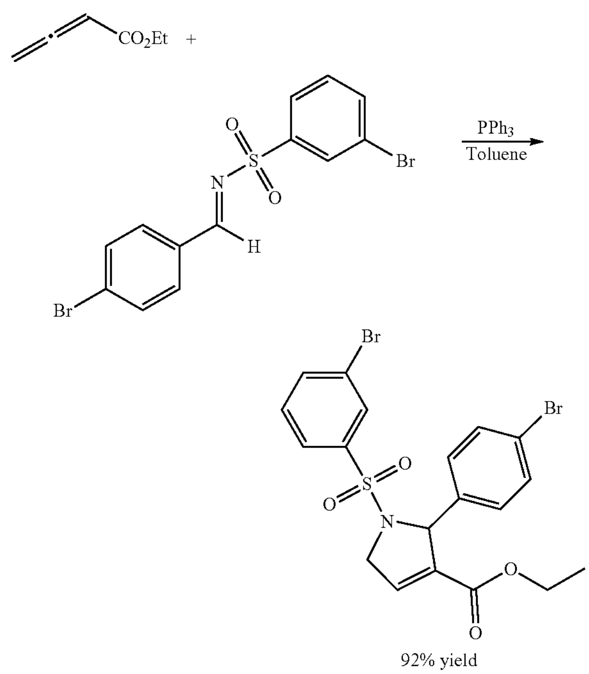

The imine (120.9 mg, 0.3 mmol) and triphenylphosphine (78.6 mg, 0.3 mmol) were dissolved in toluene. Ethyl buta-2,3-dienoate (40 mg, 0.36 mmol) was added dropwised. The mixture was stirred at room temperature overnight. Solvent was removed under vacuum and the residue was purified by flash chromatography to yield the title compound in 90% yield. The purity was checked by HPLC analysis using Poroshell 120 EC-C18 column and $H_2O$/$CH_3CN$ (20/80) as eluent: flow rate=0.5 mL/min, $\lambda$=254 nm, retention time: t=5.12 min.

FS138

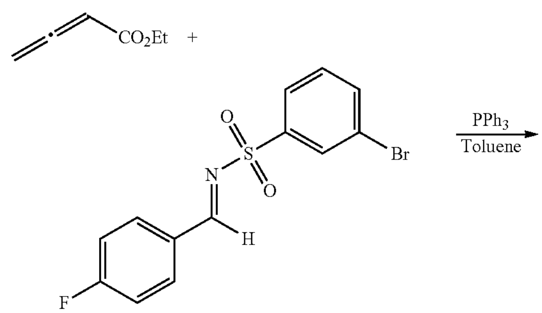

-continued

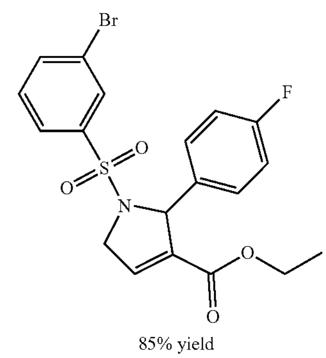

The imine (102.7 mg, 0.3 mmol) and triphenylphosphine (78.6 mg, 0.3 mmol) were dissolved in toluene. Ethyl buta-2,3-dienoate (40 mg, 0.36 mmol) was added dropwised. The mixture was stirred at room temperature overnight. Solvent was removed under vacuum and the residue was purified by flash chromatography to yield the title compound in 85% yield. The purity was checked by HPLC analysis using Poroshell 120 EC-C18 column and $H_2O$/$CH_3CN$ (20/80) as eluent: flow rate=0.5 mL/min, $\lambda$=254 nm, retention time: t=4.11 min.

FS143

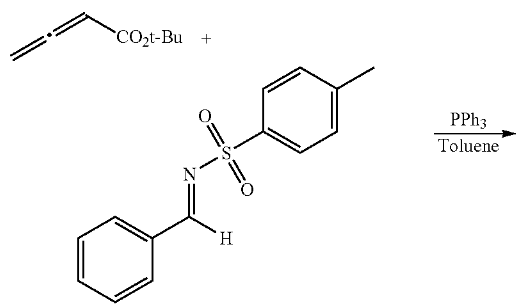

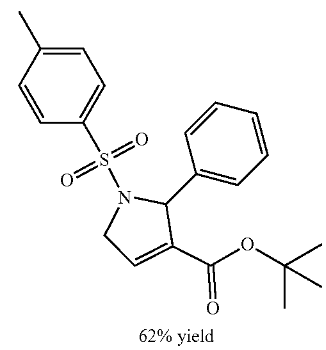

The imine (102.7 mg, 0.3 mmol) and triphenylphosphine (78.6 mg, 0.3 mmol) were dissolved in toluene. tert-butyl buta-2,3-dienoate (50 mg, 0.36 mmol) was added dropwised. The mixture was stirred at room temperature overnight. Solvent was removed under vacuum and the residue was purified by flash chromatography to yield the title compound in 62% yield.

FS144 (Procedure A)

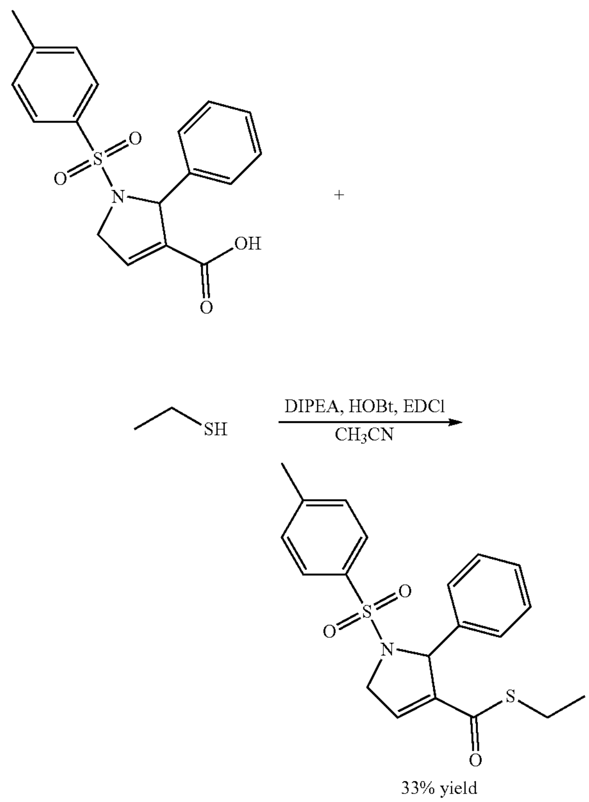

To a solution of 2-phenyl-1-tosyl-2,5-dihydro-1H-pyrrole-3-carboxylic acid (150 mg, 0.44 mmol) and ethanethiol (22 μL, 0.32 mmol) in $CH_3CN$ (10 mL) was added HOBt (89 mg, 0.66 mmol), EDCI (126 mg, 0.66 mmol) and DIPEA (230 μL, 1.32 mmol) at 0° C. The reaction mixture was stirred at rt for 16 h. The reaction mixture was diluted with EtOAc, washed with 1N HCl, saturated $NaHCO_3$, brine, dried over $Na_2SO_4$, filtered and concentrated under reduced pressure. The residue was purified by column chromatography on silica gel to afford the title compound in 33% yield.

FS144 (Procedure B)

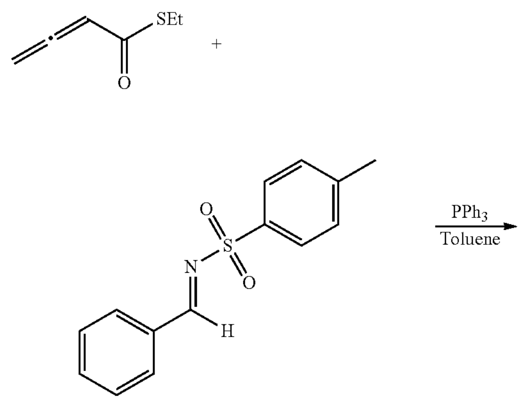

-continued

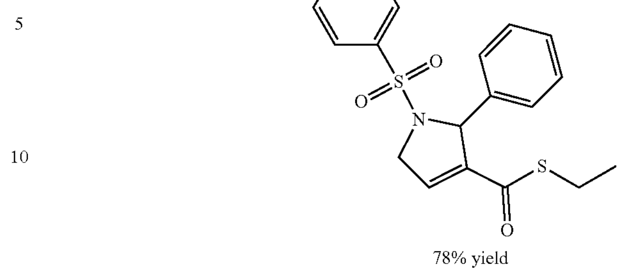

To a solution of S-ethyl buta-2,3-dienethioate (0.1 g, 0.78 mmol) and imine (0.18 g, 0.71 mmol) in benzene (8 mL) was added $PPh_3$ (18.6 mg, 0.071 mmol) under ice bath. The reaction mixture was then warmed to room temperature and stirred overnight. This solution was concentrated and purified by FCC (hex/EA: 3/1) to give the title compound as white solid (0.23 g, 77%). $^1H$ NMR (300 MHz, $CDCl_3$) δ 7.42 (d, J=8.3 Hz, 2H), 7.25-7.18 (m, 5H), 7.14 (d, J=8.0 Hz, 2H), 6.74 (dd, J=3.8, 2.0 Hz, 1H), 5.85-5.79 (m, 1H), 4.52 (dt, J=17.2, 2.5 Hz, 1H), 4.38 (ddd, J=17.2, 5.6, 2.0 Hz, 1H), 2.91-2.67 (m, 2H), 2.37 (s, 3H), 1.15 (t, J=7.4 Hz, 3H). $^{13}C$ NMR (100 MHz, $CDCl_3$) δ 186.2, 143.5, 142.7, 139.1, 135.6, 133.1, 129.6, 128.5, 128.2, 128.0, 127.2, 69.1, 55.0, 23.3, 21.6, 14.5.

Preparation of S-ethyl buta-2, 3-dienethioate

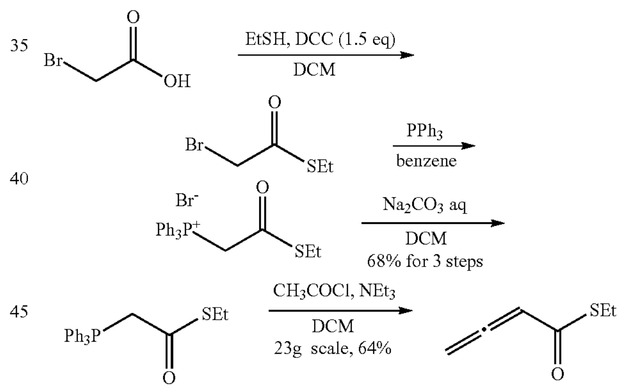

To a stirred solution of 2-bromoacetic acid (14.0 g, 101.5 mmol), ethanethiol (7.4 mL, 101.5 mmol) and 4-dimethylaminepyridine (DMAP, 0.12 g, 0.1 mmol) in DCM (400 mL) was added DCC (N,N'-dicyclohexylcarbodiimide, 21.7 g, 105.2 mmol) under ice bath. The reaction mixture was slowly warmed to room temperature and stirred overnight. The solution was filtered through Celite, and washed several times with DCM. The filtrate was concentrated, dissolved in hexane (100 mL), filtered through Celite, and washed with hexane. The filtrate was concentrated to give a light-yellow oil. This crude oil was used in the next step without further purification.

The crude oil above and $PPh_3$ (27.8 g, 106.6 mmol) were dissolved in benzene (150 mL) and allowed to stand at room temperature for three days. The white crystals formed in the reaction flask was filtered and washed with benzene to yield the phosphonium salts. This phosphonium salts was dissolved in DCM (150 mL) and stirred with a solution of $Na_2CO_3$ solution (10% w/w, 100 mL) for 1 hour. The aqueous solution was exacted with DCM, washed with brine, dried over $Na_2SO_4$, and concentrated to give a crude solid. This crude solid was triturated with DCM/Hexane (1:20) to give S-ethyl 2-(triphenyl-$\lambda^5$-phosphanylidene)ethanethioate as white solid (25 g, 68% yield for 3 steps). $^1H$ NMR (400 MHz, $CDCl_3$) δ 7.66-7.42 (m, 15H), 3.66 (d, J=22.3 Hz, 1H), 2.84 (q, J=7.4 Hz, 2H), 1.25 (t, J=7.4 Hz, 3H). $^{31}P$ NMR (162 MHz, $CDCl_3$) δ 13.51.

To s solution of S-ethyl 2-(triphenyl-$\lambda^5$-phosphanylidene) ethanethioate (23.0 g, 63.0 mmol) and triethylamine (6.4 g, 63.0 mmol) in DCM (180 mL) was added a solution of acetyl chloride (5.0 g, 63.0 mmol) in DCM (40 mL) dropwise (about 1 mL/min) under ice bath. This reaction mixture was stirred overnight, and pentane (200 mL) was added. The resulting mixture was filtered through Celite and concentrated under vacuum and low temperature (the temperature of bath was below 10° C.). The crude product was purified by FCC (pentane/$Et_2O$: 10/1) to the title compound S-ethyl buta-2,3-dienethioate as yellow oil (5.1 g, 64%). $^1H$ NMR (300 MHz, $CDCl_3$) δ 5.91 (t, J=6.5 Hz, 1H), 5.33 (d, J=6.5 Hz, 2H), 2.93 (q, J=7.4 Hz, 2H), 1.27 (t, J=7.4 Hz, 3H). $^{13}C$ NMR (100 MHz, $CDCl_3$) δ 214.4, 189.6, 96.2, 81.6, 23.4, 14.9. The purity was checked by HPLC analysis using Poroshell 120 EC-C18 column and $H_2O/CH_3CN$ (20/80) as eluent: flow rate=0.5 mL/min, λ=254 nm, retention time: t=4.43 min.

FS145 (Procedure A)

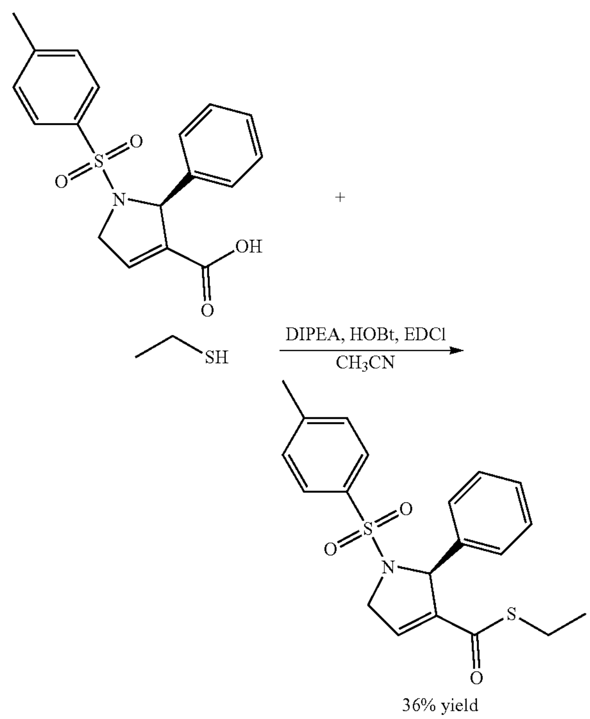

To a solution of (S)-2-phenyl-1-tosyl-2,5-dihydro-1H-pyrrole-3-carboxylic acid (150 mg, 0.44 mmol) and ethanethiol (22 μL, 0.32 mmol) in $CH_3CN$ (10 mL) was added HOBt (89 mg, 0.66 mmol), EDCI (126 mg, 0.66 mmol) and DIPEA (230 μL, 1.32 mmol) at 0° C. The reaction mixture was stirred at rt for 16 h. The reaction mixture was diluted with EtOAc, washed with 1N HCl, saturated $NaHCO_3$, brine, dried over $Na_2SO_4$, filtered and concentrated under reduced pressure. The residue was purified by column chromatography on silica gel to afford the title compound in 36% yield.

FS145 (Procedure B)

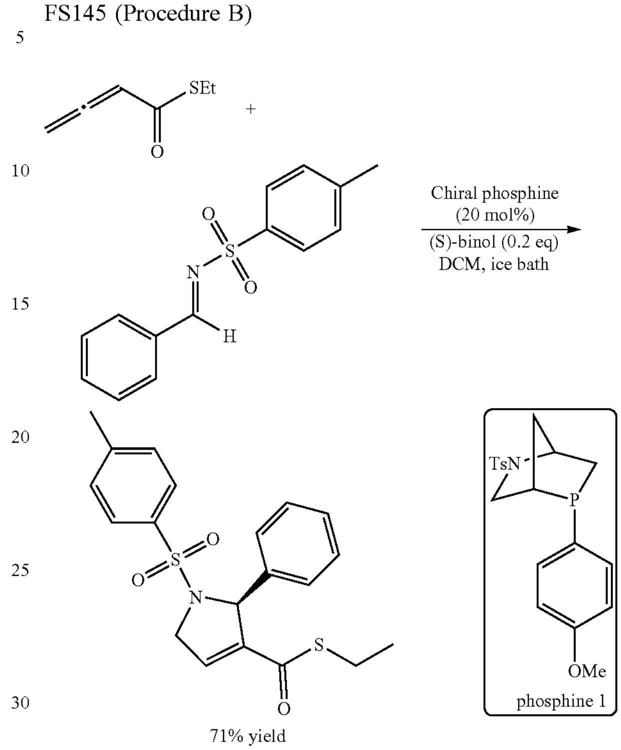

To a solution of S-ethyl buta-2,3-dienethioate (0.1 g, 0.78 mmol, 1.1 equivl), imine (0.18 g, 0.71 mmol, 1.0 equiv) and (S)-binol (22.9 mg, 0.08 mmol, 0.2 equiv) in DCM (0.05 M) was added chiral phosphine 1 (0.2 equiv) under ice bath. The reaction mixture was then slowly warmed to room temperature and stirred overnight. This solution was concentrated and purified by FCC (hex/EA: 3/1) to give the title compound as white solid (110 mg, 71% yield). 96.8% ee (after recrystallization from hexane/ethyl acetate, 98.5% ee was obtained), the ee value was determined by REGIS (R, R)-DACH, DNB column, hexane:DCM=40:60, 2 mL/min, 254 nm, $t_R$ (minor)=5.79 min, $t_R$ (major)=7.29 min. $[a]^{23.6}_D$+214.0 (c 0.8, DCM). The purity was checked by HPLC analysis using Poroshell 120 EC-C18 column and $H_2O/CH_3CN$ (20/80) as eluent: flow rate=0.5 mL/min, λ=254 nm, retention time: t=4.38 min.

FS146 (Procedure A)

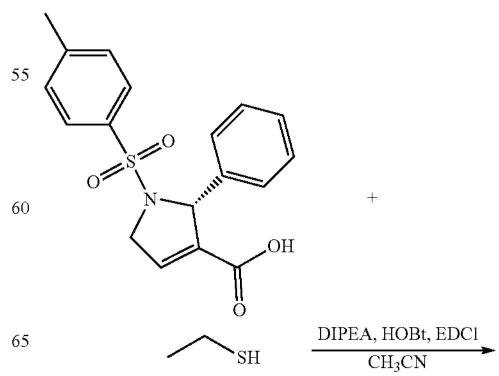

-continued

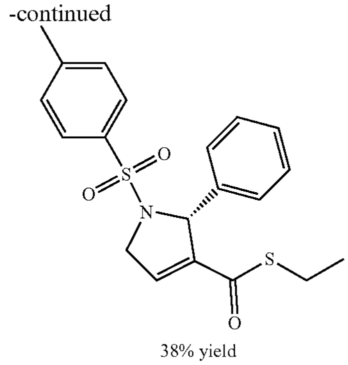

38% yield

To a solution of (R)-2-phenyl-1-tosyl-2,5-dihydro-1H-pyrrole-3-carboxylic acid (150 mg, 0.44 mmol) and ethanethiol (22 μL, 0.32 mmol) in $CH_3CN$ (10 mL) was added HOBt (89 mg, 0.66 mmol), EDCI (126 mg, 0.66 mmol) and DIPEA (230 μL, 1.32 mmol) at 0° C. The reaction mixture was stirred at rt for 16 h. The reaction mixture was diluted with EtOAc, washed with 1N HCl, saturated $NaHCO_3$, brine, dried over $Na_2SO_4$, filtered and concentrated under reduced pressure. The residue was purified by column chromatography on silica gel to afford the title compound in 38% yield.

FS146 (Procedure B)

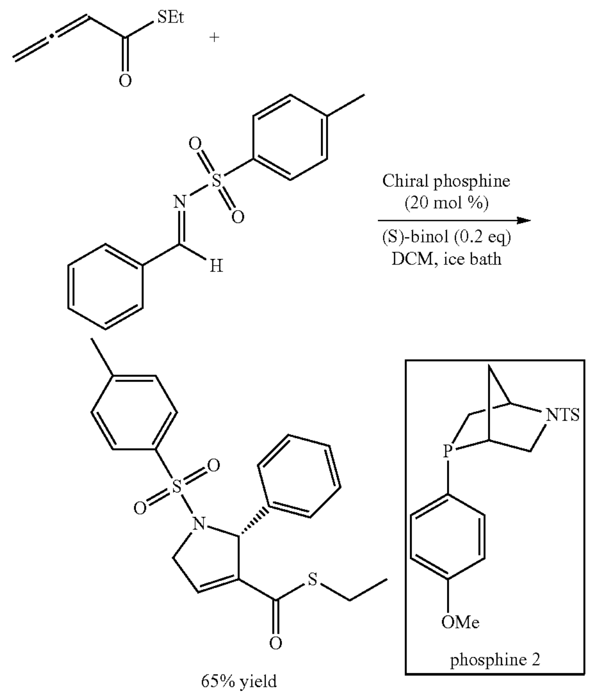

To a solution of S-ethyl buta-2,3-dienethioate (0.1 g, 0.78 mmol, 1.1 equivl), imine (0.18 g, 0.71 mmol, 1.0 equiv) and (S)-binol (22.9 mg, 0.08 mmol, 0.2 equiv) in DCM (0.05 M) was added chiral phosphine 2 (0.2 equiv) under ice bath. The reaction mixture was then slowly warmed to room temperature and stirred overnight. This solution was concentrated and purified by FCC (hex/EA: 3/1) to give the title compound as white solid (100 mg, 65% yield). 97.5% ee (after recrystallization from hexane/ethyl acetate, >99% ee was obtained), the ee value was determined by REGIS (R, R)-DACH, DNB column, hexane:DCM=40:60, 2 mL/min, 254 nm, $t_R$ (major)=5.61 min, $t_R$ (minor)=7.56 min. $[\alpha]^{25}_D$−221.5 (c 0.8, DCM). The purity was checked by HPLC analysis using Poroshell 120 EC-C18 column and $H_2O/CH_3CN$ (20/80) as eluent: flow rate=0.5 mL/min, λ=254 nm, retention time: t=4.37 min.

FS149

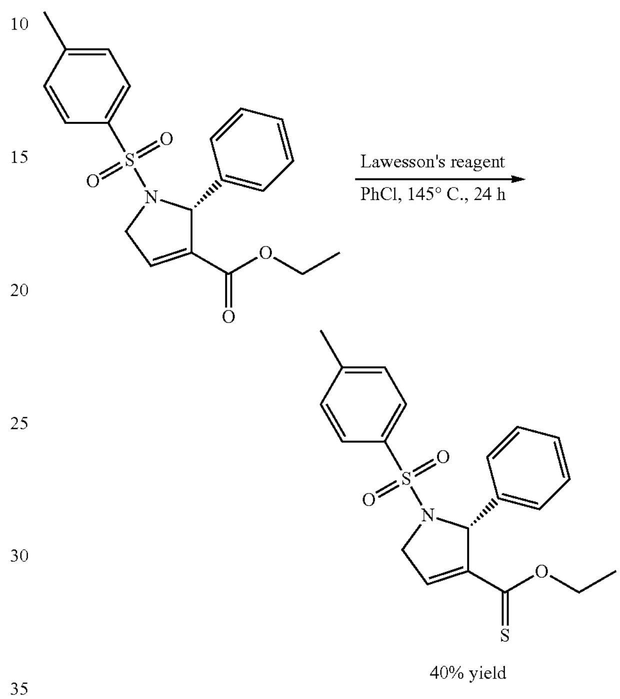

To a solution of ethyl 2-phenyl-1-tosyl-2,5-dihydro-1H-pyrrole-3-carboxylate (50 mg, 0.137 mmol) in PhCl (2 mL) was added Lawesson's reagent (220 mg, 0.543 mmol). The reaction mixture was then heated at 145° C. for 24 h. The solution was directly loaded on silica gel column and purified by hexane/EA (10/1 to 5/1) to give a yellow residue. This yellow residue was further purified by PTLC (hexane/EA: 4/1) to afford the title compound as yellow solid (21.2 mg, 40% yield). $^1$HNMR (300 MHz, $CDCl_3$) δ 7.37 (d, J=8.3 Hz, 2H), 7.24-7.15 (m, 5H), 7.11 (d, J=8.0 Hz, 2H), 6.85 (dd, J=3.7, 2.3 Hz, 1H), 5.98-5.88 (m, 1H), 4.48 (dt, J=17.6, 2.4 Hz, 1H), 4.39-4.24 (m, 3H), 2.35 (s, 3H), 1.21 (t, J=7.1 Hz, 3H). $^{13}$C NMR (101 MHz, $CDCl_3$) δ 203.8, 143.6, 143.2, 139.6, 136.0, 133.0, 129.5, 128.4, 128.2, 128.0, 127.2, 69.8, 67.8 54.9, 21.6, 13.5.

FS150

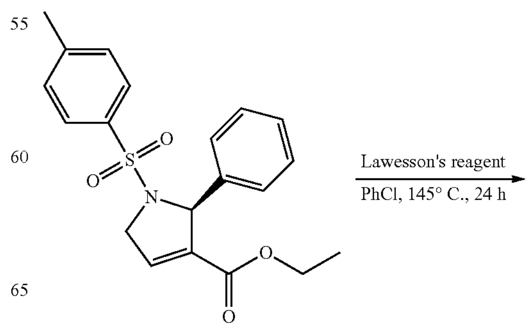

-continued

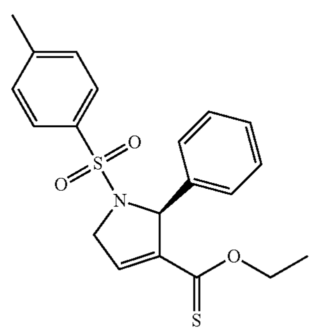

33% yield

To a solution of ethyl (S)-2-phenyl-1-tosyl-2,5-dihydro-1H-pyrrole-3-carboxylate (50 mg, 0.137 mmol) in PhCl (2 mL) was added Lawesson's reagent (220 mg, 0.543 mmol). The reaction mixture was then heated at 145° C. for 24 h. The solution was directly loaded on silica gel column and purified by hexane/EA (10/1 to 5/1) to give a yellow residue. This yellow residue was further purified by PTLC (hexane/EA: 4/1) to afford the title compound as yellow solid (17.5 mg, 33% yield). $[\alpha]^{24.6}_{D}$+137.9 (c 1.0, DCM).

FS151

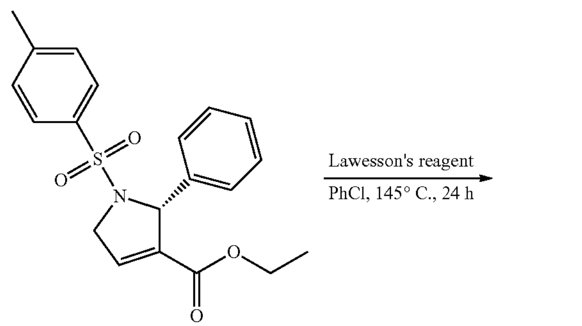

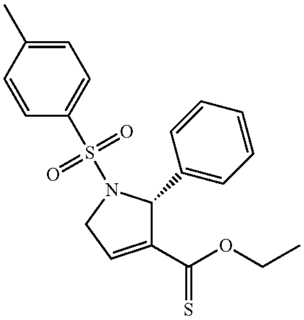

40% yield

To a solution of ethyl (R)-2-phenyl-1-tosyl-2,5-dihydro-1H-pyrrole-3-carboxylate (50 mg, 0.137 mmol) in PhCl (2 mL) was added Lawesson's reagent (220 mg, 0.543 mmol). The reaction mixture was then heated at 145° C. for 24 h. The solution was directly loaded on silica gel column and purified by hexane/EA (10/1 to 5/1) to give a yellow residue. This yellow residue was further purified by PTLC (hexane/EA: 4/1) to afford the title compound as yellow solid (17.5 mg, 33% yield). $[a]^{25.1}_{D}$-133.9 (c 1.0, DCM).

FS152

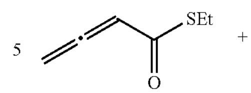

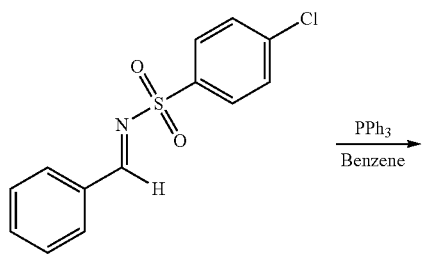

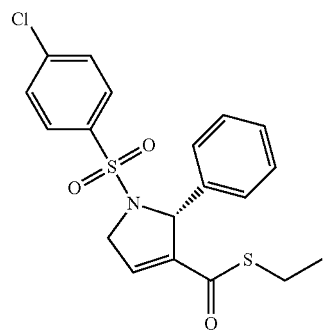

98% yield

To a solution of S-ethyl buta-2,3-dienethioate (51 mg, 0.39 mmol) and imine (100 mg, 0.35 mmol) in benzene (6 mL) was added $PPh_3$ (10 mg, 0.035 mmol) under ice bath. The reaction mixture was then warmed to room temperature and stirred overnight. This solution was concentrated and purified by FCC (Hexanes/EtOAc: 4/1) to give the title compound as white solid (143 mg, 98%). $^{1}$H NMR (500 MHz, $CDCl_3$) δ=7.45-7.40 (m, 2H), 7.39-7.32 (m, 4 H), 7.10-7.04 (m, 2H), 6.78 (q, J=2.0 Hz, 1H), 5.79 (td, J=1.8, 5.6 Hz, 1H), 4.55 (td, J=2.4, 17.1 Hz, 1H), 4.39 (ddd, J=2.0, 5.8, 17.1 Hz, 1H), 2.93-2.71 (m, 2H), 1.18 (t, J=7.4 Hz, 3H); $^{13}$C NMR (125 MHz, $CDCl_3$) δ=185.9, 142.1, 139.3, 137.6, 137.0, 132.9, 131.6, 129.5, 129.2, 128.3, 122.4, 68.4, 54.9, 23.2, 14.4.

FS153

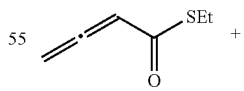

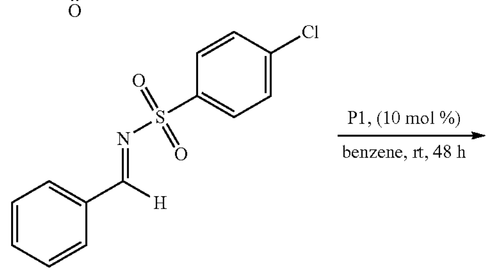

-continued

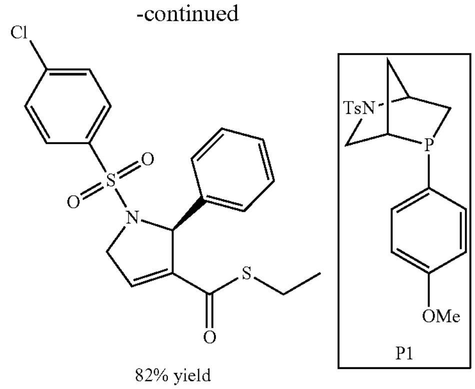

To a solution of S-ethyl buta-2,3-dienethioate (51 mg, 0.39 mmol) and imine (100 mg, 0.35 mmol) in benzene (6 mL) was added phosphine P1 (14 mg, 0.035 mmol) under ice bath. The reaction mixture was then warmed to room temperature and stirred for 48 h. This solution was concentrated and purified by FCC (Hexanes/EtOAc: 4/1) to give the title compound as white solid (110 mg, 82%). 96.7% ee, the ee value was determined by REGIS (R, R)-DACH, DNB column, hexane:DCM=65:35, 2 mL/min, 254 nm, $t_R$ (minor)=21.16 min, $t_R$ (major)=25.73 min.

FS154

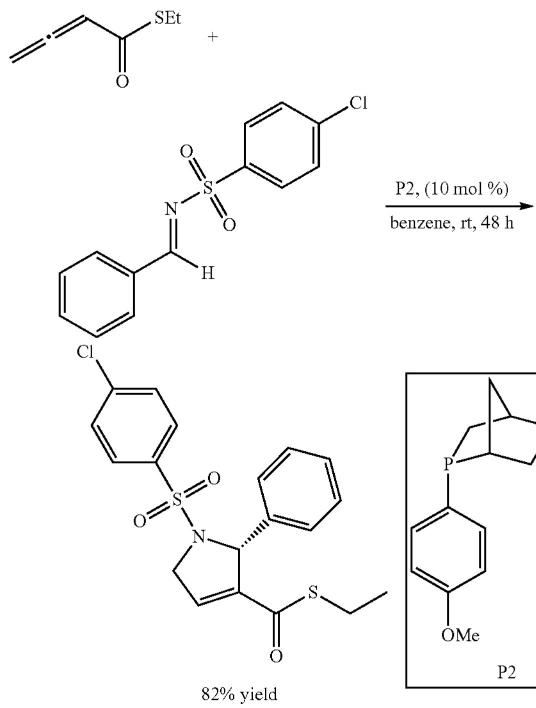

To a solution of S-ethyl buta-2,3-dienethioate (51 mg, 0.39 mmol) and imine (100 mg, 0.35 mmol) in benzene (6 mL) was added phosphine P1 (14 mg, 0.035 mmol) under ice bath. The reaction mixture was then warmed to room temperature and stirred for 48 h. This solution was concentrated and purified by FCC (Hexanes/EtOAc: 4/1) to give the title compound as white solid (98 mg, 80%). 99.9% ee, the ee value was determined by REGIS (R, R)-DACH, DNB column, hexane:DCM=60:40, 2 mL/min, 254 nm, $t_R$ (major)=3.18 min, $t_R$ (minor)=4.16 min.

FS155

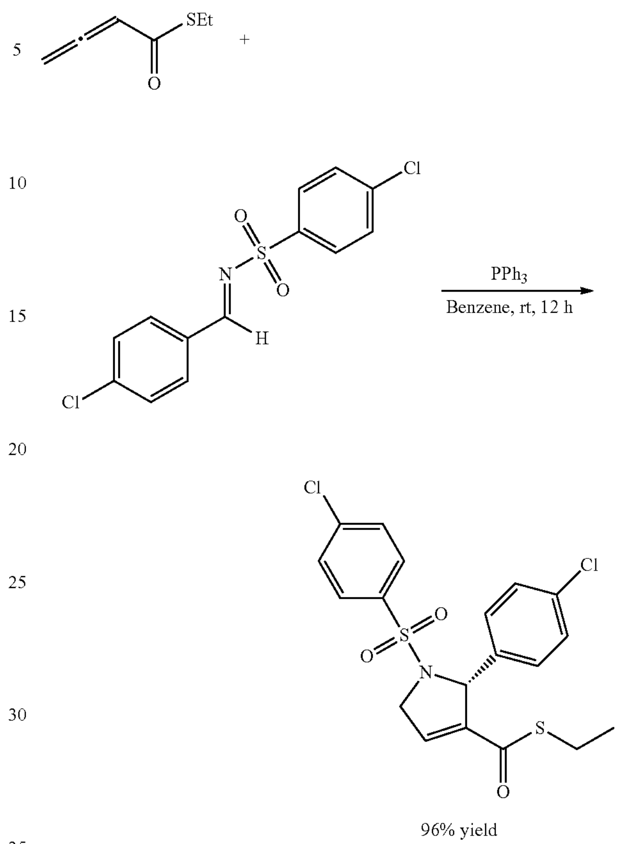

To a solution of S-ethyl buta-2,3-dienethioate (45 mg, 0.35 mmol) and imine (100 mg, 0.32 mmol) in benzene (6 mL) was added $PPh_3$ (10 mg, 0.032 mmol) under ice bath. The reaction mixture was then warmed to room temperature and stirred overnight. This solution was concentrated and purified by FCC (Hexanes/EtOAc: 4/1) to give the title compound as white solid (141 mg, 96%). $^1$H NMR (500 MHz, $CDCl_3$) δ=7.46-7.40 (m, 2H), 7.36-7.31 (m, 2H), 7.24-7.19 (m, 2H), 7.16-7.09 (m, 2H), 6.78 (q, J=2.2 Hz, 1H), 5.83-5.76 (m, 1H), 4.60-4.50 (m, 1H), 4.44-4.33 (m, 1H), 2.92-2.70 (m, 2H), 1.22-1.10 (m, 3H); $^{13}$C NMR (125 MHz, $CDCl_3$) δ=185.9, 142.1, 139.2, 137.1, 137.0, 134.2, 132.9, 129.2, 129.2, 128.6, 128.3, 68.4, 54.9, 23.2, 14.4.

FS156

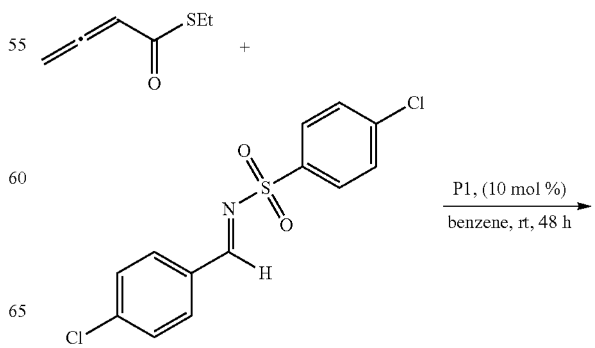

-continued

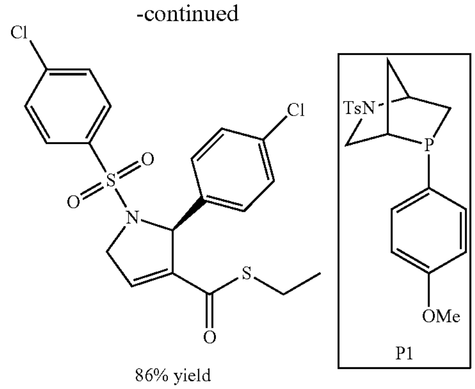

To a solution of S-ethyl buta-2,3-dienethioate (51 mg, 0.35 mmol) and imine (100 mg, 0.32 mmol) in benzene (6 mL) was added phosphine P1 (12 mg, 0.032 mmol) under ice bath. The reaction mixture was then warmed to room temperature and stirred for 48 h. This solution was concentrated and purified by FCC (Hexanes/EtOAc: 4/1) to give the title compound as white solid (119 mg, 86%). 95.7% ee, the ee value was determined by REGIS (R, R)-DACH, DNB column, hexane:DCM=65:35, 2 mL/min, 254 nm, $t_R$ (minor)=20.20 min, $t_R$ (major)=23.08 min.

FS157

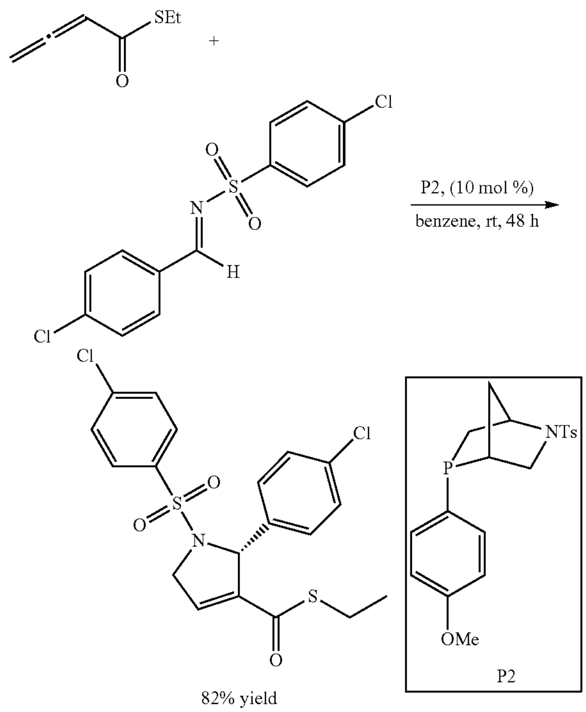

To a solution of S-ethyl buta-2,3-dienethioate (45 mg, 0.33 mmol) and imine (100 mg, 0.32mmol) in benzene (6 mL) was added phosphine P3 (12 mg, 0.032 mmol) under ice bath. The reaction mixture was then warmed to room temperature and stirred for 48 h. This solution was concentrated and purified by FCC (Hexanes/EtOAc: 4/1) to give the title compound as white solid (100 mg, 82%). 96.7% ee, the ee value was determined by REGIS (R, R)-DACH, DNB column, hexane:DCM=65:35, 2 mL/min, 254 nm, $t_R$ (major)=26.04 min, $t_R$ (minor)=21.37 min.

FS158

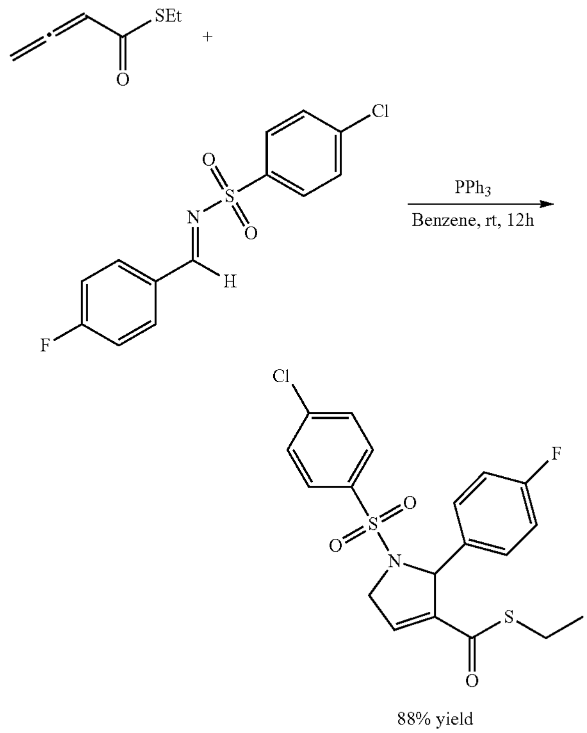

To a solution of S-ethyl buta-2,3-dienethioate (46 mg, 0.36 mmol) and imine (100 mg, 0.33 mmol) in benzene (6 mL) was added $PPh_3$ (10 mg, 0.033 mmol) under ice bath. The reaction mixture was then warmed to room temperature and stirred overnight. This solution was concentrated and purified by FCC (Hexanes/EtOAc: 4/1) to give the title compound as white solid (121 mg, 88%). $^1H$ NMR (500 MHz, $CDCl_3$) δ=7.46-7.37 (m, 2H), 7.35-7.29 (m, 2H), 7.21-7.10 (m, 2H), 6.93 (t, J=8.6 Hz, 2H), 6.78 (q, J=2.0 Hz, 1H), 5.83 (d, J=5.6 Hz, 1H), 4.55 (td, J=2.2, 17.1 Hz, 1H), 4.38 (ddd, J=2.1, 5.8, 17.2 Hz, 1H), 2.92-2.70 (m, 2H), 1.17 (t, J=7.4 Hz, 3H); $^{13}C$ NMR (125 MHz, $CDCl_3$) δ=185.9, 163.5, 161.6, 142.2, 139.1, 137.1, 134.4, 134.4, 132.8, 129.6, 129.5, 129.1, 128.3, 115.4, 115.3, 68.3, 54.7, 23.2, 14.3

FS159

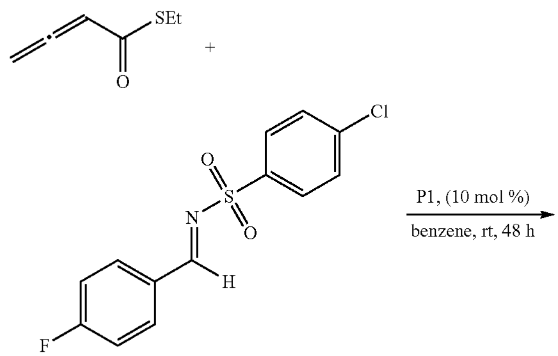

-continued

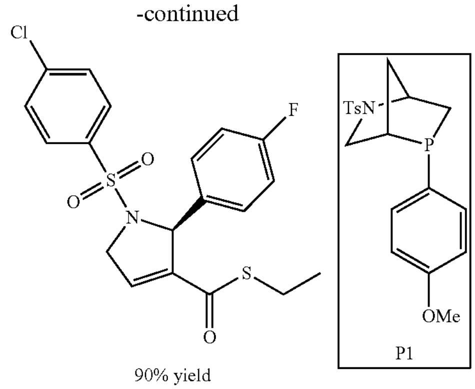

To a solution of S-ethyl buta-2,3-dienethioate (51 mg, 0.36 mmol) and imine (100 mg, 0.33 mmol) in benzene (6 mL) was added phosphine P1 (12 mg, 0.033 mmol) under ice bath. The reaction mixture was then warmed to room temperature and stirred for 48 h. This solution was concentrated and purified by FCC (Hexanes/EtOAc: 4/1) to give the title compound as white solid (125 mg, 90%). 98.1% ee, the ee value was determined by REGIS (R, R)-DACH, DNB column, hexane:DCM=65:35, 2 mL/min, 254 nm, $t_R$ (minor)=20.57 min, $t_R$ (major)=22.78 min.

FS160

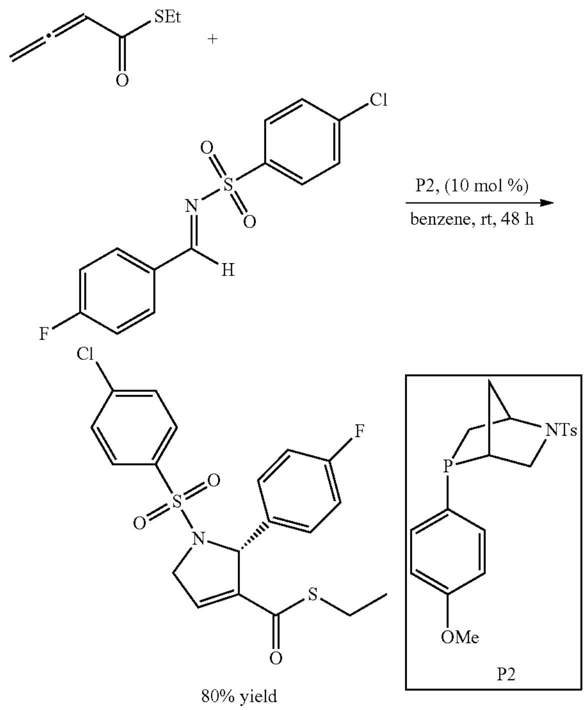

To a solution of S-ethyl buta-2,3-dienethioate (45 mg, 0.33 mmol) and imine (100 mg, 0.32 mmol) in benzene (6 mL) was added phosphine P1 (12 mg, 0.032 mmol) under ice bath. The reaction mixture was then warmed to room temperature and stirred for 48 h. This solution was concentrated and purified by FCC (Hexanes/EtOAc: 4/1) to give the title compound as white solid (101 mg, 80%). 99.9% ee, the ee value was determined by REGIS (R, R)-DACH, DNB column, hexane:DCM=65:35, 2 mL/min, 254 nm, $t_R$ (major)=16.27 min, $t_R$ (minor)=20.85 min.

FS161

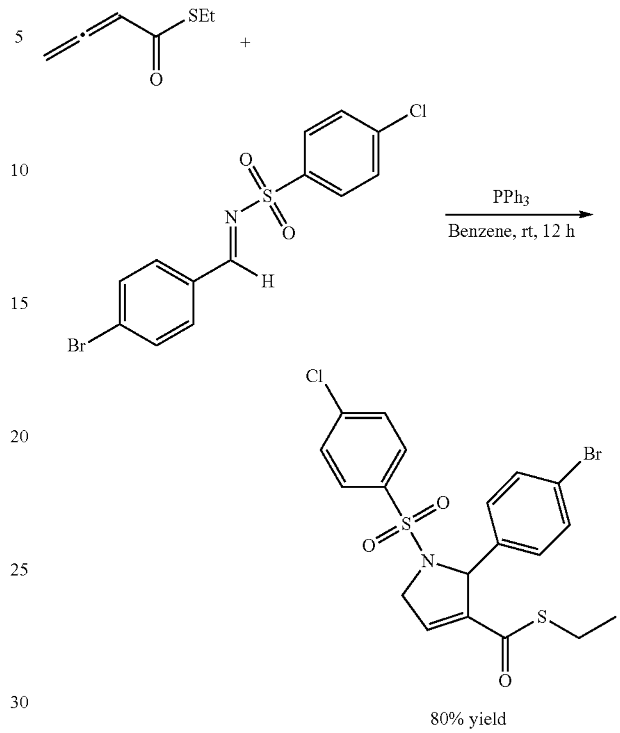

To a solution of S-ethyl buta-2,3-dienethioate (40 mg, 0.30 mmol) and imine (100 mg, 0.28 mmol) in benzene (6 mL) was added $PPh_3$ (9 mg, 0.028 mmol) under ice bath. The reaction mixture was then warmed to room temperature and stirred overnight. This solution was concentrated and purified by FCC (Hexanes/EtOAc: 4/1) to give the title compound as white solid (120 mg, 86%). $^1H$ NMR (500 MHz, $CDCl_3$) δ=7.39-7.34 (m, 2H), 7.30-7.25 (m, 4 H), 7.25-7.23 (m, 1H), 7.21-7.17 (m, 2H), 6.81 (q, J=1.9 Hz, 1H), 5.88 (td, J=1.8, 3.8 Hz, 1H), 4.61 (td, J=1.9, 17.1 Hz, 1H), 4.39 (ddd, J=2.0, 5.9, 17.0 Hz, 1H), 2.93-2.75 (m, 2H), 1.21-1.15 (m, 3H); $^{13}C$ NMR (125 MHz, $CDCl_3$) δ=185.9, 142.5, 138.9, 138.2, 137.4, 132.6, 129.0, 128.5, 128.3, 128.3, 127.9, 69.0, 54.7, 23.2, 14.4.

FS162

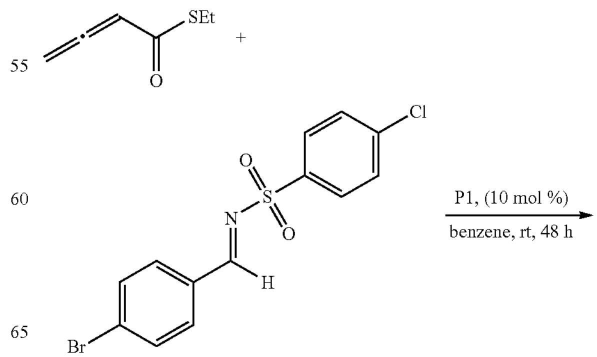

-continued

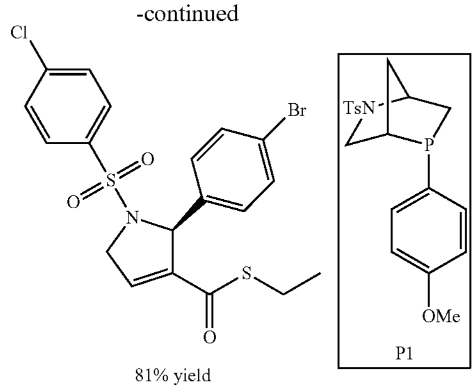

To a solution of S-ethyl buta-2,3-dienethioate (40 mg, 0.30 mmol) and imine (100 mg, 0.28 mmol) in benzene (6 mL) was added phosphine P1 (11 mg, 0.028 mmol) under ice bath. The reaction mixture was then warmed to room temperature and stirred for 48 h. This solution was concentrated and purified by FCC (Hexanes/EtOAc: 4/1) to give the title compound as white solid (98 mg, 81%). 96.7% ee, the ee value was determined by REGIS (R, R)-DACH, DNB column, hexane:DCM=65:35, 2 mL/min, 254 nm, $t_R$ (minor)=21.42 min, $t_R$ (major)=24.93 min.

FS 163

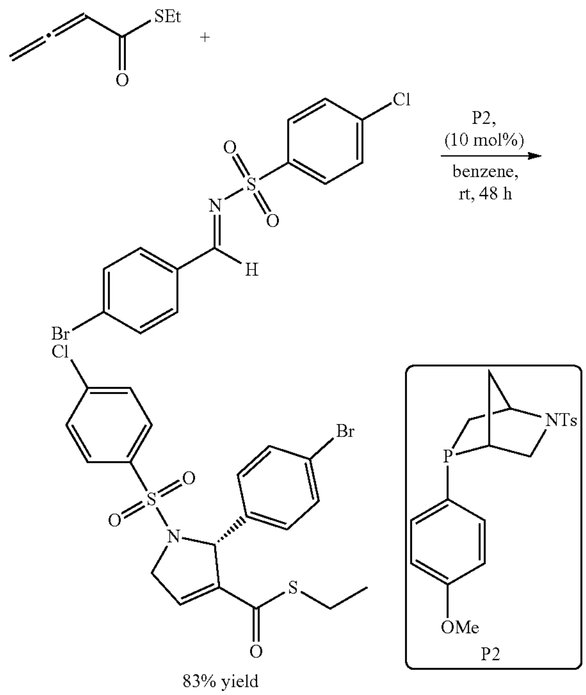

To a solution of S-ethyl buta-2,3-dienethioate (40 mg, 0.30 mmol) and imine (100 mg, 0.28 mmol) in benzene (6 mL) was added phosphine P1 (11 mg, 0.028 mmol) under ice bath. The reaction mixture was then warmed to room temperature and stirred for 48 h. This solution was concentrated and purified by FCC (Hexanes/EtOAc: 4/1) to give the title compound as white solid (103 mg, 83%). 98.3% ee, the ee value was determined by REGIS (R, R)-DACH, DNB column, hexane:DCM=65:35, 2 mL/min, 254 nm, $t_R$ (major)=22.13 min, $t_R$ (minor)=27.75 min.

FS 164

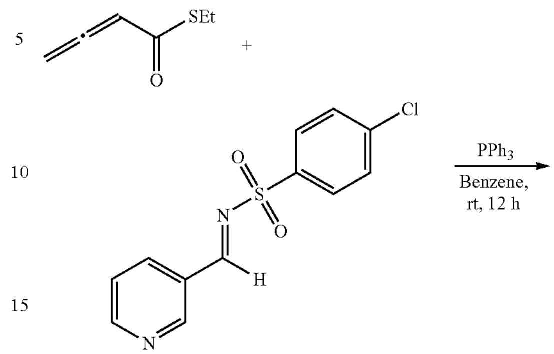

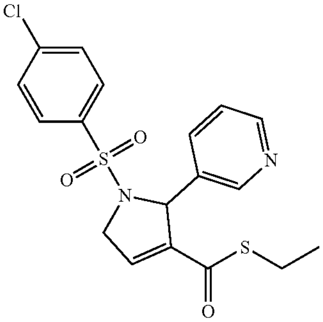

53% yield

To a solution of S-ethyl buta-2,3-dienethioate (137 mg, 1.07 mmol) and imine (200 mg, 0.71 mmol) in benzene (6 mL) was added $PPh_3$ (22 mg, 0.071 mmol) under ice bath. The reaction mixture was then warmed to room temperature and stirred overnight. This solution was concentrated and purified by FCC (Hexanes/EtOAc: 1/1) to give the title compound as white solid (157 mg, 53%). $^1$H NMR (500 MHz, $CDCl_3$) δ=8.56-8.42 (m, 2H), 7.55 (td, J=2.0, 7.9 Hz, 1H), 7.51-7.45 (m, 2H), 7.40-7.31 (m, 2H), 7.21 (ddd, J=0.8, 4.8, 7.9 Hz, 1 H), 6.85-6.75 (m, 1H), 5.84 (td, J=2.0, 5.6 Hz, 1H), 4.57 (td, J=2.4, 17.2 Hz, 1H), 4.45 (ddd, J=2.1, 5.8, 17.2 Hz, 1H), 2.93-2.71 (m, 2H), 1.17 (t, J=7.4 Hz, 3H); $^{13}$C NMR (125 MHz, $CDCl_3$) δ=185.8, 149.3, 149.1, 141.7, 139.5, 136.7, 135.5, 134.6, 133.4, 129.4, 128.4, 123.4, 66.9, 55.0, 23.3, 14.3.

FS165

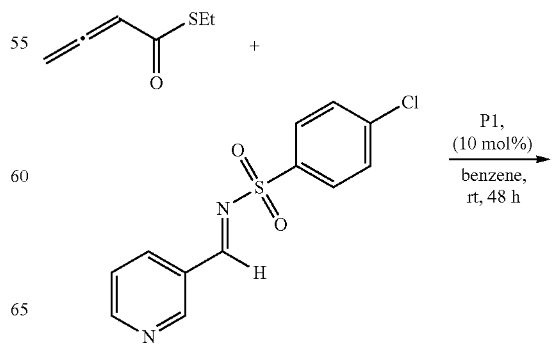

-continued

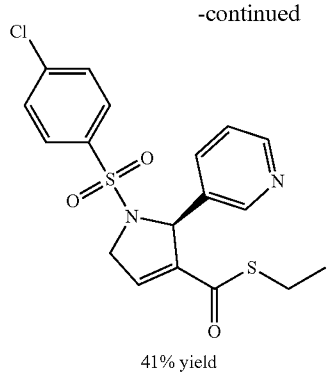

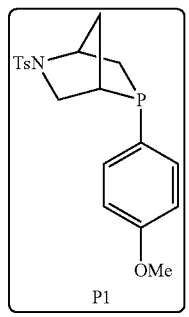

To a solution of S-ethyl buta-2,3-dienethioate (137 mg, 1.07 mmol) and imine (200 mg, 0.71 mmol) in benzene (6 mL) was added phosphine P1 (26 mg, 0.071 mmol) under ice bath. The reaction mixture was then warmed to room temperature and stirred for 48 h. This solution was concentrated and purified by FCC (Hexanes/EtOAc: 1/1) to give the title compound as white solid (122 mg, 41%). 93.9% ee, the ee value was determined by CHIRALPAK® AD-H column, hexane:IPA=80:20, 1 mL/min, 254 nm, $t_R$ (minor)=32.45 min, $t_R$ (major)=24.01 min.

FS166

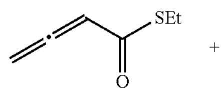

+

P2,
(10 mol%)
benzene,
rt, 48 h

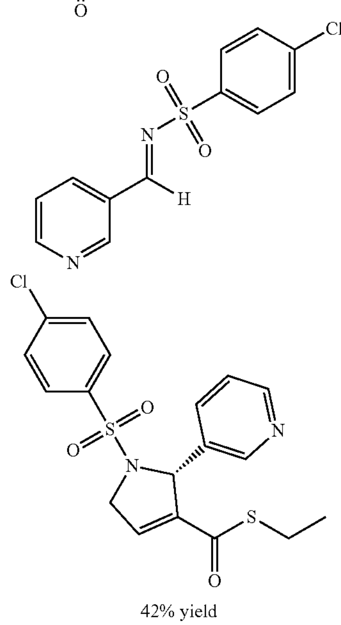

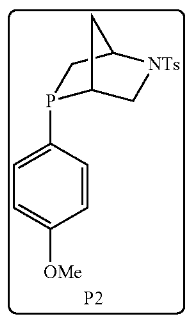

To a solution of S-ethyl buta-2,3-dienethioate (137 mg, 1.07 mmol) and imine (200 mg, 0.71 mmol) in benzene (6 mL) was added phosphine P1 (26 mg, 0.071 mmol) under ice bath. The reaction mixture was then warmed to room temperature and stirred for 48 h. This solution was concentrated and purified by FCC (Hexanes/EtOAc: 1/1) to give the title compound as white solid (125 mg, 42%). 95.4% ee, the ee value was determined by CHIRALPAK® AD-H column, hexane:IPA=80:20, 1 mL/min, 254 nm, $t_R$ (major)=31.21 min, $t_R$ (minor)=25.53 min.

FS167

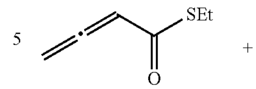

+

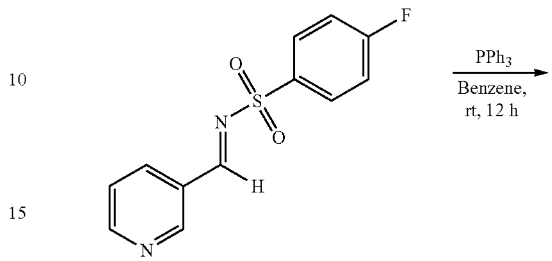

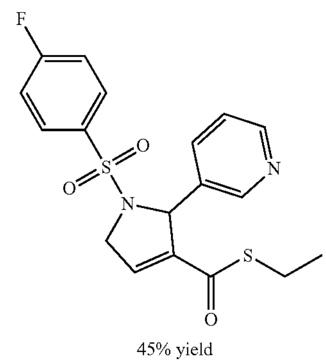

To a solution of S-ethyl buta-2,3-dienethioate (145 mg, 1.13 mmol) and imine (200 mg, 0.75 mmol) in benzene (6 mL) was added $PPh_3$ (20 mg, 0.075 mmol) under ice bath. The reaction mixture was then warmed to room temperature and stirred overnight. This solution was concentrated and purified by FCC (Hexanes/EtOAc: 1/1) to give the title compound as white solid (132 mg, 45%). $^1H$ NMR (500 MHz, $CDCl_3$) δ=8.54-8.34 (m, 2H), 7.66-7.50 (m, 3H), 7.25-7.17 (m, 1H), 7.12-7.02 (m, 2H), 6.85-6.77 (m, 1H), 5.83 (td, J=1.9, 5.6 Hz, 1H), 4.56 (td, J=2.5, 17.3 Hz, 1H), 4.45 (ddd, J=2.1, 5.7, 17.3 Hz, 1H), 2.90-2.70 (m, 2H), 1.16 (t, J=7.5 Hz, 3H); $^{13}C$ NMR (125 MHz, $CDCl_3$) δ=185.8, 166.1, 164.1, 148.9, 148.7, 141.6, 135.7, 134.8, 134.2, 134.2, 133.5, 129.7, 129.6, 123.5, 116.4, 116.3, 66.8, 55.0, 23.2, 14.3

FS 168

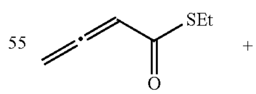

+

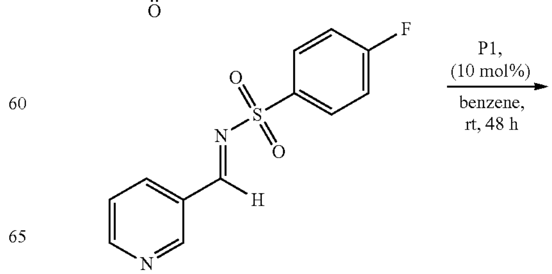

-continued

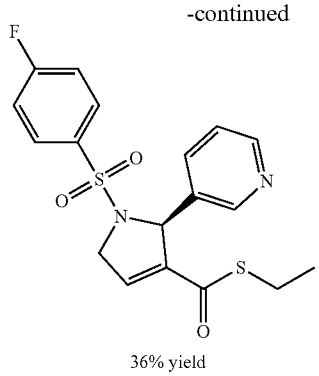

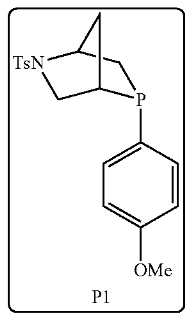

To a solution of S-ethyl buta-2,3-dienethioate (145 mg, 1.13 mmol) and imine (200 mg, 0.75 mmol) in benzene (6 mL) was added phosphine P1 (28 mg, 0.075 mmol) under ice bath. The reaction mixture was then warmed to room temperature and stirred for 48 h. This solution was concentrated and purified by FCC (Hexanes/EtOAc: 1/1) to give the title compound as white solid (102 mg, 36%). 94.4% ee, the ee value was determined by CHIRALPAK® AD-H column, hexane:IPA=90:10, 1 mL/min, 254 nm, $t_R$ (minor)=39.50 min, $t_R$ (major)=31.50 min.

FS 169

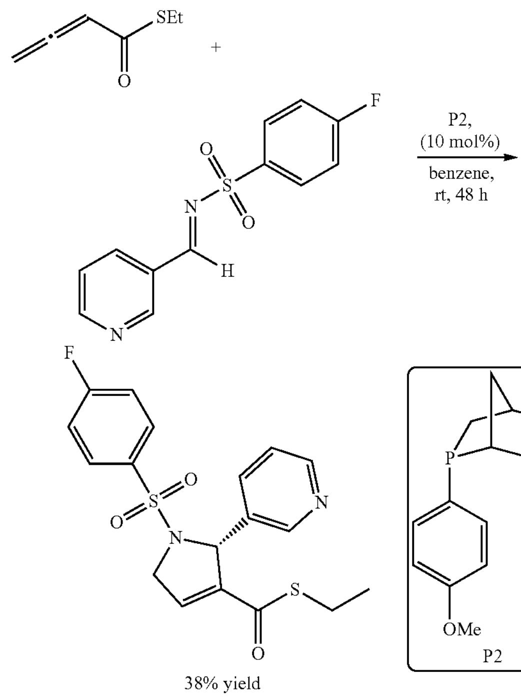

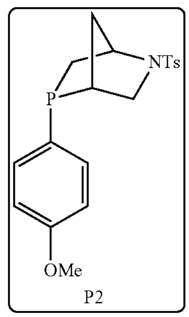

To a solution of S-ethyl buta-2,3-dienethioate (145 mg, 1.13 mmol) and imine (200 mg, 0.75 mmol) in benzene (6 mL) was added phosphine P1 (28 mg, 0.075 mmol) under ice bath. The reaction mixture was then warmed to room temperature and stirred for 48 h. This solution was concentrated and purified by FCC (Hexanes/EtOAc: 1/1) to give the title compound as white solid (106 mg, 38%). 94.9% ee, the ee value was determined by CHIRALPAK® AD-H column, hexane:IPA=90:10, 1 mL/min, 254 nm, $t_R$ (major)=38.12 min, $t_R$ (minor)=34.86 min.

FS 170

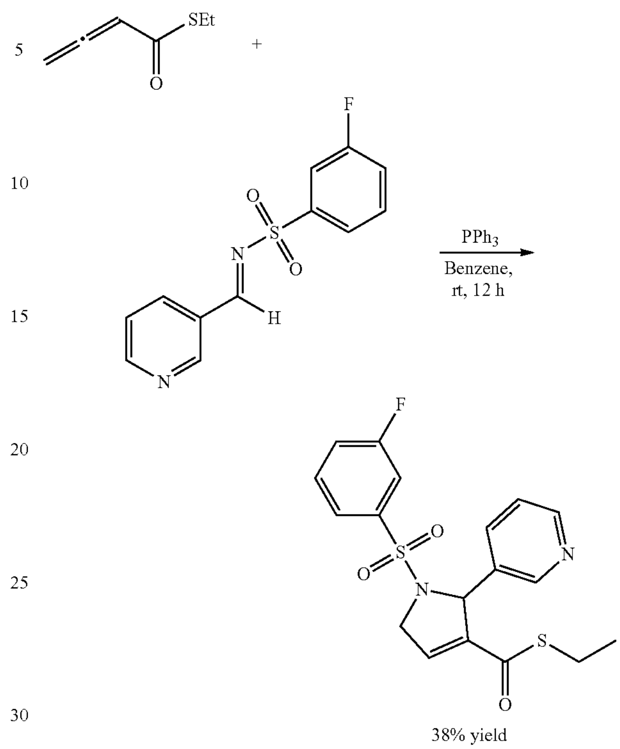

To a solution of S-ethyl buta-2,3-dienethioate (145 mg, 1.13 mmol) and imine (200 mg, 0.75 mmol) in benzene (6 mL) was added $PPh_3$ (20 mg, 0.075 mmol) under ice bath. The reaction mixture was then warmed to room temperature and stirred overnight. This solution was concentrated and purified by FCC (Hexanes/EtOAc: 1/1) to give the title compound as white solid (108 mg, 38%). $^1H$ NMR (500 MHz, $CDCl_3$) δ=8.49 (br. s., 1H), 8.44 (br. s., 1 H), 7.58-7.52 (m, 1H), 7.40-7.29 (m, 2H), 7.23-7.12 (m, 3H), 6.82 (q, J=2.1 Hz, 1H), 5.84 (td, J=1.9, 5.7 Hz, 1H), 4.59 (td, J=2.4, 17.1 Hz, 1H), 4.45 (ddd, J=2.0, 5.8, 17.2 Hz, 1H), 2.91-2.72 (m, 2H), 1.15 (t, J=7.4 Hz, 3H); $^{13}C$ NMR (125 MHz, $CDCl_3$) δ=185.7, 163.3, 161.3, 149.4, 149.0, 141.6, 140.3, 140.3, 135.5, 133.3, 130.9, 130.9, 122.6, 122.6, 120.2,

FS171

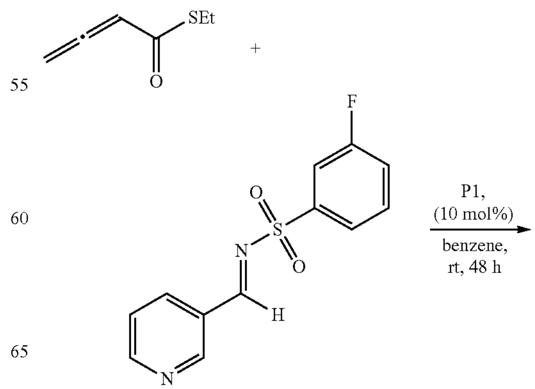

-continued

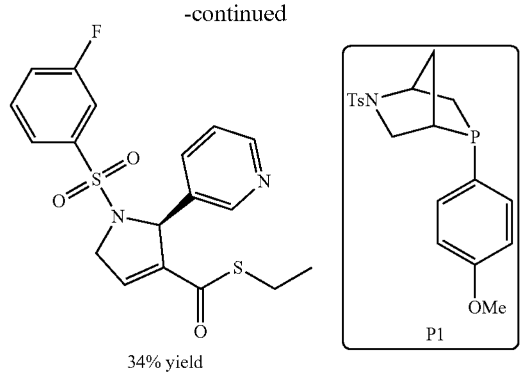

P1

34% yield

To a solution of S-ethyl buta-2,3-dienethioate (145 mg, 1.13 mmol) and imine (200 mg, 0.75 mmol) in benzene (6 mL) was added phosphine P1 (28 mg, 0.075 mmol) under ice bath. The reaction mixture was then warmed to room temperature and stirred for 48 h. This solution was concentrated and purified by FCC (Hexanes/EtOAc: 1/1) to give the title compound as white solid (100 mg, 34%). 94.5% ee, the ee value was determined by CHIRALPAK® AD-H column, hexane:IPA=90:10, 1 mL/min, 254 nm, $t_R$ (minor)=36.56 min, $t_R$ (major)=28.65 min.

FS172

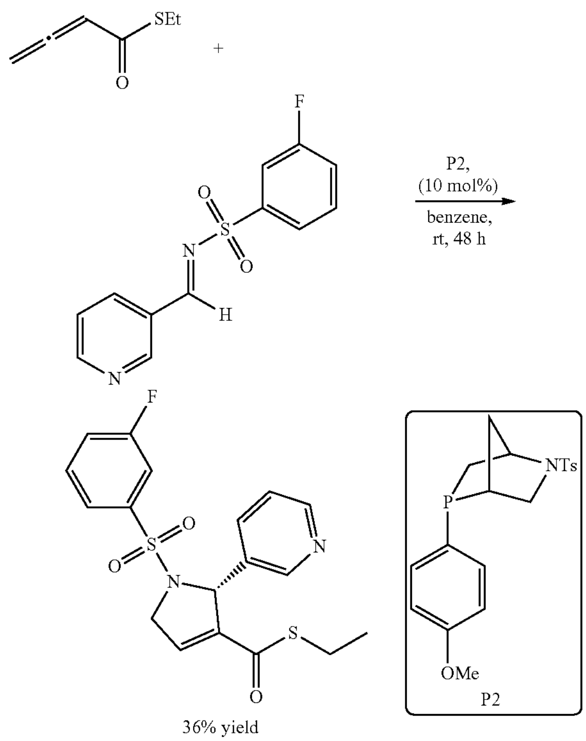

P2

36% yield

To a solution of S-ethyl buta-2,3-dienethioate (145 mg, 1.13 mmol) and imine (200 mg, 0.75 mmol) in benzene (6 mL) was added phosphine P1 (28 mg, 0.075 mmol) under ice bath. The reaction mixture was then warmed to room temperature and stirred for 48 h. This solution was concentrated and purified by FCC (Hexanes/EtOAc: 1/1) to give the title compound as white solid (105 mg, 36%). 92.8% ee, the ee value was determined by CHIRALPAK® AD-H coulmn, hexane:IPA=90:10, 1 mL/min, 254 nm, $t_R$ (major)=36.10 min, $t_R$ (minor)=32.22 min.

Preparation of S-ethyl buta-2, 3-dienethioate

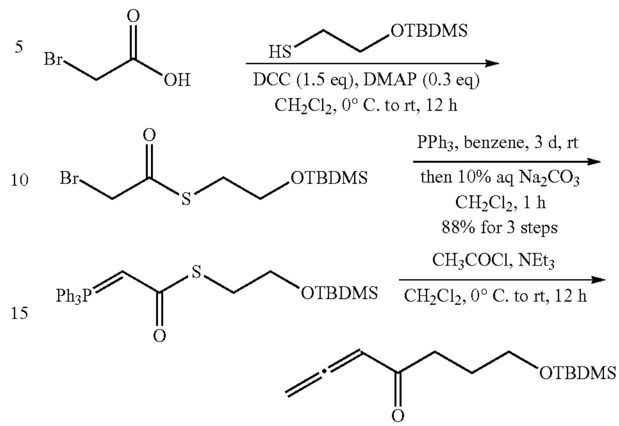

To a stirred solution of 2-bromoacetic acid (20.0 g, 144.9 mmol), 2-((tert-butyldimethylsilyl)oxy)ethane-1-thiol (36.17 gm, 188.4 mmol) and 4-dimethylaminepyridine (DMAP, 1.75 g, 14.4 mmol) in DCM (500 mL) was added DCC (N,N'-dicyclohexylcarbodiimide, 31.34 g, 152.1 mmol) under ice bath. The reaction mixture was slowly warmed to room temperature and stirred overnight. The solution was filtered through Celite, and washed several times with DCM. The filtrate was concentrated, dissolved in hexane (100 mL), filtered through Celite, and washed with hexane. The filtrate was concentrated to give a light-yellow oil. This crude oil was used in the next step without further purification.

The crude oil above and $PPh_3$ (41.92 g, 159.41 mmol) were dissolved in benzene (250 mL) and allowed to stand at room temperature for three days. The white crystals formed in the reaction flask was filtered and washed with benzene to yield the phosphonium salts. This phosphonium salts was dissolved in DCM (300 mL) and stirred with a solution of $Na_2CO_3$ solution (10% w/w, 200 mL) for 1 hour. The aqueous solution was exacted with DCM, washed with brine, dried over $Na_2SO_4$, and concentrated to give a crude solid. This crude solid was triturated with DCM/Hexane (1:20) to give S-(2-((tert-butyldimethylsilyl)oxy)ethyl) 2-(triphenyl-$\lambda^5$-phosphaneylidene)ethanethioate as white solid (72 g, 88% yield for 3 steps). $^1$H NMR (500 MHz, $CDCl_3$) δ=7.66-7.60 (m, 6 H), 7.59-7.54 (m, 3H), 7.50-7.45 (m, 6 H), 3.72 (t, J=6.9 Hz, 2H), 3.00 (t, J=6.9 Hz, 2H), 0.89 (s, 9 H), 0.06 (s, 6 H); $^{13}$C NMR (125 MHz, $CDCl_3$) δ=179.9, 179.9, 133.3, 133.2, 132.5, 132.5, 129.2, 129.1, 127.3, 126.6, 64.1, 47.5, 46.7, 31.6, 31.6, 26.2, 18.6, −4.9; $^{31}$P NMR (121 MHz, $CDCl_3$) δ=13.47

To s solution of S-(2-((tert-butyldimethylsilyl)oxy)ethyl) 2-(triphenyl-$\lambda^5$-phosphaneylidene) ethanethioate (20.0 g, 40.5 mmol) and triethylamine (6.19 ml, 44.5 mmol) in DCM (180 mL) was added a solution of acetyl chloride (3.0 ml, 44.5 mmol) in DCM (100 mL) dropwise (about 1 mL/min) under ice bath. This reaction mixture was stirred overnight, and pentane (200 mL) was added. The resulting mixture was filtered through Celite and concentrated under vacuum and low temperature (the temperature of bath was below 10° C.). The crude product was purified by FCC (pentane/$Et_2O$: 10/1) to the title compound S-(2-((tert-butyldimethylsilyl) oxy)ethyl) buta-2,3-dienethioate as yellow oil (4.8 g, 62%). $^1$H NMR (500 MHz, $CDCl_3$) δ=5.97-5.88 (m, 1H), 5.34 (dd, J=0.9, 6.4 Hz, 2H), 3.74-3.70 (m, 2 H), 3.09-3.04 (m, 2H), 0.90-0.89 (S, 9 H), 0.07 (d, J=0.9 Hz, 6 H); $^{13}C$ NMR (125 MHz, $CDCl_3$) δ=214.3, 189.1, 95.9, 81.5, 62.0, 31.5, 25.8, 25.8, 18.3, −5.3, −5.4.

FS173

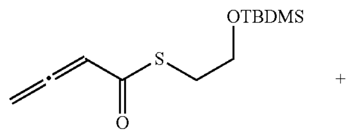

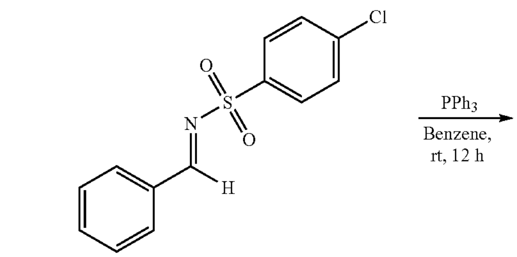

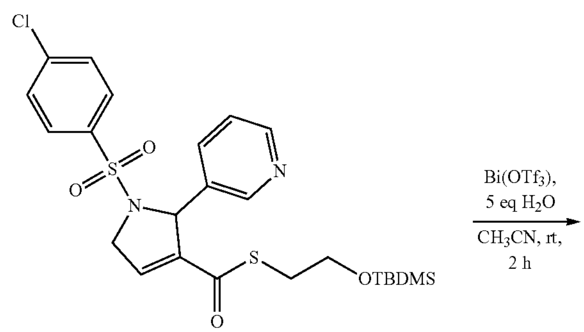

-continued

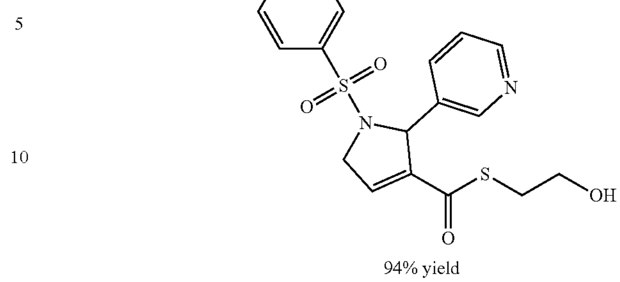

To a solution of S-(2-((tert-butyldimethylsilyl)oxy)ethyl) buta-2,3-dienethioate (203 mg, 0.78 mmol) and imine (200 mg, 0.71 mmol) in benzene (6 mL) was added $PPh_3$ (20 mg, 0.075 mmol) under ice bath. The reaction mixture was then warmed to room temperature and stirred overnight. This solution was concentrated and purified by FCC (Hexanes/EtOAc: 4/1) to give the title compound as white solid (310 mg, 80%). $^1H$ NMR (500 MHz, $CDCl_3$) δ=7.39-7.32 (m, 2H), 7.31-7.19 (m, 6 H), 7.19-7.10 (m, 2H), 6.86-6.77 (m, 1H), 5.89-5.83 (m, 1H), 4.60 (td, J=2.3, 17.0 Hz, 1H), 4.44-4.29 (m, 1H), 3.62 (t, J=6.2 Hz, 2H), 3.10-2.88 (m, 2H), 0.90-0.78 (m, 9 H), −0.02 (s, 6 H); $^{13}C$ NMR (125 MHz, $CDCl_3$) δ=185.7, 142.4, 138.9, 138.2, 137.4, 132.9, 129.0, 128.5, 128.4, 128.3, 127.9, 69.0, 61.6, 54.8, 31.7, 25.8, 18.2, −5.4

To a solution of OTBDMS-Efesvin (300 mg, 0.52 mmol) in $CH_3CN$ (8 mL) were successively added distilled $H_2O$ (45 μL, 5 equiv) and $Bi(OTf)_3$ (6.8 mg, 2 mol %). After stirring the reaction mixture for 2 h and then reaction mixture concentrated in vacuo. The crude product was purified by FCC (Hexanes/EtOAc: 1/1) to give the title compound as white solid (220 mg, 94%); $^1H$ NMR (500 MHz, $CDCl_3$) δ=7.38-7.30 (m, 2H), 7.28-7.20 (m, 5 H), 7.19-7.11 (m, 2H), 6.86 (d, J=1.5 Hz, 1H), 5.86 (d, J=5.8 Hz, 1H), 4.61 (td, J=2.3, 17.1 Hz, 1H), 4.38 (ddd, J=1.8, 5.8, 17.1 Hz, 1H), 3.66 (t, J=6.0 Hz, 2H), 3.15-2.93 (m, 2H); $^{13}C$ NMR (125 MHz, $CDCl_3$) δ=185.8, 142.2, 138.9, 138.1, 137.3, 133.6, 129.0, 128.5, 128.4, 128.2, 127.9, 69.0, 61.4, 54.8, 31.6

FS174

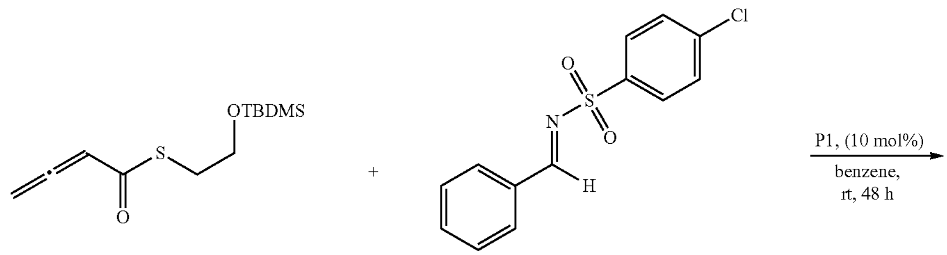

-continued

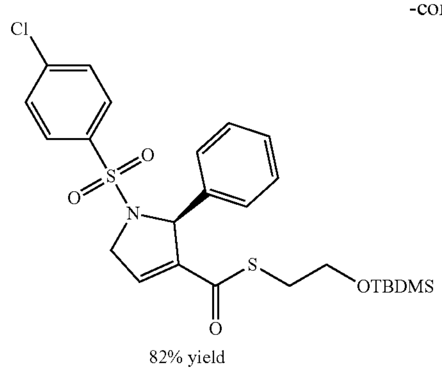

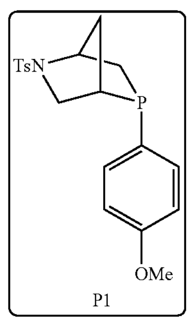

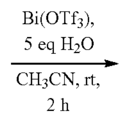

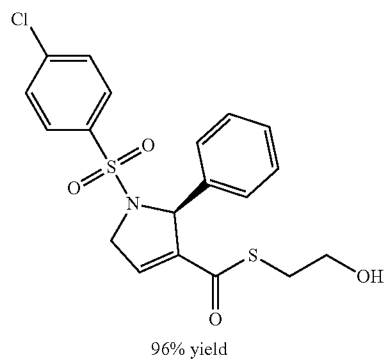

To a solution of S-(2-((tert-butyldimethylsilyl)oxy)ethyl) buta-2,3-dienethioate (203 mg, 0.78 mmol) and imine (200 mg, 0.71 mmol) in benzene (6 mL) was added $PPh_3$ (20 mg, 0.075 mmol) under ice bath. The reaction mixture was then warmed to room temperature and stirred overnight. This solution was concentrated and purified by FCC (Hexanes/EtOAc: 4/1) to give the title compound as white solid (320 mg, 82%). To a solution of OTBDMS-Efesvin (300 mg, 0.4 mmol) in $CH_3CN$ (2.5 mL) were successively added distilled $H_2O$ (45 μL, 5 equiv) and $Bi(OTf)_3$ (6.8 mg, 2 mol %). After stirring the reaction mixture for 2 h and then reaction mixture concentrated in vacuo. The crude product was purified by FCC (Hexanes/EtOAc: 1/1) to give the title compound as white solid (228 mg, 96%). 99.99% ee, the ee value was determined by REGIS (R, R)-DACH, DNB column, hexane:IPA=70:30, 1 mL/min, 254 nm, $t_R$ (major)=47.42 min.

FS175

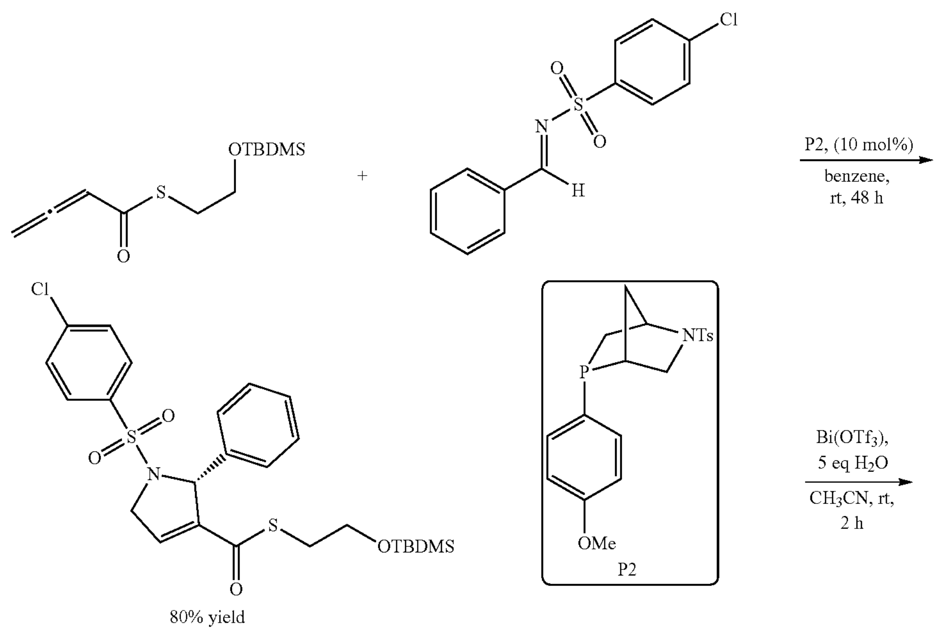

-continued

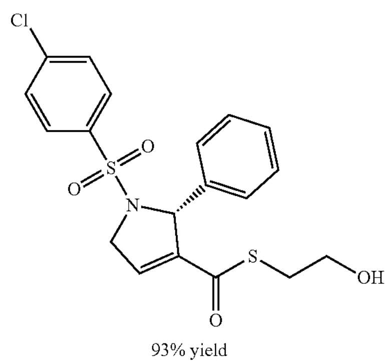

93% yield

To a solution of S-(2-((tert-butyldimethylsilyl)oxy)ethyl) buta-2,3-dienethioate (203 mg, 0.78 mmol) and imine (200 mg, 0.71 mmol) in benzene (6 mL) was added $PPh_3$ (20 mg, 0.075 mmol) under ice bath. The reaction mixture was then warmed to room temperature and stirred overnight. This solution was concentrated and purified by FCC (Hexanes/EtOAc: 4/1) to give the title compound as white solid (310 mg, 80%). To a solution of OTBDMS-Efesvin (300 mg, 0.4 mmol) in $CH_3CN$ (2.5 mL) were successively added distilled $H_2O$ (45 μL, 5 equiv) and $Bi(OTf)_3$ (6.8 mg, 2 mol %). After stirring the reaction mixture for 2 h and then reaction mixture concentrated in vacuo. The crude product was purified by FCC (Hexanes/EtOAc: 1/1) to give the title compound as white solid (205 mg, 93%). 98.04% ee, the ee value was determined by REGIS (R, R)-DACH, DNB column, hexane:IPA=70:30, 1 mL/min, 254 nm, $t_R$ (major)=42.42 min, $t_R$ (minor)=51.69 min.

Predicted and observed molecular mass values of certain compounds of the disclosure are listed in the table below.

| Compound Number | Predicted Mass ($[M + H]^+$) | Observed Mass ($[M + H]^+$) |
|---|---|---|
| FS001 | 372.1 | 372.1 |
| FS002 | 372.1 | 372.1 |
| FS003 | 372.1 | 372.1 |
| FS004 | 344.1 | 344.1 |
| FS005 | 344.1 | 344.1 |
| FS006 | 344.1 | 344.1 |
| FS007 | 330.1 | 330.1 |
| FS008 | — | — |
| FS009 | 399.2 | 399.2 |
| FS010 | 357.1 | 357.1 |
| FS011 | 371.1 | 371.1 |
| FS012 | 413.1 | 413.1 |
| FS013 | 343.1 | 343.1 |
| FS014 | 371.1 | 371.1 |
| FS015 | 387.1 | 387.1 |
| FS016 | 387.1 | 387.1 |
| FS017 | 406.0 | 406.0 |
| FS018 | 386.1 | 386.1 |
| FS019 | 440.0 | 440.0 |
| FS020 | 405.9 | 406.0 |
| FS021 | 450.1 | 450.1 |
| FS022 | 390.1 | 390.1 |
| FS023 | 460.0 | 460.0 |
| FS024 | 426.0 | 426.0 |
| FS025 | 386.1 | 386.1 |
| FS026 | 470.0 | 470.0 |
| FS027 | 410.1 | 410.1 |
| FS028 | 406.1 | 406.1 |
| FS029 | 505.9 | 505.9 |
| FS030 | 472.0 | 472.0 |
| FS031 | 515.9 | 515.9 |
| FS032 | 454.0 | 454.0 |

-continued

| Compound Number | Predicted Mass ($[M + H]^+$) | Observed Mass ($[M + H]^+$) |
|---|---|---|
| FS033 | 452.0 | 452.0 |
| FS034 | 444.0 | 444.0 |
| FS035 | 410.1 | 410.0 |
| FS036 | — | — |
| FS037 | — | — |
| FS038 | — | — |
| FS039 | 452.0 | 452.0 |
| FS040 | 390.1 | 390.1 |
| FS041 | 426.0 | 426.0 |
| FS042 | 472.0 | 472.0 |
| FS043 | 410.0 | 410.0 |
| FS044 | 406.1 | 406.1 |
| FS045 | 470.0 | 470.0 |
| FS046 | 516.0 | 515.9 |
| FS047 | — | — |
| FS048 | 450.0 | 450.0 |
| FS049 | — | — |
| FS050 | 454.0 | 454.0 |
| FS051 | — | — |
| FS052 | — | — |
| FS053 | 372.1 | 372.1 |
| FS054 | 392.1 | 392.1 |
| FS055 | — | — |
| FS056 | — | — |
| FS057 | 386.1 | 386.1 |
| FS058 | — | — |
| FS059 | 416.1 | 416.1 |
| FS060 | 397.1 | 397.1 |
| FS061 | 444.1 | 444.1 |
| FS062 | — | — |
| FS063 | 406.1 | 406.1 |
| FS064 | 406.1 | 406.0 |
| FS065 | 440.0 | 440.0 |
| FS066 | 450.0 | 450.0 |
| FS067 | 450.0 | 450.0 |
| FS068 | 422.1 | 422.1 |
| FS069 | 390.1 | 390.1 |
| FS070 | 414.2 | 414.2 |
| FS071 | 426.0 | 426.1 |
| FS072 | 392.1 | 392.0 |
| FS073 | 450.1 | 450.0 |
| FS074 | 386.1 | 386.1 |
| FS075 | 417.1 | 417.1 |
| FS076 | — | — |
| FS077 | 372.1 | 372.1 |
| FS078 | 400.1 | 400.1 |
| FS079 | 428.2 | 428.2 |
| FS080 | 414.1 | 414.1 |
| FS081 | 414.1 | 414.1 |
| FS082 | 428.2 | 428.2 |
| FS083 | — | — |
| FS084 | — | — |
| FS085 | — | — |
| FS086 | 406.1 | 406.1 |
| FS087 | 462.0 | 462.0 |
| FS088 | 426.0 | 426.0 |

-continued

| Compound Number | Predicted Mass ([M + H]$^+$) | Observed Mass ([M + H]$^+$) |
|---|---|---|
| FS089 | 472.0 | 472.0 |
| FS090 | 410.1 | 410.0 |
| FS091 | 406.1 | 406.1 |
| FS092 | 505.9 | 506.0 |
| FS093 | 472.0 | 472.0 |
| FS094 | 515.9 | 515.9 |
| FS095 | 454.0 | 454.0 |
| FS096 | 450.0 | 450.0 |
| FS097 | 472.0 | 472.0 |
| FS098 | 410.1 | 410.0 |
| FS099 | 472.0 | 472.0 |
| FS100 | 515.9 | 515.9 |
| FS101 | 454.0 | 454.0 |
| FS102 | 450.0 | 450.0 |
| FS103 | 392.1 | 392.1 |
| FS104 | 436.0 | 436.0 |
| FS105 | 414.1 | 414.1 |
| FS106 | 414.1 | 414.1 |
| FS107 | 414.1 | 414.1 |
| FS108 | 414.1 | 414.1 |
| FS109 | 490.2 | 490.2 |
| FS110 | 490.2 | 490.2 |
| FS111 | 490.2 | 490.2 |
| FS112 | 490.2 | 490.2 |
| FS113 | 444.0 | 444.0 |
| FS114 | 410.1 | 410.0 |
| FS115 | 454.0 | 454.0 |
| FS116 | 394.1 | 393.1 |
| FS117 | 390.1 | 390.1 |
| FS118 | 460.0 | 460.0 |
| FS119 | 426.0 | 426.0 |
| FS120 | 470.0 | 470.0 |
| FS121 | 410.0 | 410.0 |
| FS122 | 406.1 | 406.1 |
| FS123 | 410.1 | 410.0 |
| FS124 | 454.0 | 454.0 |
| FS125 | 394.1 | 394.1 |
| FS126 | 390.1 | 390.1 |
| FS127 | 426.0 | 426.0 |
| FS128 | 472.0 | 472.0 |
| FS129 | 410.1 | 410.0 |
| FS130 | 406.1 | 406.1 |
| FS131 | 376.1 | 376.1 |
| FS132 | — | — |
| FS133 | 410.1 | 410.0 |
| FS134 | 454.0 | 454.0 |
| FS135 | 394.1 | 394.0 |
| FS136 | 472.0 | 472.0 |
| FS137 | 515.9 | 515.9 |
| FS138 | 454.0 | 454.0 |
| FS139 | 330.0 | 330.0 |
| FS140 | 310.1 | 310.1 |
| FS141 | 417.1 | 417.1 |
| FS142 | 403.1 | 403.0 |
| FS143 | — | — |
| FS144 | 388.1 | 388.1 |
| FS145 | 388.1 | 388.1 |
| FS146 | 388.1 | 388.1 |
| FS147 | 378.1 | 378.1 |
| FS148 | 358.1 | 358.1 |
| FS149 | 388.1 | 388.1 |
| FS150 | 388.1 | 388.1 |
| FS151 | 388.1 | 388.1 |
| FS152 | — | — |
| FS153 | — | — |
| FS154 | — | — |
| FS155 | — | — |
| FS156 | — | — |
| FS157 | — | — |
| FS158 | — | — |
| FS159 | — | — |
| FS160 | — | — |
| FS161 | — | — |
| FS162 | — | — |
| FS163 | — | — |
| FS164 | — | — |
| FS165 | — | — |
| FS166 | — | — |
| FS167 | — | — |
| FS168 | — | — |
| FS169 | — | — |
| FS170 | — | — |
| FS171 | — | — |
| FS172 | — | — |
| FS173 | — | — |
| FS174 | — | — |
| FS175 | — | — |

Related compounds are disclosed in PCT/US2015/065876, the contents of which are hereby incorporated by reference in its entirety.

Example 2

In Vivo Activity of Exemplary Compounds of the Disclosure Zebrafish Husbandry And Transgenic Lines Zebrafish of the mutant line tremblor ($tre^{tc318}$) were maintained and bred as described previously in the literature. C. f. Langenbacher A D, et al., *PNAS,* 2005, 102(49), 17699-17704.

Compound Rescue Screen

Exemplary compounds were screened for their ability to partially or completely restore persistent heartbeat in $tre^{tc318}$ embryos. 10 $tre^{tc318}$ mutant embryos were placed in each well of a 24-well plate and raised in the presence of individual compounds at various concentrations (5, 10, 15 and 20 μM) from 30 hpf. Cardiac function was analyzed by visual inspection at 2 dpf. The hearts of $tre^{tc318}$ embryos manifest a chaotic movement resembling cardiac fibrillation with sporadic contractions. Compounds that elicited persistent coordinated cardiac contractions were validated by rescreening at least once on another 10 $tre^{tc318}$ mutant embryos.

| Compound No. | Rescue at 10 uM (%) | Rescue at 15 uM (%) | Rescue at 20 uM (%) |
|---|---|---|---|
| FS019 | 30 | 40 | 30 |
| FS020 | 0 | — | — |
| FS021 | 10 | — | — |
| FS022 | 0 | — | — |
| FS025 | 0 | — | — |
| FS017 | 25 | 60 | 20 |
| FS039 | 33 | — | — |
| FS040 | 0 | 33 | 22 |
| FS018 | 0 | — | — |
| FS053 | 0 | — | — |
| FS023 | 45 | 40 | 20 |
| FS024 | 0 | — | — |
| FS026 | 0 | — | — |
| FS027 | 0 | — | — |
| FS028 | 0 | — | — |
| FS041 | 44 | 30 | 20 |
| FS042 | 0 | — | — |
| FS043 | 33 | — | — |
| FS044 | 0 | — | — |
| FS054 | 0 | — | — |
| FS029 | 70 | 10 | 10 |
| FS030 | 0 | — | — |
| FS031 | 0 | — | — |
| FS032 | 0 | — | — |

-continued

| Compound No. | Rescue at 10 uM (%) | Rescue at 15 uM (%) | Rescue at 20 uM (%) |
|---|---|---|---|
| FS033 | 0 | — | — |
| FS045 | 33 | 30 | 0 |
| FS046 | 60 | 10 | 10 |
| FS047 | 20 | — | — |
| FS048 | 0 | — | — |
| FS055 | 0 | — | — |
| FS034 | 65 | 30 | 20 |
| FS035 | 0 | — | — |
| FS036 | 0 | — | — |
| FS037 | 0 | — | — |
| FS038 | 25 | — | — |
| FS049 | 25 | — | — |
| FS050 | 50 | 10 | 0 |
| FS051 | 10 | 22 | 11 |
| FS052 | 0 | 44 | 56 |
| FS056 | 20 | 0 | 0 |
| FS087 | 22 | 0 | 0 |
| FS088 | 0 | — | — |
| FS089 | 0 | — | — |
| FS090 | 40 | — | — |
| FS091 | 0 | — | — |
| FS085 | 89 | 80 | 80 |
| FS097 | 0 | 89 | 78 |
| FS098 | 40 | 44 | 89 |
| FS086 | 11 | — | — |
| FS103 | 20 | 80 | 40 |
| FS092 | 0 | 11 | 11 |
| FS093 | 0 | — | — |
| FS094 | 11 | 75 | 25 |
| FS095 | 40 | — | — |
| FS096 | 22 | — | — |
| FS099 | 0 | 33 | — |
| FS100 | 0 | 33 | — |
| FS101 | 20 | — | — |
| FS102 | 0 | — | — |
| FS104 | 60 | 50 | 60 |
| FS113 | — | 50 | — |
| FS114 | — | 22 | — |
| FS115 | — | 30 | — |
| FS116 | — | 11 | — |
| FS117 | — | 56 | — |
| FS123 | — | 70 | — |
| FS124 | — | 90 | — |
| FS125 | — | 80 | — |
| FS126 | — | 40 | — |
| FS131 | — | 20 | — |
| FS065 | 11 | — | — |
| FS064 | 20 | — | — |
| FS067 | 20 | — | — |
| FS071 | 0 | — | — |
| FS074 | 10 | 40 | 50 |
| FS063 | 40 | — | — |
| FS066 | 11 | — | — |
| FS069 | 60 | 70 | 44 |
| FS057 | 60 | 70 | 60 |
| FS001 | 58 | 80 | 45 |
| FS058 | 58 | 80 | 45 |
| FS059 | 20 | — | — |
| FS060 | 80 | 60 | 0 |
| FS061 | 40 | 56 | 40 |
| FS062 | 50 | 90 | 60 |
| FS068 | 0 | 0 | 0 |
| FS070 | 0 | — | — |
| FS147 | — | 60 | — |
| FS118 | — | 10 | — |
| FS119 | — | 50 | — |
| FS120 | — | 56 | — |
| FS121 | — | 56 | — |
| FS122 | — | 33 | — |
| FS127 | — | 44 | — |
| FS128 | — | 13 | — |
| FS129 | — | 56 | — |
| FS130 | — | 50 | — |
| FS132 | — | 88 | — |
| FS133 | — | 78 | — |

-continued

| Compound No. | Rescue at 10 uM (%) | Rescue at 15 uM (%) | Rescue at 20 uM (%) |
|---|---|---|---|
| FS134 | — | 60 | — |
| FS135 | — | 50 | — |
| FS136 | — | 29 | — |
| FS137 | — | 0 | — |
| FS138 | — | 50 | — |
| FS075 | 0 | — | — |
| FS139 | — | 0 | — |
| FS140 | — | 0 | — |
| FS072 | 60 | 70 | 40 |
| FS077 | 30 | — | — |
| FS148 | — | 56 | — |
| FS073 | 40 | — | — |
| FS076 | 40 | 60 | 10 |
| FS141 | — | 0 | — |
| FS142 | — | 56 | — |

Example 3

Pharmacokinetics of Exemplary Compounds of the Disclosure

Pooled human, rat and mouse liver microsomes used in this study were purchased from Corning (USA). The pooled liver microsomes were stored at −60° C. prior to use.

A stock solution of each compound was prepared at 10 mM in DMSO. The compound was then co-incubated with human, rat and mouse liver microsomes at 37° C. at a concentration of 1 μM. Reactions were then initiated by the addition of NADPH to a final concentration of 1 mM.

At each time point, small aliquots from the incubation system were transferred into ice-cold acetonitrile containing an internal standard to quench the reactions. After vortex and centrifuge at 3700 rpm for 30 min, the supernatants were injected into LC-MS/MS for analysis. In vitro microsomal clearance was estimated based on determination of elimination half life ($T_{1/2}$) of compounds disappearance from their initial concentrations.

| Compound No. | Mouse (%) | Rat (%) | Human (%) |
|---|---|---|---|
| R-efsevin | 0.14 | 0.16 | 0.06 |
| FS144 | 0.17 ± 0.1 | 0.20 ± 0.12 | 0.10 ± 0.07 |
| FS146 | 0.17 ± 0.17 | 3.17 ± 5.32 | 0.16 ± 0.02 |
| R-efsevin acid | 78.6 ± 6.64 | 75.1 ± 2.93 | 69.7 ± 6.37 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A compound represented by Formula I:

I

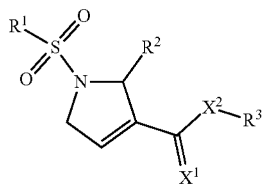

or a pharmaceutically acceptable salt thereof; wherein $X^1$ is O, S, or $NR^4$;

$X^2$ is S;

$R^1$ is alkyl, cycloalkyl, aryl, heteroaryl, or heterocyclyl;

$R^2$ is aryl or heteroaryl;

$R^3$ is H or alkyl; and $R^4$ is H or alkyl.

2. The compound of claim 1, wherein $R^2$ is in the R-configuration.

3. The compound of claim 1, wherein $R^2$ is phenyl, naphthyl, or heteroaryl.

4. The compound of claim 1, wherein $R^2$ is phenyl or naphthyl.

5. The compound of claim 1, wherein the compound is represented by Formula IIIa:

IIIa

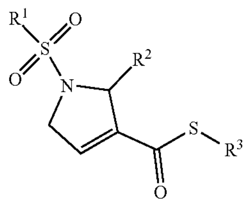

or a pharmaceutically acceptable salt thereof.

6. The compound of claim 1, wherein the compound is represented by Formula Ia:

Ia

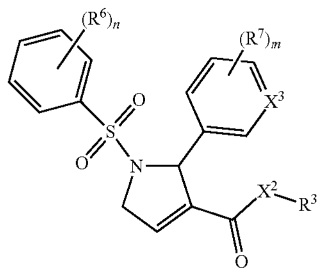

or a pharmaceutically acceptable salt thereof; wherein $X^2$ is S;

$X^3$ is CH, $CR^7$, or N;

$R^6$ and $R^7$ are each, independently for each occurrence, selected from alkyl, halo, hydroxyl, carboxyl, acyl, ester, thioester, alkoxy, phosphoryl, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, aralkyl, carbamoyl, and alkylcarbamoyl; and n and m are each independently 0-5.

7. The compound of claim 6, wherein the compound is represented by Formula Ib:

Ib

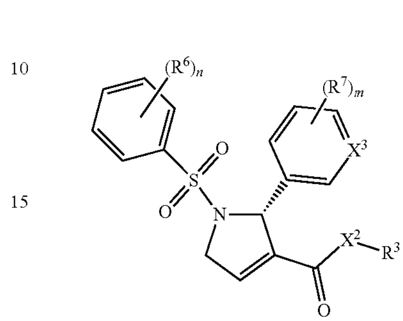

or a pharmaceutically acceptable salt thereof; wherein $X^2$ is S;

$X^3$ is CH, $CR^7$, or N;

$R^6$ and $R^7$ are each, independently for each occurrence, selected from alkyl, halo, hydroxyl, carboxyl, acyl, ester, thioester, alkoxy, phosphoryl, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, aralkyl, carbamoyl, and alkylcarbamoyl; and n and m are each independently 0-5.

8. The compound of claim 6, wherein the compound is represented by Formula Ic or Id:

Ic

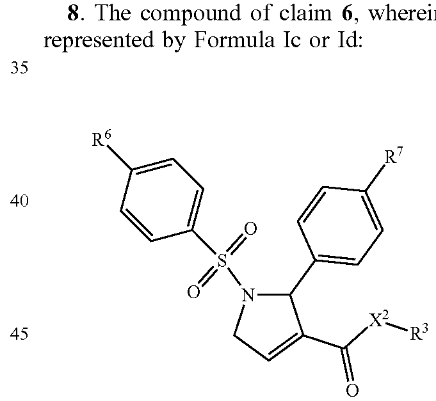

Id

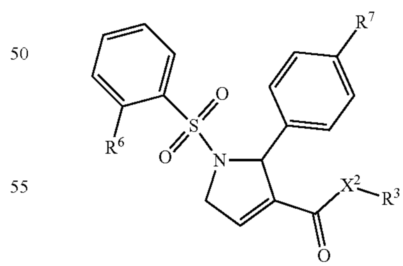

or a pharmaceutically acceptable salt thereof; wherein $X^2$ is S;

$X^3$ is CH, $CR^7$, or N;

$R^6$ and $R^7$ are each, independently for each occurrence, selected from alkyl, halo, hydroxyl, carboxyl, acyl, ester, thioester, alkoxy, phosphoryl, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, aralkyl, carbamoyl, and alkylcarbamoyl and n and m are each independently 0-5.

9. The compound of claim 6, wherein the compound is represented by Formula Ie or If:

Ie

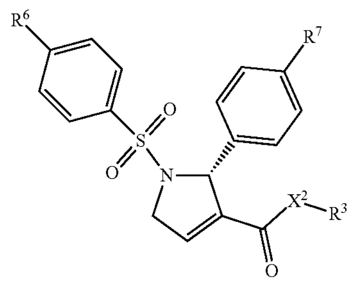

If

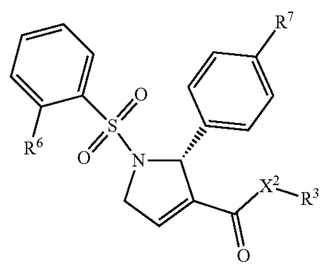

or a pharmaceutically acceptable salt thereof; wherein $X^2$ is S;

$X^3$ is CH, $CR^7$, or N;

$R^6$ and $R^7$ are each, independently for each occurrence, selected from alkyl, halo, hydroxyl, carboxyl, acyl, ester, thioester, alkoxy, phosphoryl, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, aralkyl, carbamoyl, and alkylcarbamoyl; and n and m are each independently 0-5.

10. The compound of claim 6, wherein the compound is represented by Formula IIc, or IId:

IIc

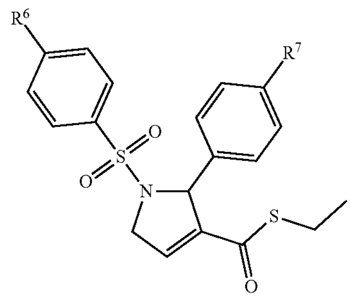

-continued

IId

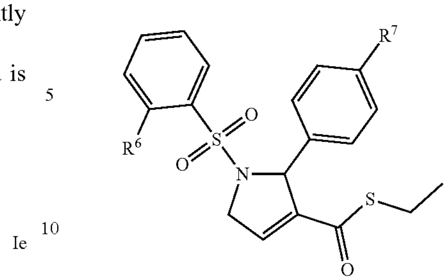

or a pharmaceutically acceptable salt thereof; wherein $R^6$ and $R^7$ are, independently for each occurrence, selected from alkyl, halo, hydroxyl, carboxyl, acyl, ester, thioester, alkoxy, phosphoryl, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, aralkyl, carbamoyl, and alkylcarbamoyl.

11. The compound of claim 6, wherein the compound is represented by Formula IIg, or IIh:

IIg

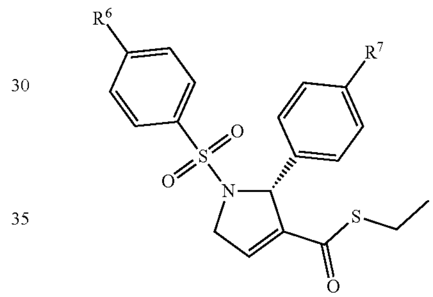

IIh

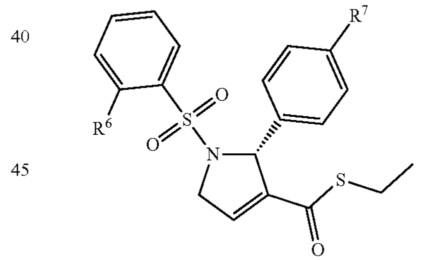

or a pharmaceutically acceptable salt thereof; wherein $R^6$ and $R^7$ are, independently for each occurrence, selected from alkyl, halo, hydroxyl, carboxyl, acyl, ester, thioester, alkoxy, phosphoryl, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, aralkyl, carbamoyl, and alkylcarbamoyl.

12. The compound of claim 6, wherein $R^6$ is halo, or nitro.

13. A composition comprising a compound of claim 1 and at least one pharmaceutically acceptable excipient.

14. A method of modulating cardiac rhythmicity in a subject, comprising administering a compound of claim 1 or a pharmaceutically acceptable salt thereof to the subject.

15. The compound of claim 1, wherein the compound is selected from:

-continued
FS144
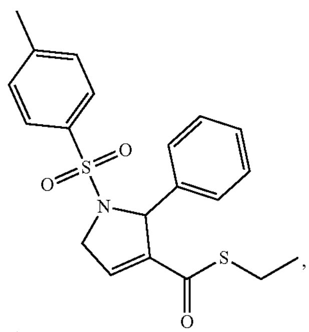
FS145
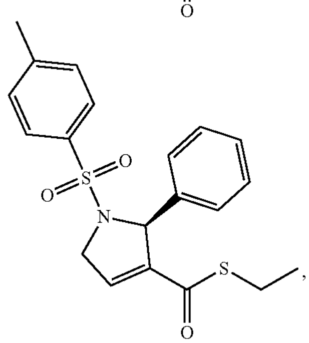
FS146
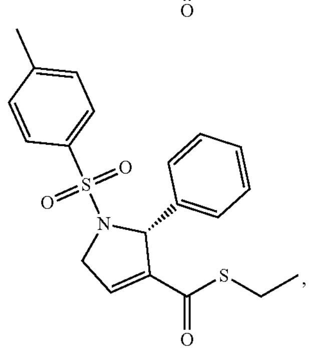
FS152
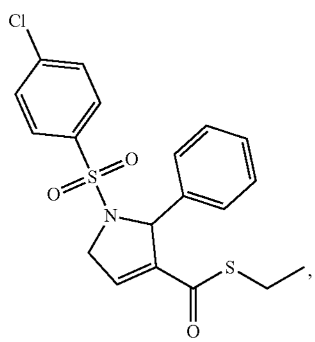
FS153
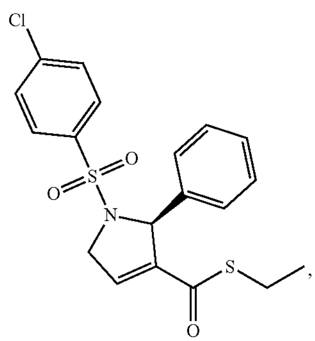
FS154
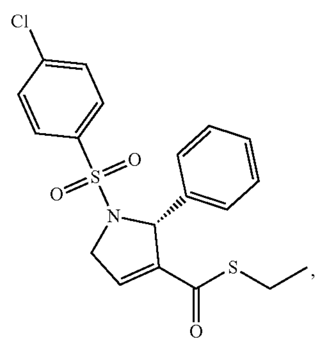
FS155
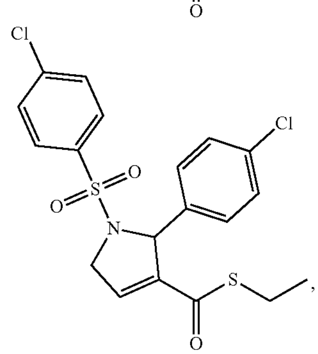
FS156
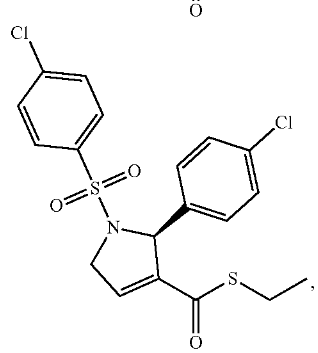
FS157
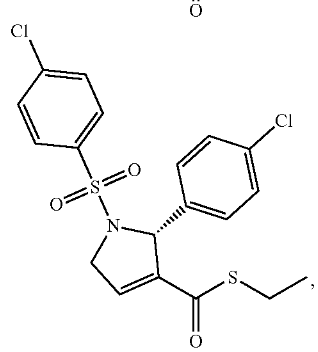
FS158
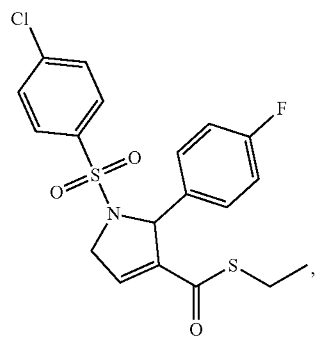

-continued
FS159
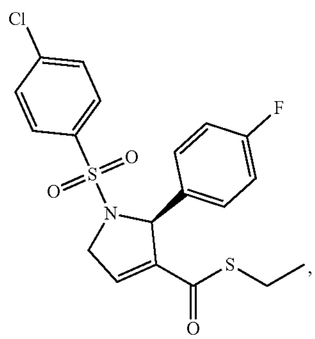
FS160
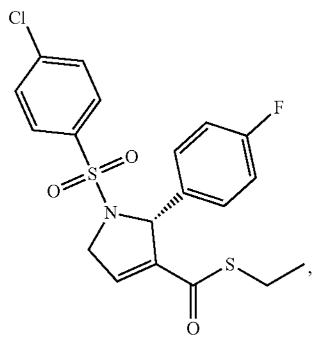
FS161
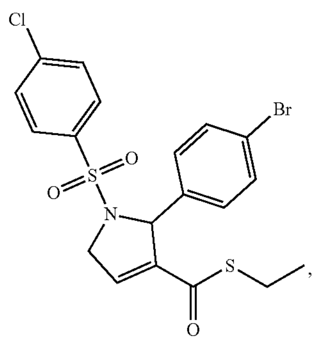
FS162
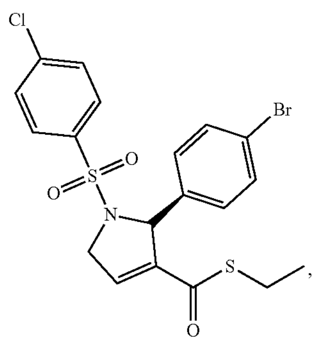
-continued
FS163
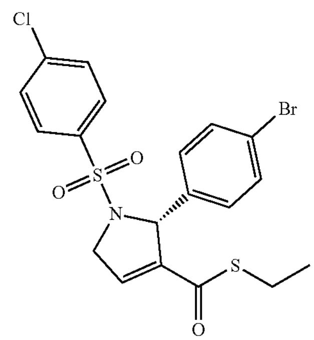
FS173
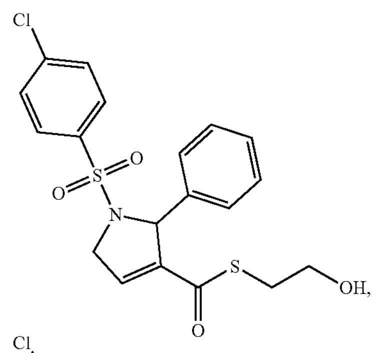
FS174
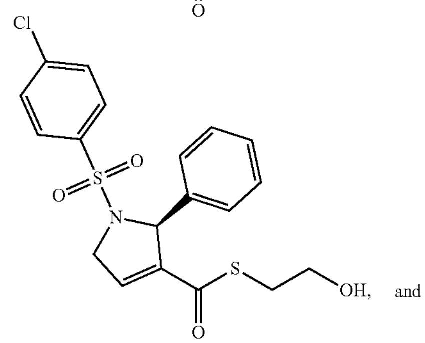
and
FS175
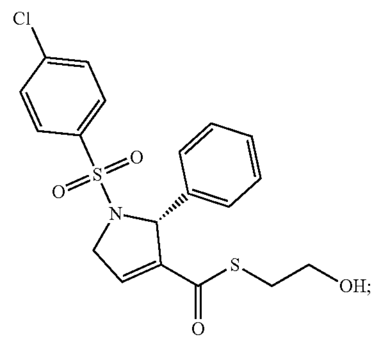
or a pharmaceutically acceptable salt thereof.
16. The compound of claim 6, wherein $R^6$ is halo.
17. The compound of claim 6, wherein $R^7$ is halo, alkyl, cyano, or ester.
* * * * *